United States Patent
Mabus et al.

(10) Patent No.: US 8,188,081 B2
(45) Date of Patent: *May 29, 2012

(54) METHODS OF TREATING INFLAMMATION USING PROKINETICIN 1 RECEPTOR ANTAGONISTS

(75) Inventors: John R. Mabus, East Greenville, PA (US); Jeffrey M. Palmer, Chalfont, PA (US); Stephen M. Prouty, Doylestown, PA (US); Pamela J. Hornby, Penllyn, PA (US); Paul R. Wade, Philadelphia, PA (US)

(73) Assignee: Janssen Pharmaceutica, NV (BE)

( * ) Notice: Subject to any disclaimer, the term of this patent is extended or adjusted under 35 U.S.C. 154(b) by 0 days.

This patent is subject to a terminal disclaimer.

(21) Appl. No.: 12/797,266

(22) Filed: Jun. 9, 2010

(65) Prior Publication Data

US 2011/0136811 A1      Jun. 9, 2011

Related U.S. Application Data

(62) Division of application No. 11/374,683, filed on Mar. 14, 2006, now Pat. No. 7,825,117.

(60) Provisional application No. 60/731,421, filed on Oct. 28, 2005, provisional application No. 60/665,002, filed on Mar. 24, 2005.

(51) Int. Cl.
*A61K 31/53* (2006.01)
*A01N 43/64* (2006.01)

(52) U.S. Cl. ........................................ 514/241; 514/245

(58) Field of Classification Search ........................ None
See application file for complete search history.

(56) References Cited

U.S. PATENT DOCUMENTS

2003/0225075 A1    12/2003    Agarwal et al.
2004/0156842 A1    8/2004    Thompson et al.

FOREIGN PATENT DOCUMENTS

| WO | WO 02/36625 A2 | 5/2002 |
| WO | WO 2004/087054 A2 | 10/2004 |
| WO | WO 2005/007164 A1 | 1/2005 |

*Primary Examiner* — Ruixiang Li

(57) ABSTRACT

The present invention relates to prokineticin 1 receptor antagonists and methods of using the same to modulate intestine epithelial functions and to treat inflammation in the intestine in a mammal.

6 Claims, 20 Drawing Sheets
(2 of 20 Drawing Sheet(s) Filed in Color)

Matrix Assisted Laser Desorption(MALD1) mass spectum of protein mixture $EC_{50} = 8.2$ nM
$EC_{60} = 12.3$ nM
$EC_{70} = 19.2$ nM
$EC_{80} = 33.0$ nM
$EC_{90} = 74.8$ nM ▲ n=7

Mean ± SD
*$P<0.001$ Serosal vs. Mucosal addition of PK1 peptide

Pkr1 mRNA in DSS colitis

PK1R mRNA in MO colitis

PK1 and PK1R expression in rat tissues

PK1R mRNA

PK1R mRNA

PK1
- local release
- hormone (gastric release)

METHODS OF TREATING INFLAMMATION USING PROKINETICIN 1 RECEPTOR ANTAGONISTS

CROSS-REFERENCE TO RELATED APPLICATIONS

This Application is a divisional of U.S. application Ser. No. 11/374,683 filed Mar. 14, 2006, issued as U.S. Pat. No. 7,825,117, which claims priority to U.S. Provisional Patent Application No. 60/731,421, filed on Oct. 28, 2005, now abandoned, and 60/665,002 filed on Mar. 24, 2005, now abandoned, which are hereby incorporated by reference in their entirety.

STATEMENT REGARDING FEDERALLY SPONSORED RESEARCH OR DEVELOPMENT

The research and development of the invention described below were not federally sponsored.

FIELD OF THE INVENTION

The present invention relates to novel compounds that function as modulators of the PK1 receptor, and particularly to a new class of potent and selective antagonists of the PK1 receptor. The present invention also relates to the novel compounds, their pharmaceutically acceptable salts, and pharmaceutically acceptable compositions thereof which are useful as potent and selective antagonists of the PK1 receptor in mammals and methods for using these antagonists as therapeutic agents for disease states in mammals caused by activity of the PK1 receptor.

The present invention also relates to biological materials that are useful for functional analyses of the biological activity of the PK1 receptor, and their uses in identifying compounds that modulate the biological activity of the PK1 receptor. The present invention further relates to methods of measuring the biological activities of the prokineticin 1 receptor. Particularly, the present invention relates to methods of identifying compounds that increase or decrease the biological activities of the prokineticin 1 receptor.

BACKGROUND OF THE INVENTION

Digestion involves the breakdown of food materials into molecules that can be delivered to and utilized by individual cells of the body. These molecules may serve as energy sources; they may provide essential chemical elements, such as calcium, nitrogen or iron; or they may be complete molecules, e.g., certain amino acids, fatty acids and vitamins, that the cells need but cannot synthesize themselves. Digestion which incorporates the processes of breakdown and assimilation of food materials as well as the elimination of undigestable waste material takes place in a long convoluted tube that extends from the mouth to the anus, known as the gastrointestinal (GI) tract. The GI tract begins with the oral cavity, the mouth, and continues to include the, pharynx, esophagus, stomach, small intestine, large intestine and anus. The GI tract, from beginning to end, has foucalr tissue layers: (1) the mucosa, which is the innermost layer, is made up of columnar epithelial cells that are in direct contact with ingested materials and facilitate fluid and electrolyte transport and digestion and absorption of nutrients, an underlying basement membrane consisting of connective tissue and a thin layer of smooth muscle; (2) the submucosa, which is the second innermost layer, is made up of connective tissue containing small clusters of nerve cells and nerve fibers, and blood and lymph vessels; (3) the muscularis externa, which is the third innermost layer, is made up of two separate layers of smooth muscle tissue oriented in opposing directions and containing a vast network of nerve cell clusters and nerve fibers sandwiched in-between these layers; and (4) the serosa, which is the outermost layer consisting of a coating of connective tissue that is in contact with the environment of the peritoneal cavity of the abdomen.

Along most of the GI tract, the muscularis externa is made up of two opposing layers of smooth muscle, the inner layer, in which the cellular orientation is perpendicular to the long axis of the gut, and the outer layer, in which cellular orientation is parallel to the long axis of the gut. Coordinated contractions of these muscle layers produce ring-like constrictions that mix food, as well as wave-like motions, known as peristalsis, that move food along the GI tract. (See FIG. 29). At several points, the circular layer of muscle thickens into heavy bands forming valve-like constrictions called sphincters, which by relaxing and contracting, act to regulate the passage of food from one area of the GI tract to another.

Breakdown and assimilation of nutrients from food materials is accomplished chiefly by the highly coordinated activities of the stomach and small intestine. The stomach is influenced by both the nervous and endocrine systems. Anticipation of food and the presence of food in the mouth stimulate churning movements of the stomach and the production of gastric juices. When food reaches the stomach, its presence causes the release of the hormone gastrin from gastric endocrine cells into the bloodstream. Gastrin acts on the cells of the stomach to increase their secretion of gastric juices.

Food is converted in the stomach to a semiliquid mass as a result of gastric juices, including pepsin, hydrochloric acid and the churning motions. The food is then emptied into the small intestine, where the breakdown of food is completed. The resulting nutrient molecules are then absorbed into the circulatory system, from which they are delivered to the individual cells. The small intestine contains a variety of digestive secretions, some produced by the intestinal cells and some by the pancreas and liver. Other epithelial cells, the goblet cells of the mucosa, secrete mucus. The digestive activities of the small intestine are coordinated and regulated by hormones. In addition to hormonal influences, the intestinal tract is also regulated by the autonomic nervous system, which is involved in the secretion of digestive enzymes and in contraction. Thus, a complex interplay of stimuli and checks and balances serves to activate digestive enzymes, adjust the chemical environment and regulate the movement of ingested materials in the intestines.

The large intestine is involved in the absorption of water, sodium and other electrolytes. Some of its epithelial cells secrete mucus, which lubricates undigested food residue. Large amounts of water enter the stomach and small intestine by osmosis from body fluids or as secretions of the glands lining the digestive tract. When the absorption process is interfered with and/or secretions from the mucosal glands becomes enhanced, as in diarrhea, severe dehydration can result.

Functional bowel disorders involve abnormal motility and secretion within organs of the GI tract, and are characterized by abdominal discomfort/pain. The Criteria for these disorders are summarized by gastroenterologists in the 'Rome II criteria' (See, for example, Rome II Diagnostic criteria for the Functional Gastrointestinal Disorders, Second Edition, Senior Editor Douglas A. Drossman, M. D., Management Services, McLean, Va. (2000)). Based on these criteria the disorders are common and include, but are not limited to, functional dyspepsia, irritable bowel syndrome (IBS), gastroesophageal reflux disease (GERD), non-erosive reflux disease (NERD), and chronic constipation (including colonic inertia, idiopathic pseudoobstruction). GERD is extremely prevalent, is usually associated with non-cardiac chest pain and may be treated with acid-suppressing agents and prokinetic agents. IBS is characterized by the presence of reoccurring constipation and/or diarrhea, which can be associated with gaseous distention/bloating and abdominal discomfort/pain (Thompson, W. G. and Heaton, K. W. *Gastroenterology* 1980, 79, 283-288). The onset of the pain of IBS is associated with a change in the frequency and/or form of stool and can be relieved by defecation. IBS is an extremely prevalent condition that occurs to varying severity in 10-15% of the population (Saito, Y. A.; Schoenfeld, P.; and Locke, G. R. *Am. J. Gastroenterol.* 2002, 97, 1910-1915). The pain may be treated with smooth muscle relaxants and antidepressants (Jackson, J. L.; O'Malley, P. G.; Tomkins, G.; Balden, E.; Santoro, J.; and Kroenke, K.; *Am. J. Med.* 2000, 108, 65-72; Jailwala, J.; Imperiale, T. F.; and Kroenke, K.; *Ann. Intern. Med.* 2000, 133:136-147; Akehurst, R. and Kaltenthaler, E. *Gut* 2001, 48, 272-282; Poynard, T.; Regimbeau, C.; and Benhamou, Y.; *Aliment Pharmacol. Ther.* 2001, 15, 355-361). Severe diarrhea predominant IBS is treated by alosetron, whereas constipation predominant IBS is treated by tegaserod. Functional dyspepsia is a disorder of the upper GI tract with symptoms exacerbated by a meal and associated with early satiety, nausea and vomiting. Although its etiology is unknown, prokinetic agents may relieve the symptoms of IBS. In some patients there is overlap in symptoms between GERD/NERD, functional dyspepsia and IBS. Treatments for functional bowel disorders, such as IBS, have low efficacy and are associated with adverse effects. For example, alosetron is approved by the FDA on a risk management program because it is associated with an increase in ischemic colitis. No treatments effectively alleviate pain in functional bowel disorders.

In addition to functional disorders, inflammatory bowel diseases (IBD) are common and include ulcerative colitis (UC) and Crohn's disease (CD). Although there may be a genetic component to CD, the etiology of both UC and CD is unknown. UC is a diffuse mucosal disease of the colon, characterized by inflammation and ulceration, which is associated with diarrhea and abdominal cramping. The mucosal inflammation progresses from the rectal area to eventually extend through the large bowel. CD is a transmural inflammation that most frequently involves the distal small bowel and colon. The inflammation can result in ulcers of varying involvement and in severe cases can result in transmural scarring and chronic inflammation. Both infectious and dysregulated immune functions may contribute to disease onset. Therapies for IBD include corticosteroids, immunosuppressives (azathioprine, mercaptopurine, and methotrexate) and aminosalicylates (5-ASA). These therapies involve suppression of the immune system by mimicking corticosteroids, or have unknown mechanisms of action. Oral corticosteroid use is associated with serious adverse effects, whereas immunosuppressives and aminosalicylates are only moderately effective. Infliximab (a chimeric monoclonal anti-tumor necrosis factor antibody) is effective in CD, however, its use is associated with the presence of antibodies, which reduce its efficacy. There are currently no treatments that target the motility and secretory abnormalities or painful sensation that are associated with gut inflammation.

The cysteine rich proteins known as Prokineticin 1 (PK1) and Prokineticin 2 (PK2), as well as variants, fragments and molecules having PK activity, have been identified. PK1 and PK2 have been shown to contract gastrointestinal smooth muscle (Li, M.; Bullock, C. M.; Knauer, D. J.; Ehlert, F. J.; and Zhou, Q. Y., *Mol. Pharmacol.* 2001, 59, 692-698), and suppress feeding (Negri, L.; Lattanzi, R.; Giannini, E.; De Felice, M.; Colucci, A. and Melchiorri, P. *Brit. J. Pharmacol.* 2004, 142, 181-191). PK1 and PK2 act on both PK1 and PK2 receptors, and limited structural changes of C-terminal cysteine-rich regions of these related PKs are tolerated. For example, chimeric PKs, where the cysteine-rich domains of PK1 and PK2 were exchanged between the two and a splice variant of PK2 that included a 21 residue insertion in its C-terminal domain retained activity (Bullock, C M; Li J. D.; Zhou, Q. Y.; *Mol. Pharmacol.* 2004, 65(3), 582-8). A PK variant binds to receptors of primary sensory neurons, and results in an intense sensitization of peripheral nociceptors to thermal and mechanical stimuli (Mollay, C.; Weschelberger, C.; Mignogna, G.; Negri, L.; Melchiorri, P.; Barra, D.; Kreil, G.; *Eur. J. Pharmacol.* 1999, 374, 189-196; Negri, L.; Lattanzi, R.; Giannini, E.; Metere, A.; Colucci, M.; Barra, D.; Kreil, G.; Melchiorri, P.; *Brit. J. Pharmacol.* 2002, 137(8), 1147-54).

PK1 induces proliferation, migration and fenestration in capillary endothelial cells derived from endocrine glands. The expression of PK mRNA has been observed in steroidogenic glands, ovary, testis, adrenal and placenta. (LeCouter, J.; Kowalski, J.; Foster, J.; Hass, P., Zhang, Z.; Dillard-Telm, L., Frantz, G., Rangell, L.; DeGuzman, L.; Keller, G. A.; Peale, F.; Gurney, A.; Hillan, K. J.; Ferrara, N. *Nature* 2001, 412 (6850), 877-84). In 2002 the identification of the PK1 receptor provided a novel molecular basis for the regulation of angiogenesis in endocrine glands (Masuda, Y.; Takatsu, Y.; Terao, Y.; Kumano, S.; Ishibashi, Y.; Suenaga, M.; Abe, M.; Fukusumi, S.; Watanabe, T.; Shintani, Y.; Yamada, T.; Hinuma, S.; Inatomi, N.; Ohtaki, T.; Onda, H.; Fujino, M.; *Biochem. Biophys. Res. Commun.* 2002, 293(1), 396-402; LeCouter, J.; Lin, R.; Ferrara, N.; *Cold Spring Harb Symp Quant Biol.* 2002, 67, 217-21). For example, adenoviral delivery of PK1 to the mouse testis results in a potent angiogenic response (LeCouter, J.; Lin, R.; Tejada, M.; Frantz, G.; Peale, F.; Hillan, K. J.; Ferrara, N. *Proc. Natl. Acad. Sci. USA.* 2003, 100, 2685-90). Recently, it was shown that PK1 mRNA is not normally expressed in colorectal normal mucosa but is detected in colorectal cancer cells (Goi, T.; Fujioka, M.; Satoh, Y.; Tabata, S.; Koneri, K.; Nagano, H.; Hirono, Y.; Katayama, K.; Hirose, K. and Yamaguchi., *Cancer Res.* 2004, 64,1906-1910).

Thus, PK1 receptor modulators, and in particular PK1 receptor antagonists, may be useful in the treatment and prevention of various mammalian disease states, for example, visceral pain that is associated with IBS and IBD. Additionally, PK1 receptor modulators, and in particular PK1 receptor antagonists, may be useful for the treatment of GERD or other forms of secretory diarrhea. Additionally, PK1 receptor modulators, and in particular PK1 receptor antagonists, may be useful in treating cancer-specific angiogenesis factor in the large intestine and reproductive organs.

WO200236625 discloses PK1 and PK2 polynucleotides and polypeptides and uses thereof U.S. 20040156842 and corresponding U.S. Pat. No. 6,485, 938 disclose the use of peptide antagonists of PK1 and PK2 to treat inflammation in the intestine. The references disclose that the antagonists include antibodies that specifically bind with PK1 and PK2 and receptors that bind to amino acid sequences disclosed therein.

WO2004087054 discloses methods of modulating gastric acid or pepsinogen secretion by administering a prokineticin receptor antagonist to alter one or more indicia of gastric acid secretion. The reference discloses that the prokineticin receptor antagonist is a modified version of a prokineticin from any species that contains an amino acid sequence at least 80% identical to an amino acid sequence disclosed therein.

None of the references disclose or suggest a small molecule modulator of the PK1 receptor. The identification of such modulators should facilitate the development of novel therapeutics for disorders that involve impaired or enhanced gastrointestinal motility and/or secretion.

It is an aspect of the present invention to provide PK1 receptor modulators, and in particular, PK1 receptor antagonists. It is also an object of the invention to provide a method of treating or ameliorating a condition mediated by the PK1 receptor. And, it is an object of the invention to provide a useful pharmaceutical composition comprising a compound of the present invention useful as a PK1 receptor antagonist.

Another aspect of the invention is a method of monitoring the biological activity of a PK1 receptor in an animal.

These and other aspects and advantages of the invention will become apparent in light of the description below.

SUMMARY OF THE INVENTION

The present inventors have discovered potent antagonists of the PK1 receptor. The present invention is thus directed to a compound of Formula (I):

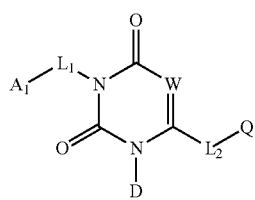

Formula (I)

wherein:

$A_1$ is hydrogen; aryl; heteroaryl; $C_{5-8}$cycloalkyl; or heterocyclyl; provided that $A_1$ is other than piperidin-4-yl, N-t-butoxycarbonyl-piperidin-4-yl, or N-methyl-piperidin-3-yl; and wherein substituents of $A_1$ other than hydrogen are optionally substituted with one to three substituents independently selected from the group consisting of $C_{1-6}$alkyl, hydroxy($C_{1-6}$)alkyl, $C_{1-6}$alkoxy, halogen, nitro, halogenated $C_{1-6}$alkyl, halogenated $C_{1-6}$alkoxy, $C_{1-6}$alkylthio, $C_{1-6}$alkoxycarbonyl, amino, $C_{1-6}$alkylamino, di($C_{1-6}$alkyl)amino, cyano, hydroxy, aminocarbonyl, $C_{1-6}$alkylaminocarbonyl, di($C_{1-6}$alkyl)aminocarbonyl, $C_{1-6}$alkoxycarbonylamino, $C_{1-6}$alkylcarbonyl, $C_{1-6}$alkylthiocarbonyl, formyl, $C_{1-6}$alkylsulfonyl, $C_{1-6}$alkylsulfonylamino, aminosulfonyl, $C_{1-6}$alkylaminosulfonyl, and di($C_{1-6}$alkyl)aminosulfonyl;

$L_1$ is —$(CH_2)_r$— or —$CH_2CH_2X(CH_2)_s$—, optionally substituted with one to three subsitutuents independently selected from the group consisting of $C_{1-6}$alkyl, $C_{2-6}$alkenyl, $C_{2-6}$alkynyl, and halogen; provided that when $A_1$ is hydrogen, r is greater than or equal to 4;

r is an integer of 1 to 5;
s is an integer of 1 to 3;
X is O or S;
D is —P-$A_2$;
$A_2$ is hydrogen; phenyl; heteroaryl other than unsubstituted pyridin-2-yl; or $C_{3-8}$cycloalkyl; wherein phenyl is optionally substituted at the meta or para positions with, and substituents of $A_2$ other than hydrogen and phenyl are optionally substituted with, one to three substituents independently selected from the group consisting of $C_{1-6}$alkyl, $C_{1-6}$alkoxy, halogen, halogenated $C_{1-6}$alkyl, halogenated $C_{1-6}$alkoxy, aryl($C_{1-6}$)alkoxy, phenyl, $C_{1-6}$alkylthio, $C_{1-6}$alkoxycarbonyl, amino, $C_{1-6}$alkylamino, di($C_{1-6}$alkyl)amino, cyano, hydroxy, nitro, $C_{1-6}$alkylcarbonyl, $C_{1-6}$alkylthiocarbonyl, aminocarbonyl, $C_{1-6}$alkylaminocarbonyl, di($C_{1-6}$alkyl)aminocarbonyl, $C_{1-6}$alkylcarbonylamino, and a non fused $C_{3-6}$cycloalkyloxy; provided that no more than two substituents on $A_2$ are aryl($C_{1-6}$)alkoxy, phenyl, or a non fused $C_{3-6}$cycloalkyloxy;

provided that when $A_1$ is unsubstituted phenyl and $L_2$ is —$X_1(CH_2)_2$— wherein $X_1$ is NH, $A_2$ is other than unsubstituted phenyl; phenyl substituted with aryl($C_{1-6}$)alkoxy or phenyl; or phenyl substituted at the meta position with cyano;

and, further provided that when $A_1$ is unsubstituted phenyl and $L_2$ is —$X_1(CH_2)_3$— wherein $X_1$ is NH, $A_2$ is other than phenyl substituted with methoxy;

and, provided that when $A_1$ is 3,4-dichloro-phenyl and P is —$CH_2$—, $A_2$ is other than phenyl substituted at the meta position with trifluoromethyl or trifluoromethoxy;

and, further provided that when $A_1$ is 3,4-dichloro-phenyl and P is —$(CH_2)_2$—, $A_2$ is other than 4-methoxy-phenyl;

in addition, when $A_2$ is hydrogen, P is —$(CH_2)_{4-6}$—, and when $A_2$ is other than hydrogen, P is —$(CH_2)_{1-2}$— or —$CH_2X_2$—;

W is N or CH;

$L_2$ is a bivalent radical selected from the group consisting of
pyrrolidinyl or piperidinyl attached to the triazine ring of Formula (I) via its nitrogen atom, wherein said pyrrolidinyl or piperidinyl is substituted on a carbon atom with —$(CH_2)_{0-2}$—;
—NH—$C_{5-7}$cycloalkyl-$(CH_2)_{0-2}$—; such that when $C_{5-7}$cycloalkyl is cyclohexyl, Q is attached at either the 2- or cis-4-position relative to the position of —NH—;
—$X_1$—$C_{2-6}$alkyl-;
—$X_1$—$(CH_2)_{1-3}$—$X_2$—$(CH_2)_{1-3}$—;
—$X_2$—$(CH_2)_{0-4}$—;
—$X_1$—$(CH_2)_{2-3}$—$X_3$—$(CH_2)_{2-3}$—;
—$NH(CH_2)_{1-4}C(=O)$—, provided that at least one of $R^b$, $R^c$, or $R^d$ is not hydrogen and m is 0;
—$NHC(=O)$—$(CH_2)_{1-4}$—; and
—$X_1$—$CH(R^x)$—$(CR^xR^y)_{1-5}$—;

wherein $X_1$ is —NH— or a direct bond; $X_2$ is —CH=CH—; $X_3$ is O, S, NH, or C=O; $R^x$ and $R^y$ are independently H or $C_{1-4}$alkyl; and provided that $L_2$ in any instance does not exceed 7 atoms in length;

Q is —$(O)_mN(R^a)$-G; and m is 0 or 1;
G is —$C(=NR^b)NR^cR^d$;
$R^a$ and $R^d$ are independently hydrogen, $C_{1-6}$alkyl, $C_{2-6}$alkenyl, or $C_{3-6}$alkynyl, wherein substituents of $R^a$ and $R^d$ other than hydrogen are optionally substituted with one to three substituents independently selected from the group consisting of hydroxy, $C_{1-4}$alkoxy, fluoro, amino, $C_{1-4}$alkylamino, di$C_{1-4}$alkylamino, and $C_{1-4}$alkylcarbonyl; or $R^a$ and $R^c$ are taken together with the atoms to which they are attached to form a 5-8 membered monocyclic ring optionally substituted with oxo;

$R^b$ is hydrogen, $C_{1-6}$alkyl, $C_{2-6}$alkenyl, $C_{3-6}$alkynyl, $C_{2-6}$alkoxycarbonyl, or cyano; or, $R^b$ and $R^c$ are taken together with the atoms to which they are attached to form a 5-8 membered monocyclic ring optionally substituted with oxo;

$R^c$ is hydrogen, $C_{1-10}$alkyl, $C_{2-10}$alkenyl, $C_{3-10}$alkynyl, $C_{3-7}$cycloalkyl, adamantyl, amino, $C_{1-6}$alkylamino, di($C_{1-6}$ alkyl)amino, $C_{1-6}$alkylcarbonyl, $C_{1-6}$alkoxycarbonyl, arylcarbonyl, heteroarylcarbonyl, heterocyclylcarbonyl, aryl, heteroaryl, or heterocyclyl; wherein $C_{1-10}$alkyl, $C_{2-10}$alkenyl, and $C_{2-10}$alkynyl are optionally substituted with one to three substituents independently selected from the group consisting of hydroxy, $C_{1-6}$alkoxy, trifluoromethyl, aryl, heteroaryl, and heterocyclyl; and wherein any aryl- or heteroaryl-containing substituents of $R^c$ are optionally substituted with one to three substituents independently selected from the group consisting of $C_{1-6}$alkyl, $C_{1-6}$alkoxy, halogen, fluorinated $C_{1-6}$alkyl, fluorinated $C_{1-6}$alkoxy, $C_{1-6}$alkylcarbonyl, $C_{1-6}$alkoxycarbonyl, aminocarbonyl, $C_{1-6}$alkylaminocarbonyl, di($C_{1-6}$alkyl)aminocarbonyl, $C_{1-6}$alkoxycarbonylamino, formyl, $C_{1-6}$alkylsulfonyl, $C_{1-6}$alkylsulfonylamino, aminosulfonyl, $C_{1-6}$alkylaminosulfonyl, and di($C_{1-6}$alkyl)aminosulfonyl, nitro, methylthio, hydroxy, and cyano; or, $R^c$ and $R^d$ are taken together with the atoms to which they are attached to form a 5-8 membered monocyclic ring that optionally includes 1 to 2 O or S heteroatoms within the ring, and said ring is optionally substituted with oxo;

with the proviso that in any instance, only one ring optionally exists between $R^a$ and $R^b$, $R^b$ and $R^c$, or $R^c$ and $R^d$;

and enantiomers, diastereomers, tautomers, solvates, and pharmaceutically acceptable salts thereof.

Also provided are methods of identifying a PK1 receptor modulator, by contacting a preparation containing a PK1 receptor with one or more candidate compounds, and identifying a compound that specifically increases or decreases PK1 receptor activity. Such a compound is characterized as a PK1 receptor modulator.

Also provided are methods of identifying a PK1 receptor agonist, by contacting a preparation containing a PK1 receptor with one or more candidate compounds, and identifying a compound that selectively promotes production of a PK1 receptor signal. Such a compound is characterized as a PK1 receptor agonist.

Also provided are methods of identifying a PK1 receptor antagonist, by contacting a preparation containing a PK1 receptor with one or more candidate compounds in the presence of a PK1, and identifying a compound that selectively inhibits production of a PK1 receptor signal. Such a compound is characterized as a PK1 receptor antagonist.

A method of the invention for modulating the PK1 receptor can involve administering a PK1 receptor antagonist to the cell, tissue or animal, capable of generating a PK1 receptor signal.

Also provided are methods of stimulating motility and/or secretion in a mammal, comprising administering to the mammal an effective amount of a PK1 and/or a PK1 agonist.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

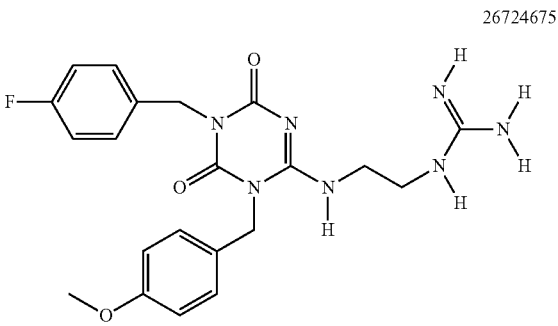

26724675

-continued

28480894

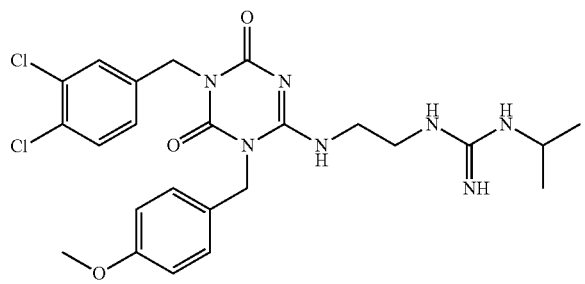

Figure 10:
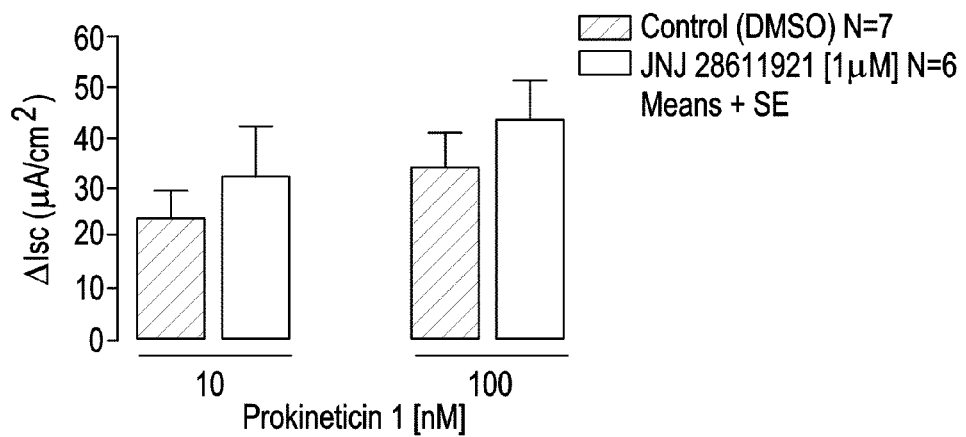

FIG. 10 is a graphical representation that demonstrates that the PK1 evoked increase in Isc was not suppressed in the presence of the substituted aminoguanidine, JNJ 28611921 (see below), a small molecule that is not active at the PK1 receptor but is structurally related to JNJ 27624675 and JNJ 28480894.

28611921

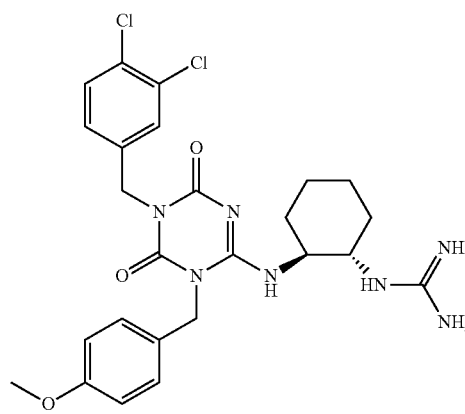

Figure 11:
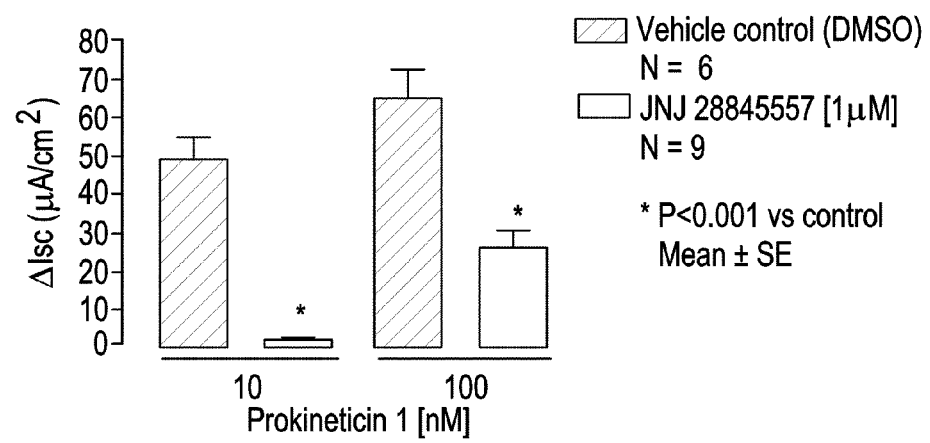

FIG. 11 is a graphical representation that demonstrates that the PK1 evoked increase in Isc was suppressed by the aminobenzimidazole, JNJ 28845557 (see below), a small molecule antagonist at the PK1 receptor.

28845557

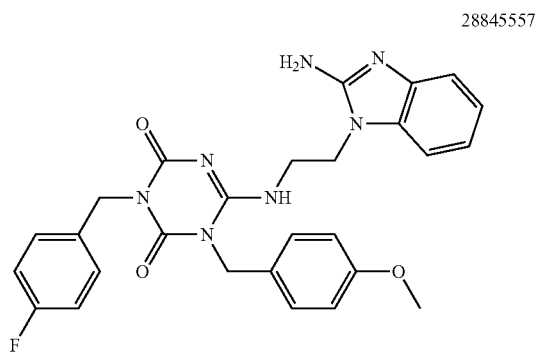

Figure 12:
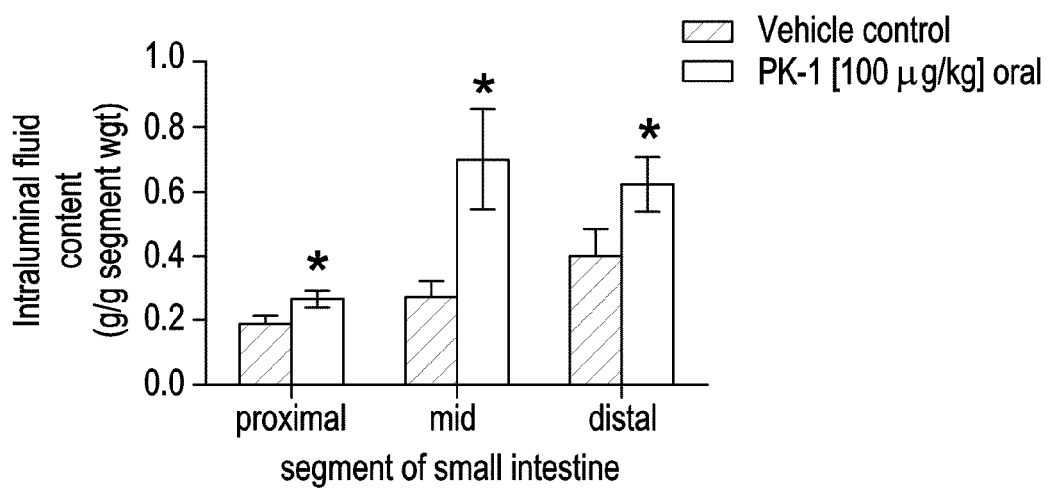

FIG. 12 is a graphical representation that demonstrates that oral PK1 (100 μg/kg) stimulates fluid accumulation in rat small bowel in vivo.

Figure 13:
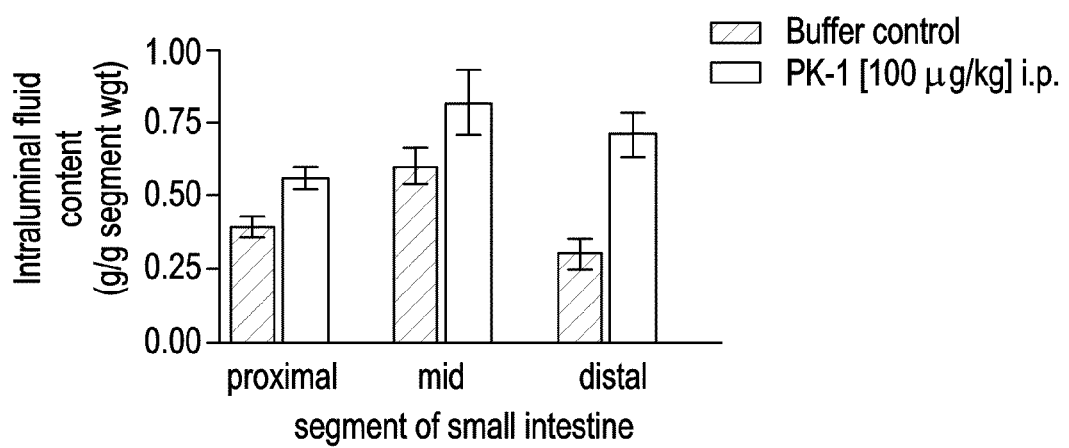

FIG. 13 is a graphical representation that demonstrates that intraperitoneal PK1 (100 μg/kg) stimulates fluid accumulation in rat small bowel in vivo.

Figure 14:
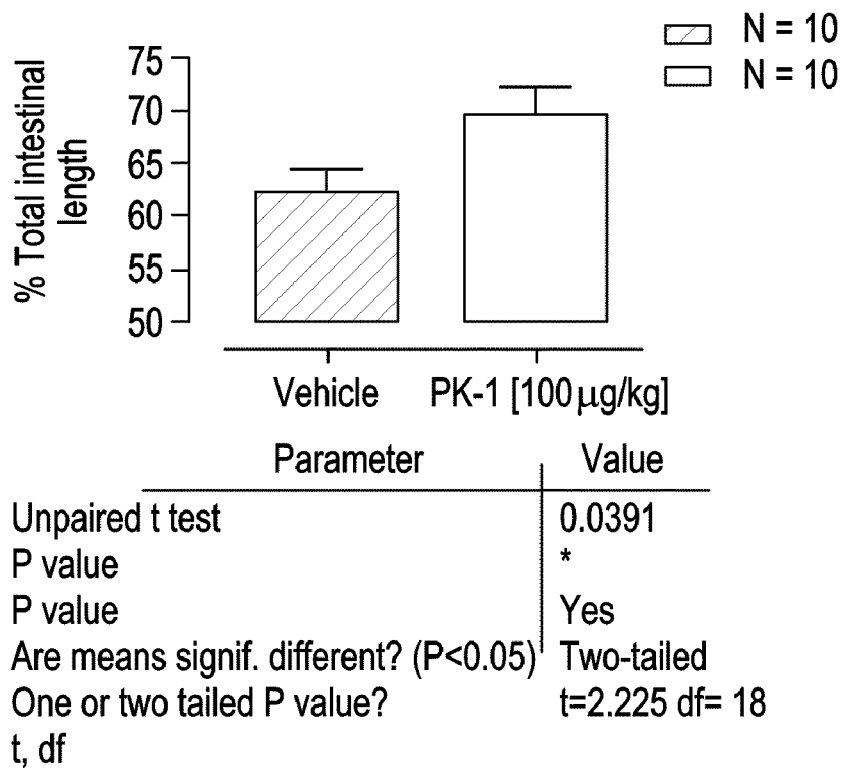

FIG. 14 is a graphical representation that demonstrates that oral PK1 (100 μg/kg) enhanced propulsion of a carmine test meal in the rat small intestine in vivo.

Figure 15:
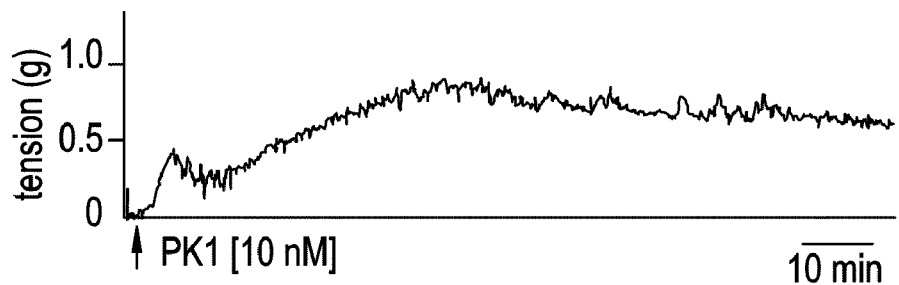

FIG. 15 shows contractile responses of tissue segments obtained from rat GI tract and normalized to the contraction evoked by 1 μM acetylcholine.

Figure 16:
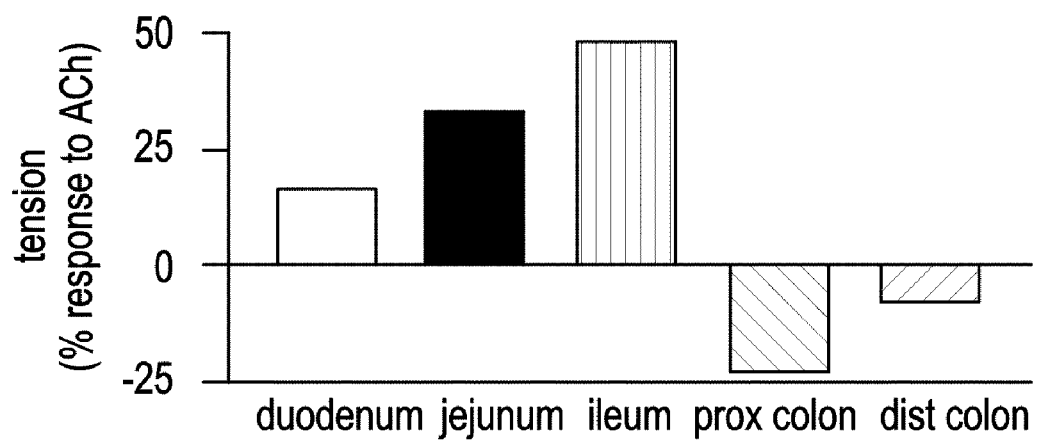

FIG. 16 demonstrates that application of PK1 to intact segments of rat ileum maintained under isometric conditions evoked a biphasic contractile response.

Figure 17A:
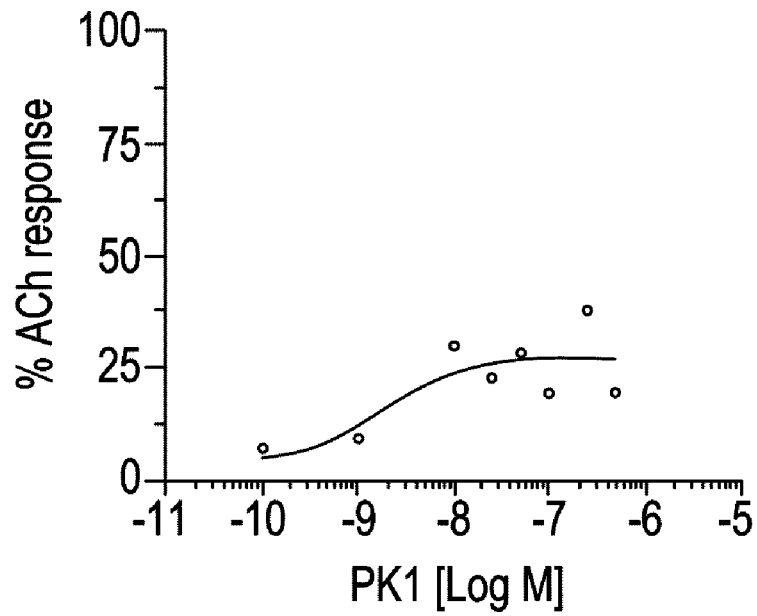
Figure 17B:
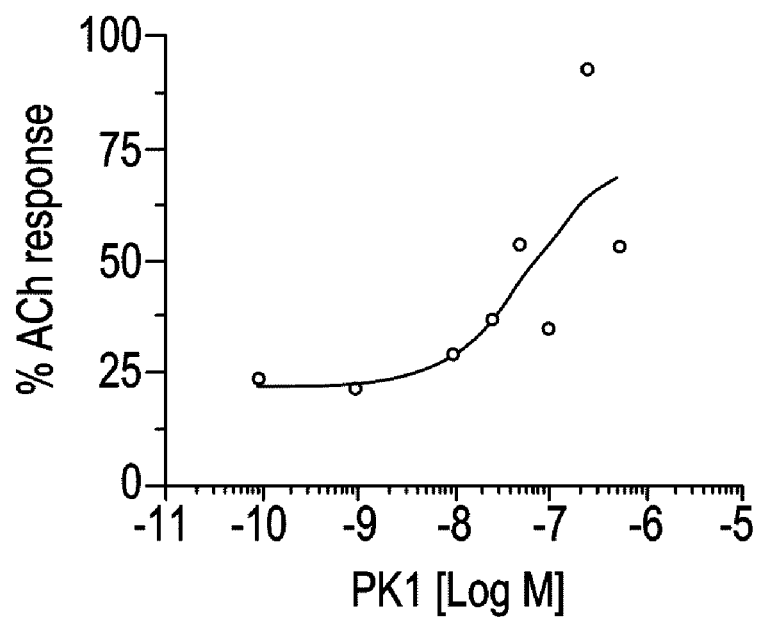

FIGS. 17A and 17B are semi-logarithmic plots of the concentration-response relationships of the early and late phases, respectively, of the PK1-evoked contractile responses in isolated rat ileum. N=2.

Figure 18:
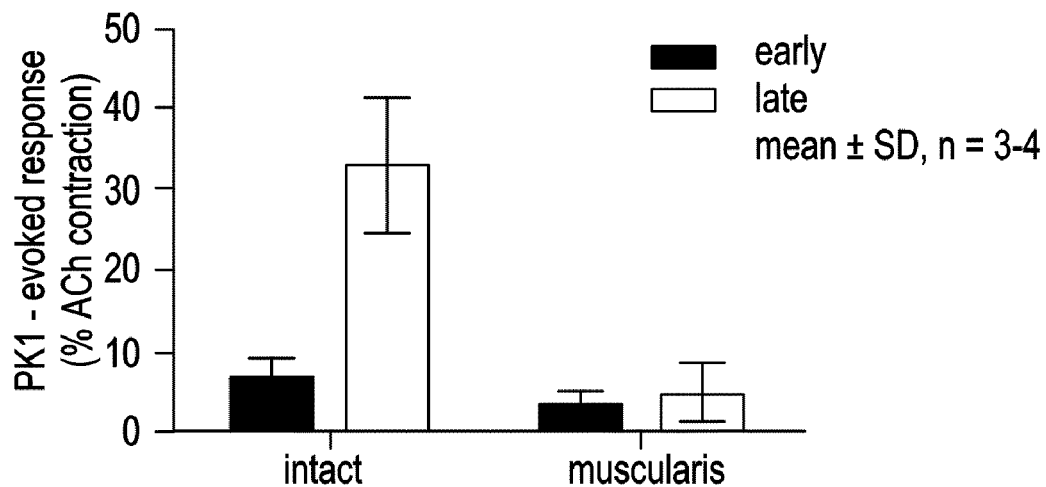

FIG. 18 is a graphical representation which demonstrates that the late contractile response evoked by application of PK1 (250 nM) is absent in mucosa-free preparations of rat ileum.

Figure 19:
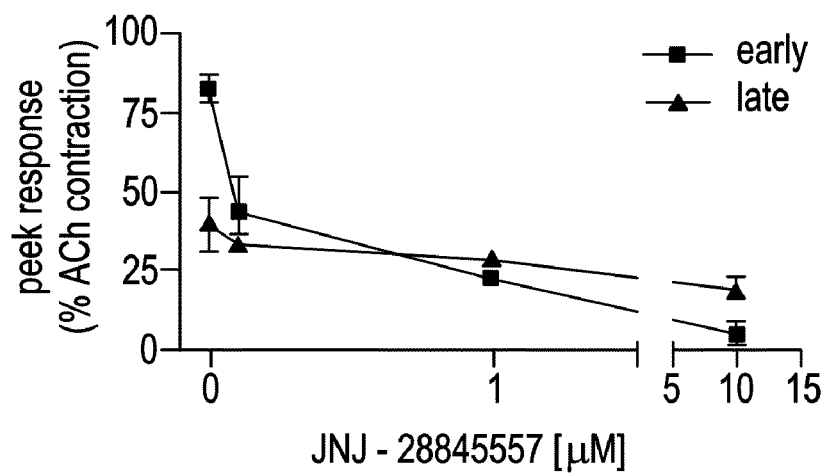

FIG. 19 is a graphical representation which demonstrates that JNJ-28845557 antagonizes both early and late components of the PK1-induced contraction of rat ileal longitudinal smooth muscle.

Figure 20B:
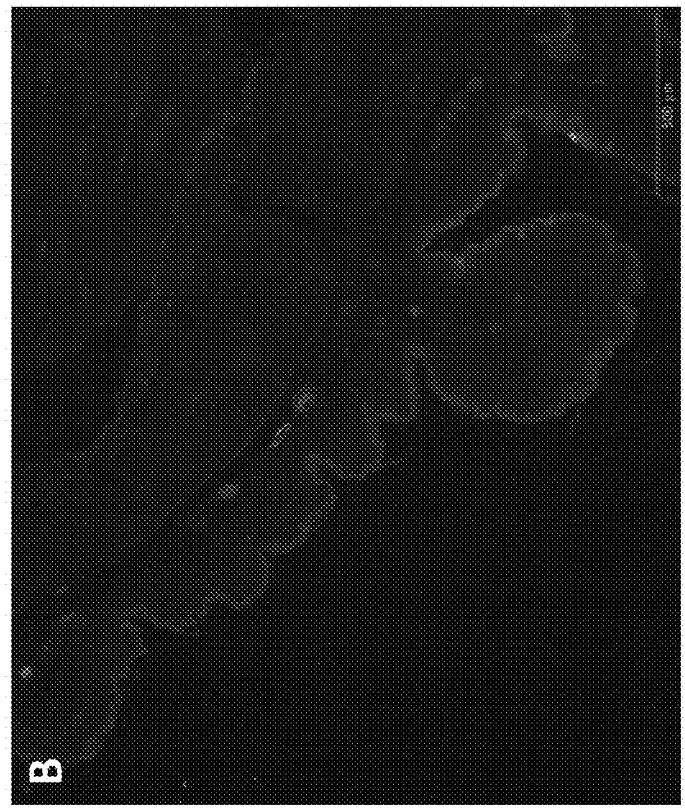
Figure 20A:

FIGS. 20A and 20B show images acquired by fluorescence microscopy demonstrating (A) the observance of PK1—immunoreactivity in the rat gastric mucosa, and (B) the absence of immunofluorescence in an adjacent section incubated only with AlexaFluor 488 —conjugated secondary antibodies, but no primary anti-PK1 antiserum (as a control).

Figure 21A:
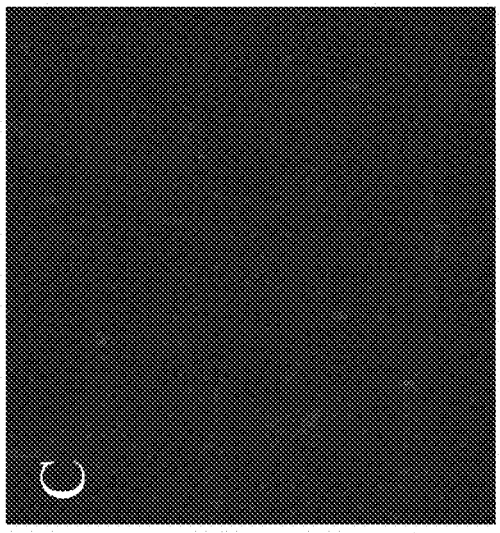
Figure 21B:
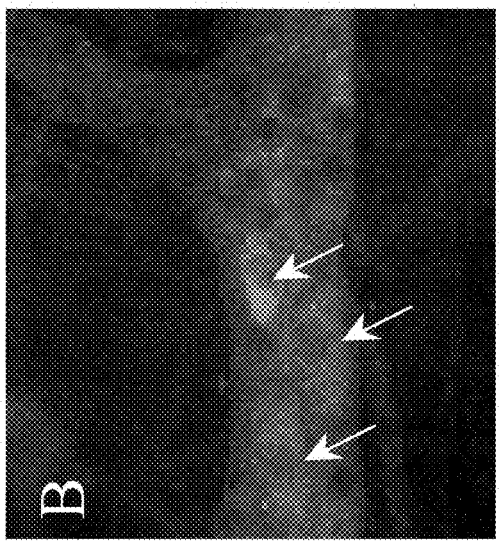
Figure 21C:
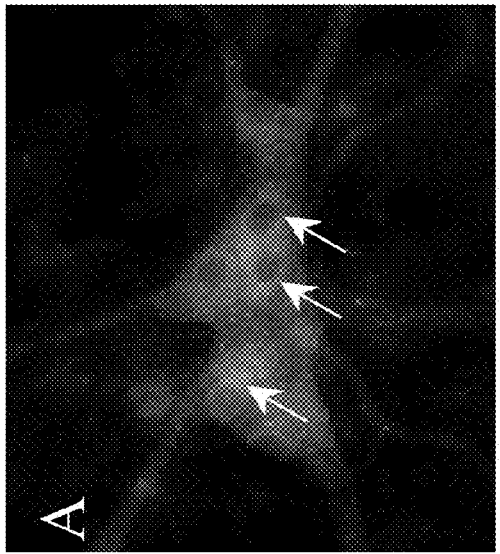

FIGS. 21A, 21B and 21C show images acquired by fluorescence microscopy demonstrating that PK1 receptor—immunoreactivity is localized to neurons in the guinea pig ileal (A) submucosal plexus, and (B) myenteric plexus, but not in a (C) no primary control.

Figure 22:
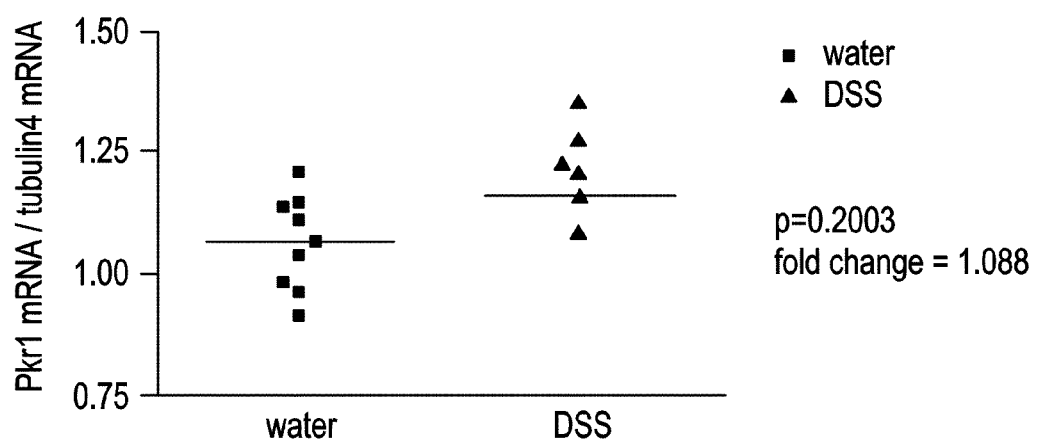

FIG. 22 is a schematic showing the level of expression of PK1 receptor mRNA in murine DSS-induced colitis.

Figure 23:
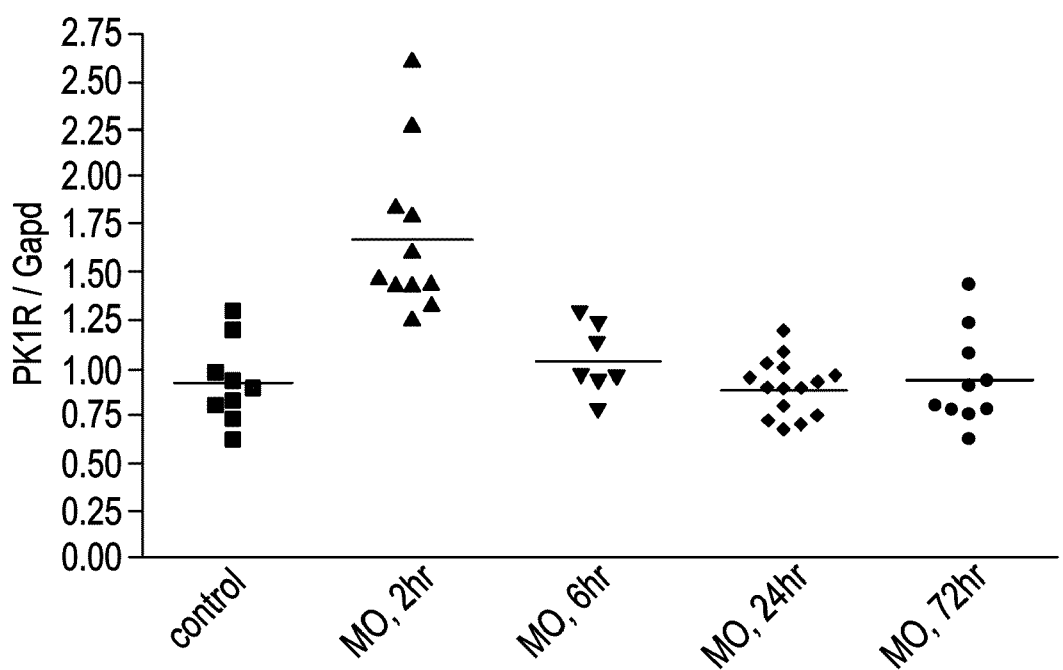

FIG. 23 is a schematic showing the level of expression of PK1 receptor mRNA in murine mustard oil-induced colitis at T=0, 2 hr, 6 hr, 24 hr and 72 hr, respectively.

Figure 24:
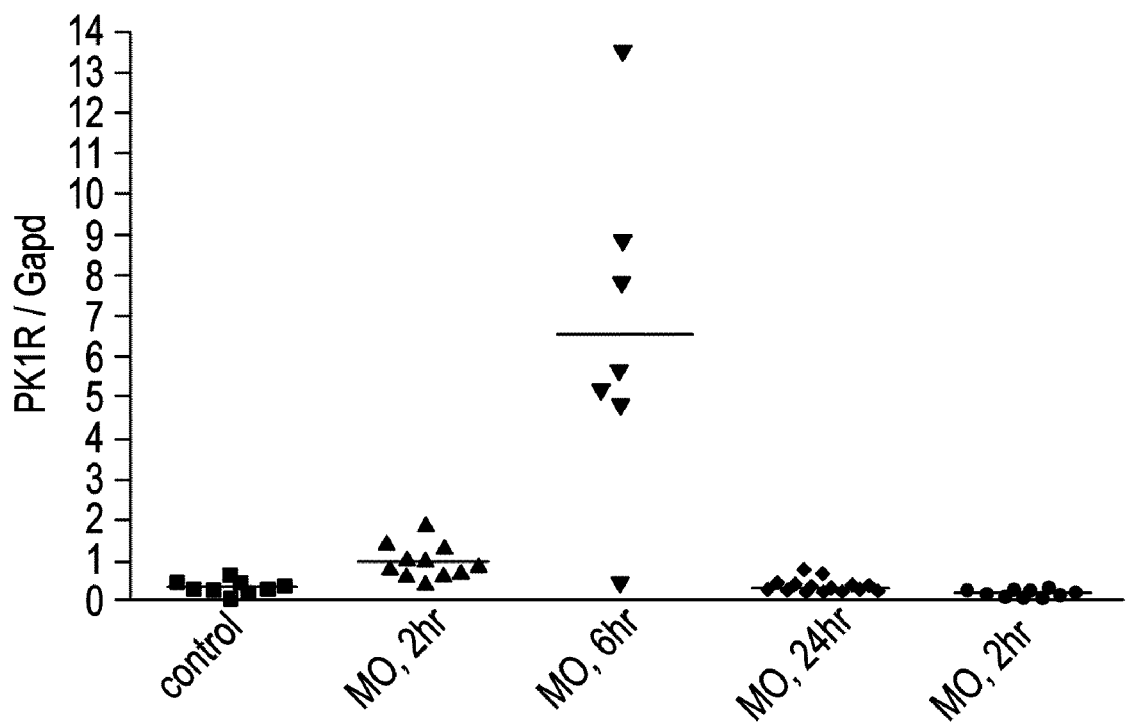

FIG. 24 is a schematic showing the level of expression of PK1 mRNA in murine mustard oil-induced colitis at T=0, 2 hr, 6 hr, 24 hr and 72 hr, respectively.

Figure 25:
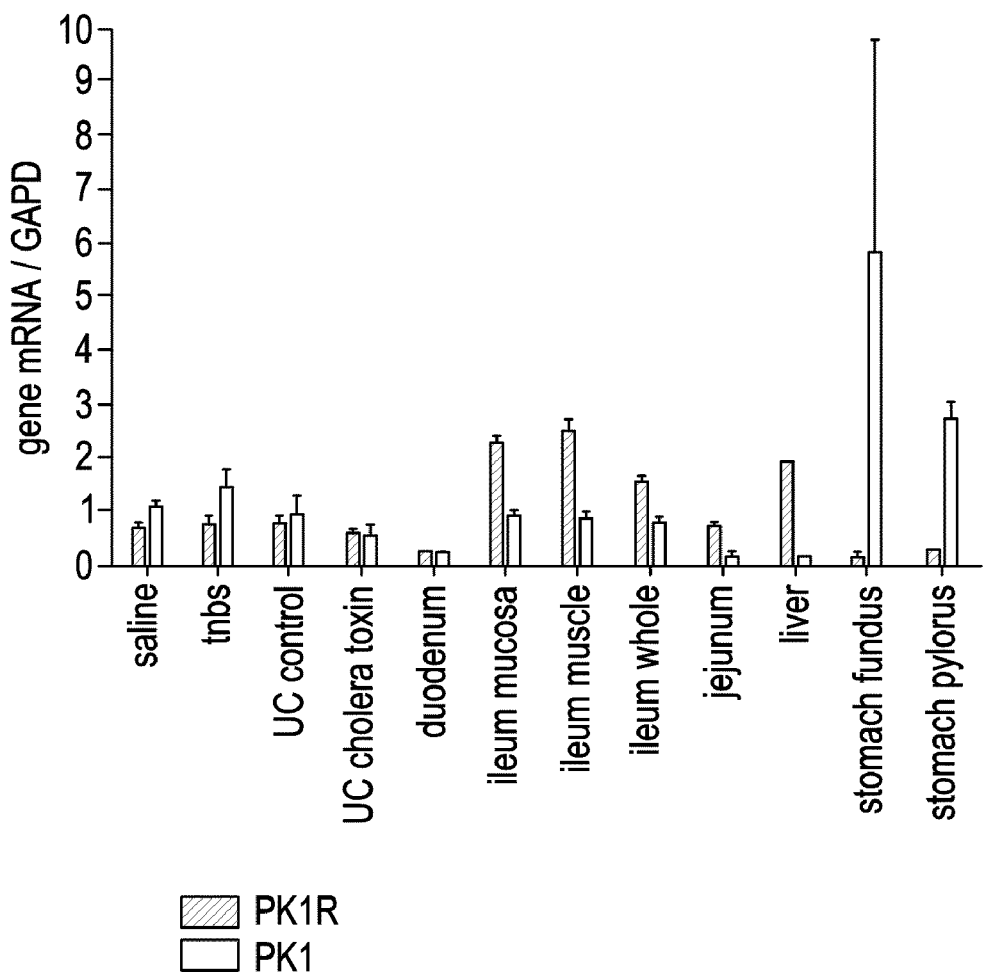

FIG. 25 is a graphical representation which shows the level of expression of PK1 and PK1 peptide receptor expression in various rat tissues.

Figure 26:
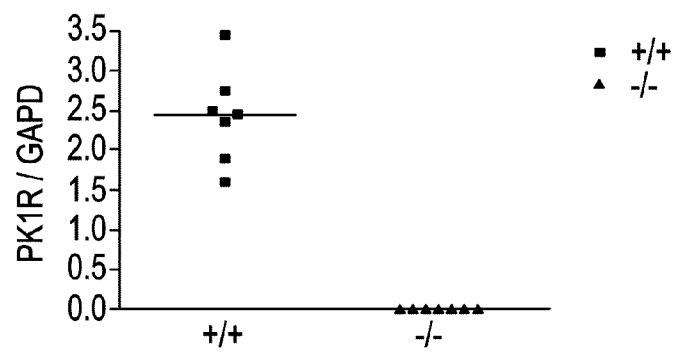

FIG. 26 is a schematic showing the level of expression of PK1 receptor mRNA in PK1 receptor knockout mouse (−/−) and PK1 receptor wild type mouse (+/−), respectively.

Figure 27:
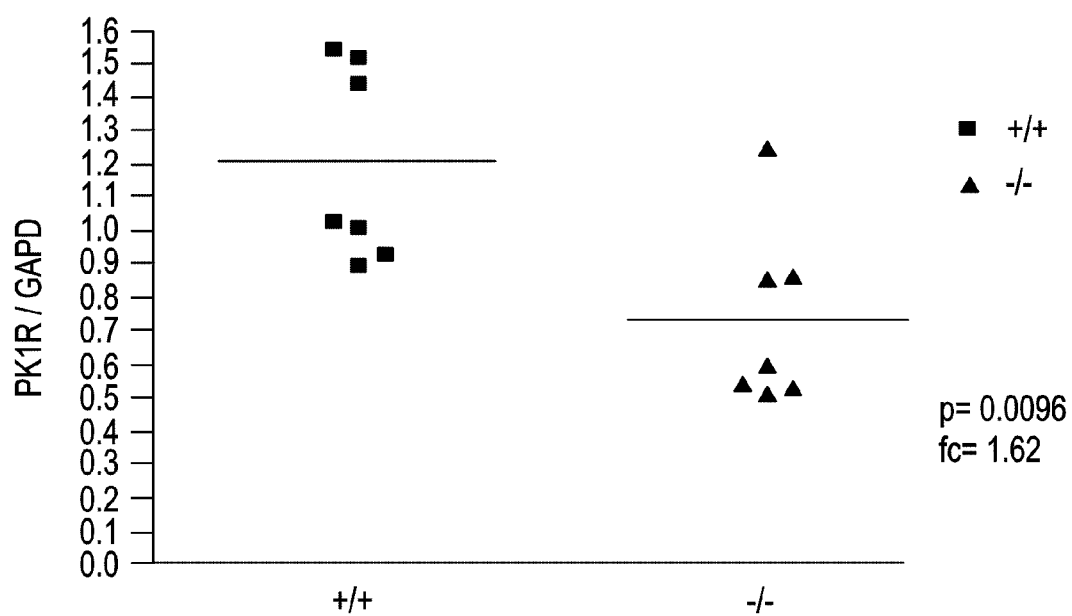

FIG. 27 is a schematic showing the level of expression of PK1 mRNA in PK1 receptor knockout mouse (−/−) and PK1 receptor wild type mouse (+/+), respectively.

Figure 28:
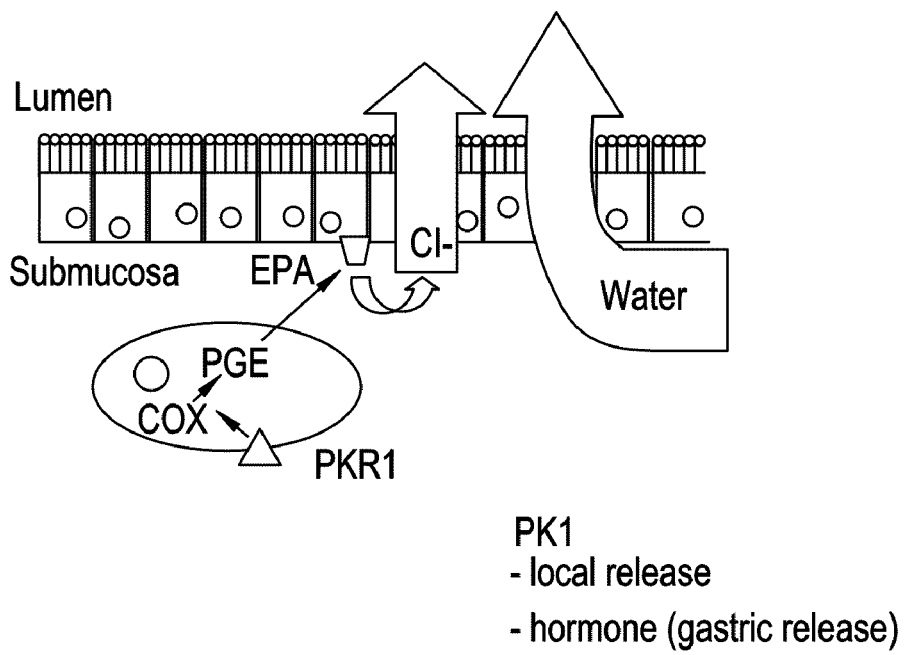

FIG. 28 is a schematic showing the role of PK1 on ion and associated water transport across the gut epithelium.

Figure 29:
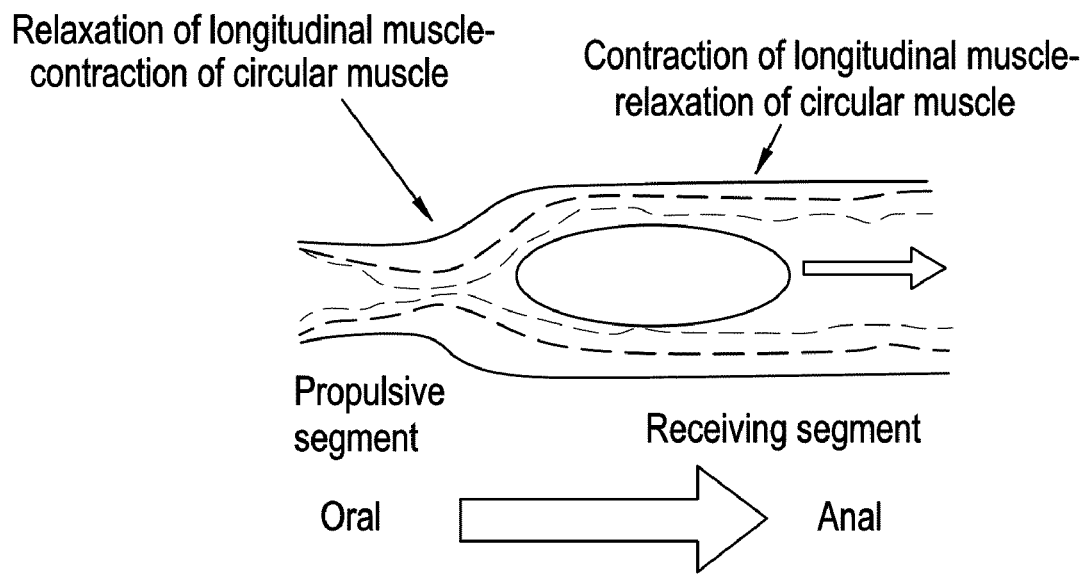

FIG. 29 is a schematic showing how alternating contractions of circular and longitudinal muscles move food along the digestive tract.

DETAILED DESCRIPTION OF THE INVENTION

All publications cited herein are hereby incorporated by reference. Unless defined otherwise, all technical and scientific terms used herein have the same meaning as commonly understood to one of ordinary skill in the art to which the invention pertains.

As used herein, the following underlined terms are intended to have the following meanings:

Chemistry

As used herein, the term "acyl" refers to alkylcarbonyl substituents.

As used herein, unless otherwise noted, "alkyl" whether used alone or as part of a substituent group refers to straight and branched carbon chains having 1 to 8 carbon atoms or any number within this range. The term "alkoxy" refers to an —O alkyl substituent group, wherein alkyl is as defined supra. Similarly, the terms "alkenyl" and "alkynyl" refer to straight and branched carbon chains having 2 to 8 carbon atoms or any number within this range, wherein an alkenyl chain has at least one double bond in the chain and an alkynyl chain has at least one triple bond in the chain. An alkyl and alkoxy chain may be substituted on a carbon atom. In substituent groups with multiple alkyl groups such as $(C_{1-6}alkyl)_2$amino- the $C_{1-6}$alkyl groups of the dialkylamino may be the same or different.

The term "aryl" refers to an unsaturated, aromatic monocyclic ring of 6 carbon members or to an unsaturated, aromatic polycyclic ring of from 10 to 14 carbon members. Examples of such aryl rings include, and are not limited to, phenyl, naphthalenyl or anthracenyl. Preferred aryl groups for the practice of this invention are phenyl and naphthalenyl.

The term "arylalkyl" means an alkyl group substituted with an aryl group (e.g., benzyl, phenethyl). Similarly, the term "arylalkoxy" indicates an alkoxy group substituted with an aryl group (e.g., benzyloxy).

Whenever the term "alkyl" or "aryl" or either of their prefix roots appear in a name of a substituent (e.g., arylalkyl, alkylamino) it shall be interpreted as including those limitations given above for "alkyl" and "aryl." Designated numbers of carbon atoms (e.g., $C_1$-$C_6$) shall refer independently to the number of carbon atoms in an alkyl moiety or to the alkyl portion of a larger substituent in which alkyl appears as its prefix root. For alkyl, and alkoxy substituents the designated number of carbon atoms includes all of the independent member included in the range specified individually and all the combination of ranges within in the range specified. For example $C_{1-6}$ alkyl would include methyl, ethyl, propyl, butyl, pentyl and hexyl individually as well as sub-combinations thereof (e.g. $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc).

"$C_{a-b}$" (where a and b are integers) refers to a radical containing from a to b carbon atoms inclusive. For example, $C_{1-3}$ denotes a radical containing 1, 2 or 3 carbon atoms.

The term "cycloalkyl" refers to saturated or partially unsaturated, moncyclic or polycyclic hydrocarbon rings of from 3 to 20 carbon atom members (preferably from 3 to 14 carbon atom members). Examples of such rings include, and are not limited to, cyclopropyl, cyclobutyl, cyclopentyl, cyclohexyl, cycloheptyl or adamantyl. The term cycloalkyl includes a cycloalkyl ring fused to a benzene ring (benzo fused cycloalkyl), a 5 or 6 membered heteroaryl ring (containing one of O, S or N and, optionally, one additional nitrogen) to form a heteroaryl fused cycloalkyl.

The term "halogen" refers to fluorine, chlorine, bromine and iodine. Substituents that are substituted with multiple halogens are substituted in a manner that provides compounds, which are stable.

"Halogenated alkyl" refers to a saturated branched or straight chain alkyl radical derived by removal of 1 hydrogen atom from the parent alkyl; the parent alkyl chain contains from 1 to 8 carbon atoms with 1 or more hydrogen atoms substituted with halogen atoms up to and including substitution of all hydrogen atoms with halogen. Preferred halogenated alkyl groups include include trifluoromethyl substituted alkyls and perfluorinated alkyls; more preferred fluorinated alkyls include trifluoromethyl.

"Halogenated alkoxy" refers to a radical derived from a halogenated alkyl, radical attached to an oxygen atom with the oxygen atom having one open valence for attachment to a parent structure.

The term "heteroaryl" refers to an aromatic ring of 5 or 6 members wherein the ring consists of carbon atoms and has at least one heteroatom member. Suitable heteroatoms include nitrogen, oxygen or sulfur. In the case of 5 membered rings, the heteroaryl ring contains one member of nitrogen, oxygen or sulfur and, in addition, may contain up to three additional nitrogens. In the case of 6 membered rings, the heteroaryl ring may contain from one to three nitrogen atoms. For the case wherein the 6 membered ring has three nitrogens, at most two nitrogen atoms are adjacent. The term heteroaryl includes a heteroaryl ring fused to a benzene ring (benzo fused heteroaryl), a 5 or 6 membered heteroaryl ring (containing one of O, S or N and, optionally, one additional nitrogen), a 5 to 7 membered cycloalkyl ring or a 5 to 7 membered heterocyclic ring (as defined supra but absent the option of a further fused ring). Examples of heteroaryl groups include, and are not limited to, furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl or pyrazinyl; fused heteroaryl groups include indolyl, isoindolyl, indolinyl, benzofuryl, benzothienyl, indazolyl, benzimidazolyl, benzthiazolyl, benzoxazolyl, benzisoxazolyl, benzothiadiazolyl, benzotriazolyl, quinolizinyl, quinolinyl, isoquinolinyl or quinazolinyl.

The term "heterocyclyl" refers to a nonaromatic cyclic ring of 5 to 10 members in which 1 to 4 members are nitrogen or a nonaromatic cyclic ring of 5 to 10 members in which zero, one or two members are nitrogen and up to two members is oxygen or sulfur; wherein, optionally, the ring contains zero, one or two unsaturated bonds. The term heterocyclyl includes a heterocyclyl ring fused to a benzene ring (benzo fused heterocyclyl), a 5 or 6 membered heteroaryl ring (containing one of O, S or N and, optionally, one additional nitrogen), a 5 to 7 membered cycloalkyl or cycloalkenyl ring, a 5 to 7 membered heterocyclyl ring (of the same definition as above but absent the option of a further fused ring) or fused with the carbon of attachment of a cycloalkyl, cycloalkenyl or heterocyclyl ring to form a spiro moiety. For instant compounds of the invention, the carbon atom ring members that form the heterocyclyl ring are fully saturated. Other compounds of the invention may have a partially saturated heterocyclyl ring. Additionally, heterocyclyl includes a heterocyclic ring bridged to form bicyclic rings. Preferred partially saturated heterocyclyl rings may have from one to two double bonds. Such compounds are not considered to be fully aromatic and are not referred to as heteroaryl compounds. Examples of heterocyclyl groups include, and are not limited to, pyrrolinyl (including 2H-pyrrole, 2-pyrrolinyl or 3-pyrrolinyl), pyrrolidinyl, 2-imidazolinyl, imidazolidinyl, 2-pyrazolinyl, pyrazolidinyl, piperidinyl, morpholinyl, thiomorpholinyl and piperazinyl.

With reference to substituents, the term "independently" means that when more than one of such substituent is possible, such substituents may be the same or different from each other. Therefore, designated numbers of carbon atoms (e.g. $C_{1-8}$) shall refer independently to the number of carbon atoms in an alkyl or cycloalkyl moiety or to the alkyl portion of a larger substituent in which alkyl appears as its prefix root.

The term "oxo" whether used alone or as part of a substituent group refers to an O═ to either a carbon or a sulfur atom. For example, phthalimide and saccharin are examples of compounds with oxo substituents.

Throughout this disclosure, the terminal portion of the designated side chain is described first, followed by the adjacent functionality toward the point of attachment. Thus, for example, a "phenylC$_{1-6}$alkanylaminocarbonylC$_{1-6}$alkyl" substituent refers to a group of the formula

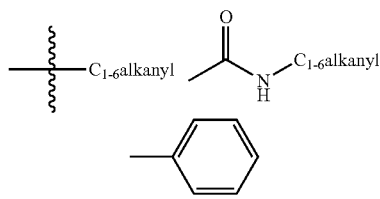

Biology

As used herein, the term "composition" is intended to encompass a product comprising the specified ingredients in the specified amounts, as well as any product which results, directly or indirectly, from combinations of the specified ingredients in the specified amounts.

The term "PK1 receptor agonist" refers to a molecule that selectively activates or increases the activity of the PK1 receptor.

The term "PK1 receptor antagonist" refers to a compound that selectively inhibits or decreases the activity of the PK1 receptor.

The term "PK1 receptor modulator" refers to a compound that either increases or descreases the activity of the PK1 receptor.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

Embodiments of the present invention include compounds of Formula (I) wherein:

a) A$_1$ is hydrogen; aryl; heteroaryl; or C$_{5-8}$cycloalkyl; wherein substituents of A$_1$ other than hydrogen are optionally substituted with one to three substituents independently selected from the group consisting of C$_{1-6}$alkyl, hydroxy(C$_{1-6}$)alkyl, C$_{1-6}$alkoxy, halogen, nitro, halogenated C$_{1-6}$alkyl, halogenated C$_{1-6}$alkoxy, C$_{1-6}$alkylthio, C$_{1-6}$alkoxycarbonyl, amino, C$_{1-6}$alkylamino, di(C$_{1-6}$alkyl) amino, cyano, hydroxy, aminocarbonyl, C$_{1-6}$alkylaminocarbonyl, di(C$_{1-6}$alkyl)aminocarbonyl, C$_{1-6}$alkoxycarbonylamino, C$_{1-6}$alkylcarbonyl, C$_{1-6}$alkylthiocarbonyl, formyl, C$_{1-6}$alkylsulfonyl, C$_{1-6}$alkylsulfonylamino, aminosulfonyl, C$_{1-6}$alkylaminosulfonyl, and di(C$_{1-6}$alkyl) aminosulfonyl;

b) A$_1$ is hydrogen; aryl; heteroaryl; C$_{5-8}$cycloalkyl; or heterocyclyl; provided that A$_1$ is other than piperidin-4-yl, N-t-butoxycarbonyl-piperidin-4-yl, or N-methyl-piperidin-3-yl; and wherein substituents of A$_1$ other than hydrogen are optionally substituted with one to three substituents independently selected from the group consisting of C$_{1-6}$alkyl, hydroxy(C$_{1-6}$)alkyl, C$_{1-6}$alkoxy, halogen, nitro, halogenated C$_{1-6}$alkyl, halogenated C$_{1-6}$alkoxy, C$_{1-6}$alkylthio, C$_{1-6}$alkoxycarbonyl, amino, cyano, hydroxy, aminocarbonyl, C$_{1-6}$alkylaminocarbonyl, di(C$_{1-6}$alkyl)aminocarbonyl, and C$_{1-6}$alkylcarbonyl;

c) A$_1$ is hydrogen; aryl; heteroaryl; C$_{5-8}$cycloalkyl; or heterocyclyl other than piperidinyl; wherein substituents of A$_1$ other than hydrogen are optionally substituted with one to three substituents independently selected from the group consisting of C$_{1-6}$alkyl, hydroxy(C$_{1-6}$)alkyl, C$_{1-6}$alkoxy, halogen, nitro, halogenated C$_{1-6}$alkyl, halogenated C$_{1-6}$alkoxy, C$_{1-6}$alkylthio, C$_{1-6}$alkoxycarbonyl, amino, cyano, hydroxy, aminocarbonyl, C$_{1-6}$alkylaminocarbonyl, di(C$_{1-6}$alkyl)aminocarbonyl, and C$_{1-6}$alkylcarbonyl;

d) A$_1$ is hydrogen, substituted phenyl, benzofuranyl, furanyl, thiazolyl, thiophenyl, or cyclopentyl; wherein substituents of A$_1$ other than hydrogen are optionally substituted and phenyl is substituted with one to two substituents independently selected from the group consisting of C$_{1-4}$alkyl, C$_{1-4}$alkoxy, halogen, nitro, halogenated C$_{1-4}$alkyl, halogenated C$_{1-4}$alkoxy, methylthio, C$_{1-4}$alkoxycarbonyl, amino, cyano, hydroxy, aminocarbonyl, and C$_{1-4}$alkylcarbonyl;

e) A$_1$ is substituted phenyl, benzofuranyl, thiazolyl, or thiophenyl; wherein phenyl is substituted with, and benzofuranyl, thiazolyl, and thiophenyl are optionally substituted with one to two substituents independently selected from the group consisting of C$_{1-4}$alkyl, C$_{1-4}$alkoxy, halogen, nitro, halogenated C$_{1-4}$alkyl, halogenated C$_{1-4}$alkoxy, methylthio, amino, cyano, and C$_{1-4}$alkylcarbonyl;

f) A$_1$ is phenyl or benzofuranyl; wherein phenyl is substituted at either the para-position or meta and para-positions with one to two substituents independently selected from the group consisting of ethyl, methoxy, fluoro, chloro, nitro, difluoromethoxy, and methylthio;

g) L$_1$ is —(CH$_2$)$_r$—, optionally substituted with one to three substituents independently selected from the group consisting of C$_{1-6}$alkyl, C$_{2-6}$alkenyl, C$_{2-6}$alkynyl, and halogen; provided that when A$_1$ is hydrogen, r is greater than or equal to 4;

h) L$_1$ is —(CH$_2$)$_r$—, optionally substituted with a substituent selected from the group consisting of C$_{1-4}$alkyl, C$_{2-4}$alkenyl, and C$_{2-4}$alkynyl, provided that r is 1 to 3 when A$_1$ is other than hydrogen; or r is greater than or equal to 4 when A$_1$ is hydrogen;

i) L$_1$ is —(CH$_2$)$_r$— optionally substituted with a substituent selected from the group consisting of methyl and allyl, provided that r is 1 to 3 when A$_1$ is other than hydrogen;

j) L$_1$ is —CH$_2$— optionally substituted with methyl or allyl;

k) A$_2$ is hydrogen, phenyl, heteroaryl other than unsubstituted pyridin-2-yl, or C$_{3-8}$cycloalkyl; wherein phenyl is optionally substituted at the meta or para positions with, and substituents of A$_2$ other than hydrogen and phenyl are optionally substituted with, one to three substituents independently selected from the group consisting of C$_{1-6}$alkyl, C$_{1-6}$alkoxy, halogen, halogenated C$_{1-6}$alkyl, halogenated C$_{1-6}$alkoxy, aryl(C$_{1-6}$)alkoxy, phenyl, C$_{1-6}$alkylthio, C$_{1-6}$alkoxycarbonyl, amino, cyano, hydroxy, nitro, aminocarbonyl, C$_{1-6}$alkylcarbonylamino, and a non fused C$_{3-6}$cycloalkyloxy; provided that no more than two substituents on A$_2$ are aryl(C$_{1-6}$)alkoxy, phenyl, or a non fused C$_{3-6}$cycloalkyloxy;

provided that when A$_1$ is unsubstituted phenyl and L$_2$ is —X$_1$(CH$_2$)$_2$— wherein X$_1$ is NH, A$_2$ is other than unsubstituted phenyl; phenyl substituted with aryl(C$_{1-6}$) alkoxy or phenyl; or phenyl substituted at the meta position with cyano;

and, further provided that when A$_1$ is unsubstituted phenyl and L$_2$ is —X$_1$(CH$_2$)$_3$— wherein X$_1$ is NH, A$_2$ is other than phenyl substituted with methoxy;

and, provided that when A$_1$ is 3,4-dichloro-phenyl and P is —CH$_2$—, A$_2$ is other than phenyl substituted at the meta position with trifluoromethyl or trifluoromethoxy;

and, further provided that when $A_1$ is 3,4-dichloro-phenyl and P is —$(CH_2)_2$—, $A_2$ is other than 4-methoxy-phenyl;

in addition, when $A_2$ is hydrogen, P is —$(CH_2)_{4-6}$—, and when $A_2$ is other than hydrogen, P is —$(CH_2)_{1-2}$— or —$CH_2X_2$—;

l) $A_2$ is phenyl, heteroaryl other than unsubstituted pyridin-2-yl, or a non fused $C_{3-8}$cycloalkyl; wherein phenyl is optionally substituted at the meta or para positions with, and substituents of $A_2$ other than phenyl are optionally substituted with, one to three substituents independently selected from the group consisting of $C_{1-6}$alkyl, $C_{1-6}$alkoxy, halogen, halogenated $C_{1-6}$alkyl, halogenated $C_{1-6}$alkoxy, $C_{1-6}$alkylthio, $C_{1-6}$alkoxycarbonyl, amino, hydroxy, nitro, aminocarbonyl, $C_{1-6}$alkylcarbonylamino, and a non fused $C_{3-6}$cycloalkyloxy; provided that no more than two substituents on $A_2$ are non fused $C_{3-6}$cycloalkyloxy;

provided that when $A_1$ is unsubstituted phenyl and $L_2$ is —$X_1(CH_2)_2$— wherein $X_1$ is NH, $A_2$ is other than unsubstituted phenyl;

and, further provided that when $A_1$ is unsubstituted phenyl and $L_2$ is —$X_1(CH_2)_3$— wherein $X_1$ is NH, $A_2$ is other than phenyl substituted with methoxy;

and, provided that when $A_1$ is 3,4-dichloro-phenyl, $A_2$ is other than phenyl substituted at the meta position with trifluoromethyl or trifluoromethoxy;

and, further provided that when $A_1$ is 3,4-dichloro-phenyl and P is —$(CH_2)_2$—, $A_2$ is other than 4-methoxy-phenyl;

m) $A_2$ is phenyl, furanyl, pyridin-3-yl, or pyridin-4-yl; wherein phenyl is optionally substituted at the meta or para positions with, and substituents of $A_2$ other than phenyl are optionally substituted with, one to three substituents independently selected from the group consisting of $C_{1-4}$alkyl, $C_{1-4}$alkoxy, halogen, halogenated $C_{1-3}$alkoxy, $C_{1-3}$alkylthio, hydroxy, amino, aminocarbonyl, $C_{1-3}$alkylcarbonylamino, and a non fused $C_{3-6}$cycloalkyloxy; provided that no more than two substituents on $A_2$ are non fused $C_{3-6}$cycloalkyloxy;

provided that when $A_1$ is unsubstituted phenyl and $L_2$ is —$X_1(CH_2)_2$— wherein $X_1$ is NH, $A_2$ is other than unsubstituted phenyl;

and, further provided that when $A_1$ is unsubstituted phenyl and $L_2$ is —$X_1(CH_2)_3$— wherein $X_1$ is NH, $A_2$ is other than phenyl substituted with methoxy;

and, provided that when $A_1$ is 3,4-dichloro-phenyl, $A_2$ is other than phenyl substituted in the meta position with trifluoromethoxy;

n) $A_2$ is phenyl, pyridin-3-yl, or pyridin-4-yl, wherein phenyl is optionally substituted at the meta or para positions with, and substituents on $A_2$ other than phenyl are optionally substituted with, one to two substituents independently selected from the group consisting of methyl, ethyl, methoxy, ethoxy, isopropyloxy, trifluoromethoxy, difluoromethoxy, hydroxy, aminocarbonyl, and methylcarbonylamino;

provided that when $A_1$ is unsubstituted phenyl and $L_2$ is —$X_1(CH_2)_2$— wherein $X_1$ is NH, $A_2$ is other than unsubstituted phenyl;

and, further provided that when $A_1$ is unsubstituted phenyl and $L_2$ is —$X_1(CH_2)_3$— wherein $X_1$ is NH, $A_2$ is other than phenyl substituted with methoxy;

and, provided that when $A_1$ is 3,4-dichloro-phenyl, $A_2$ is other than phenyl substituted in the meta position with trifluoromethoxy;

o) $A_2$ is phenyl substituted at the para position with a substituent selected from the group consisting of methoxy, ethoxy, isopropyloxy, difluoromethoxy, hydroxy, and aminocarbonyl; or $A_2$ is pyridin-3-yl or pyridin-4-yl substituted with methoxy;

p) P is —$CH_2$—;

q) $L_2$ is a bivalent radical selected from the group consisting of
—NH—$C_{5-7}$cycloalkyl-$(CH_2)_{0-2}$—; provided that when $C_{5-7}$cycloalkyl is cyclohexyl, Q is attached at either the 2- or cis-4-position relative to the position of —NH—;
—$X_1$—$C_{2-6}$alkyl-;
—$X_2$—$(CH_2)_{0-4}$—;
—$X_1$—$(CH_2)_{2-3}$—$X_3$—$(CH_2)_{2-3}$—;
—$NH(CH_2)_{1-4}C(=O)$— provided that at least one of $R^b$, $R^c$, or $R^d$ is not hydrogen and m is 0;
—$NHC(=O)$—$(CH_2)_{1-4}$—; and
—$X_1$—$CH(R^x)$—$(CR^xR^y)_{1-5}$—;
wherein $X_1$ is —NH— or a direct bond;
$X_2$ is —CH=CH—; $X_3$ is O, S, NH, or C=O; $R^x$ and $R^y$ are independently H or $C_{1-4}$alkyl; and provided that $L_2$ in any instance does not exceed 7 atoms in length;

r) $L_2$ is a bivalent radical selected from the group consisting of
—NH—$C_{5-6}$cycloalkyl-$(CH_2)_{0-2}$—; provided that when $C_{5-6}$cycloalkyl is cyclohexyl, Q is attached at either the 2- or cis-4-position relative to the position of —NH—;
—NH—$C_{2-6}$alkyl-; and
—NH—(R,R—$CH(CH_3)CH(CH_3)$)—;

s) $L_2$ is a bivalent radical selected from the group consisting of
—NH-cyclohexyl-$(CH_2)_{0-2}$— and Q is attached at either the 2- or cis-4-position relative to the position of —NH—;
—NH—$C_{2-5}$alkyl-; and
—NH—(R,R—$CH(CH_3)CH(CH_3)$)—;

t) $L_2$ is a bivalent radical selected from the group consisting of
—NH-cyclohexyl-$(CH_2)_{0-2}$— and Q is attached at either the 2- or cis-4-position relative to the position of —NH—;
—$NHCH_2CH_2$—; and
—NH—(R,R—$CH(CH_3)CH(CH_3)$)—;

u) m is 0;

v) $R^a$ and $R^d$ are independently hydrogen or $C_{1-6}$alkyl, wherein $C_{1-6}$alkyl is optionally substituted with one to three substituents independently selected from the group consisting of hydroxy, $C_{1-4}$alkoxy, fluoro, amino, $C_{1-4}$alkylamino, di$C_{1-4}$alkylamino, and $C_{1-4}$alkylcarbonyl; or $R^a$ and $R^c$ are taken together with the atoms to which they are attached to form a 5-8 membered monocyclic ring optionally substituted with oxo;

w) $R^a$ and $R^d$ are independently hydrogen or $C_{1-3}$alkyl, wherein $C_{1-3}$alkyl is optionally substituted with one to three substituents independently selected from the group consisting of hydroxy, $C_{1-4}$alkoxy, fluoro, amino, $C_{1-4}$alkylamino, di$C_{1-4}$alkylamino, and $C_{1-4}$alkylcarbonyl; or $R^a$ and $R^c$ are taken together with the atoms to which they are attached to form a 5-8 membered monocyclic ring optionally substituted with oxo;

x) $R^a$ and $R^d$ are independently hydrogen, methyl or ethyl; or $R^a$ and $R^c$ are taken together with the atoms to which they are attached to form a 5-8 membered monocyclic ring optionally substituted with oxo;

y) $R^a$ and $R^d$ are independently hydrogen, methyl or ethyl;

z) $R^b$ is hydrogen, $C_{1-6}$alkyl, $C_{2-6}$alkoxycarbonyl, or cyano; or, $R^b$ and $R^c$ are taken together with the atoms to which they are attached to form a 5-8 membered monocyclic ring, optionally substituted with oxo;

aa) $R^b$ is hydrogen or $C_{1-4}$alkyl; or, $R^b$ and $R^c$ are taken together with the atoms to which they are attached to form a 5-8 membered monocyclic ring, optionally substituted with oxo;
bb) $R^b$ is hydrogen
cc) $R^c$ is hydrogen, $C_{1-10}$alkyl, $C_{2-10}$alkenyl, $C_{3-7}$cycloalkyl, adamantyl, amino, arylcarbonyl, aryl, heteroaryl, or heterocyclyl; wherein $C_{1-10}$alkyl is optionally substituted with one to two substituents independently selected from the group consisting of $C_{1-4}$alkoxy, trifluoromethyl, aryl, heteroaryl, and heterocyclyl; and wherein any aryl- or heteroaryl-containing substituents of $R^c$ are optionally substituted with one to three substituents independently selected from the group consisting of $C_{1-6}$alkyl, $C_{1-6}$alkoxy, halogen, fluorinated $C_{1-6}$alkyl, fluorinated $C_{1-6}$alkoxy, $C_{1-6}$alkylcarbonyl, $C_{1-6}$alkoxycarbonyl, nitro, methylthio, hydroxy, and cyano; or, $R^c$ and $R^d$ are taken together with the atoms to which they are attached to form a 5-8 membered monocyclic ring that optionally includes 1 to 2 O or S heteroatoms within the ring, and said ring is optionally substituted with oxo;
dd) $R^c$ is hydrogen, $C_{1-6}$alkyl, $C_{2-6}$alkenyl, $C_{3-7}$cycloalkyl, adamantyl, heterocyclyl, arylcarbonyl, phenyl, or heteroaryl; wherein $C_{1-6}$alkyl is optionally substituted with one to two substituents independently selected from the group consisting of $C_{1-3}$alkoxy, trifluoromethyl, phenyl, heteroaryl, and heterocyclyl; and wherein any aryl-, phenyl-, or heteroaryl-containing substituents of $R^c$ are optionally substituted with one to three substituents independently selected from the group consisting of $C_{1-6}$alkyl, $C_{1-6}$alkoxy, halogen, fluorinated $C_{1-6}$alkyl, fluorinated $C_{1-6}$alkoxy, $C_{1-6}$alkylcarbonyl, $C_{1-6}$alkoxycarbonyl, nitro, methylthio, hydroxy, and cyano; or, $R^c$ and $R^d$ are taken together with the atoms to which they are attached to form a 5-8 membered monocyclic ring and said ring is optionally substituted with oxo;
ee) $R^c$ is hydrogen, $C_{1-6}$alkyl, $C_{2-6}$alkenyl, $C_{3-7}$cycloalkyl, heterocyclyl, phenylcarbonyl, phenyl, or heteroaryl; wherein $C_{1-6}$alkyl is optionally substituted with one to two substituents independently selected from the group consisting of $C_{1-3}$alkoxy, phenyl, pyridinyl, furanyl, and tetrahydrofuranyl; and wherein any phenyl- or heteroaryl-containing substituents of $R^c$ are optionally substituted with one to two substituents independently selected from the group consisting of $C_{1-6}$alkyl, $C_{1-6}$alkoxy, chloro, fluoro, bromo, fluorinated $C_{1-3}$alkoxy, nitro, methylthio, hydroxy, and cyano; or, $R^c$ and $R^d$ are taken together with the atoms to which they are attached to form a 5-8 membered monocyclic ring;
ff) $R^c$ is hydrogen, $C_{1-4}$alkyl, $C_{2-4}$alkenyl, cyclohexyl, phenylcarbonyl, phenyl, pyrimidinyl, furanyl, benzo[1,3]dioxolyl, or pyridinyl; wherein $C_{1-4}$alkyl is optionally substituted with one to two substituents independently selected from the group consisting of $C_{1-3}$alkoxy, phenyl, pyridinyl, furanyl, and tetrahydrofuranyl; and wherein any phenyl- or heteroaryl-containing substituents of $R^c$ are optionally substituted with one to two substituents independently selected from the group consisting of $C_{1-6}$alkyl, $C_{1-6}$alkoxy, chloro, fluoro, bromo, fluorinated $C_{1-3}$alkoxy, nitro, methylthio, hydroxy, and cyano; or, $R^c$ and $R^d$ are taken together with the atoms to which they are attached to form a 5-8 membered monocyclic ring;
gg) $R^c$ is hydrogen, $C_{1-4}$alkyl, $C_{2-4}$alkenyl, cyclohexyl, phenylcarbonyl, phenyl, pyrimidinyl, furanyl, benzo[1,3]dioxolyl, or pyridinyl; wherein $C_{1-4}$alkyl is optionally substituted with one to two substituents independently selected from the group consisting of methoxy, phenyl, pyridinyl, furanyl, and tetrahydrofuranyl; and wherein any phenyl- or heteroaryl-containing substituents of $R^c$ are optionally substituted with one to two substituents independently selected from the group consisting of $C_{1-3}$alkyl, $C_{1-3}$alkoxy, chloro, fluoro, bromo, trifluoromethoxy, nitro, hydroxy, and cyano; or, $R^c$ and $R^d$ are taken together with the atoms to which they are attached to form a 5-6 membered monocyclic ring;

with the proviso that in any instance, only one ring optionally exists between $R^a$ and $R^b$, $R^b$ and $R^c$, or $R^c$ and $R^d$;
and combinations of a) through gg) above.

One aspect of the present invention is directed to compositions comprising a compound of Formula (Ia):

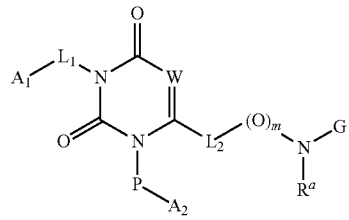

Formula (Ia)

wherein:
$A_1$ is hydrogen; aryl; heteroaryl; $C_{5-8}$cycloalkyl; or heterocyclyl provided that $A_1$ is other than piperidin-4-yl, N-t-butoxycarbonyl-piperidin-4-yl, or N-methyl-piperidin-3-yl; and wherein substituents of $A_1$ other than hydrogen are optionally substituted with one to three substituents independently selected from the group consisting of $C_{1-6}$alkyl, hydroxy($C_{1-6}$)alkyl, $C_{1-6}$alkoxy, halogen, nitro, halogenated $C_{1-6}$alkyl, halogenated $C_{1-6}$alkoxy, $C_{1-6}$alkylthio, $C_{1-6}$alkoxycarbonyl, amino, cyano, hydroxy, aminocarbonyl, $C_{1-6}$alkylaminocarbonyl, di($C_{1-6}$alkyl)aminocarbonyl, and $C_{1-6}$alkylcarbonyl;

$L_1$ is —(CH$_2$)$_r$— optionally substituted with one to three substituents independently selected from the group consisting of $C_{1-6}$alkyl, $C_{2-6}$alkenyl, $C_{2-6}$alkynyl, and halogen; provided that when $A_1$ is hydrogen, r is greater than or equal to 4;

r is an integer of 1 to 5;

$A_2$ is hydrogen, phenyl, heteroaryl other than unsubstituted pyridin-2-yl, or $C_{3-8}$cycloalkyl; wherein phenyl is optionally substituted at the meta or para positions with, and substituents of $A_2$ other than hydrogen and phenyl are optionally substituted with, one to three substituents independently selected from the group consisting of $C_{1-6}$alkyl, $C_{1-6}$alkoxy, halogen, halogenated $C_{1-6}$alkyl, halogenated $C_{1-6}$alkoxy, aryl($C_{1-6}$)alkoxy, phenyl, $C_{1-6}$alkylthio, $C_{1-6}$alkoxycarbonyl, amino, cyano, hydroxy, nitro, aminocarbonyl, $C_{1-6}$alkylcarbonylamino, and a non fused $C_{3-6}$cycloalkyloxy; provided that no more than two substituents on $A_2$ are aryl($C_{1-6}$)alkoxy, phenyl, or a non fused $C_{3-6}$cycloalkyloxy;
  provided that when $A_1$ is unsubstituted phenyl and $L_2$ is —X$_1$(CH$_2$)$_2$— wherein X$_1$ is NH, $A_2$ is other than unsubstituted phenyl; phenyl substituted with aryl($C_{1-6}$) alkoxy or phenyl; or phenyl substituted at the meta position with cyano;
  and, further provided that when $A_1$ is unsubstituted phenyl and $L_2$ is —X$_1$(CH$_2$)$_3$— wherein X$_1$ is NH, $A_2$ is other than phenyl substituted with methoxy;
  and, provided that when $A_1$ is 3,4-dichloro-phenyl and P is —CH$_2$—, $A_2$ is other than phenyl substituted in the meta position with trifluoromethyl or trifluoromethoxy;

and, further provided that when $A_1$ is 3,4-dichloro-phenyl and P is —$(CH_2)_2$—, $A_2$ is other than 4-methoxy-phenyl;

in addition, when $A_2$ is hydrogen, P is —$(CH_2)_{4-6}$—, and when $A_2$ is other than hydrogen, P is —$(CH_2)_{1-2}$— or —$CH_2X_2$—;

W is N or CH;

$L_2$ is a bivalent radical selected from the group consisting of
—NH—$C_{5-7}$cycloalkyl-$(CH_2)_{0-2}$—; provided that when $C_{5-7}$cycloalkyl is cyclohexyl, Q is attached at either the 2- or cis-4-position relative to the position of —NH—;
—$X_1$—$C_{2-6}$alkyl-;
—$X_2$—$(CH_2)_{0-4}$—;
—$X_1$—$(CH_2)_{2-3}$—$X_3$—$(CH_2)_{2-3}$—;
$NH(CH_2)_{1-4}C(=O)$— provided that at least one of $R^b$, $R^c$, or $R^d$ is not hydrogen and m is 0;
—NHC(=O)—$(CH_2)_{1-4}$—; and
—$X_1$—$CH(R^x)$—$(CR^xR^y)_{1-5}$—;
wherein $X_1$ is —NH— or a direct bond;
$X_2$ is —CH=CH—; $X_3$ is O, S, NH, or C=O; $R^x$ and $R^y$ are independently H or $C_{1-4}$alkyl;

and provided that $L_2$ in any instance does not exceed 7 atoms in length;

m is 0 or 1;

G is —$C(=NR^b)NR^cR^d$;

$R^a$ and $R^d$ are independently hydrogen or $C_{1-6}$alkyl, wherein $C_{1-6}$alkyl is optionally substituted with one to three substituents independently selected from the group consisting of hydroxy, $C_{1-4}$alkoxy, fluoro, amino, $C_{1-4}$alkylamino, di$C_{1-4}$alkylamino, and $C_{1-4}$alkylcarbonyl; or $R^a$ and $R^c$ are taken together with the atoms to which they are attached to form a 5-8 membered monocyclic ring optionally substituted with oxo;

$R^b$ is hydrogen, $C_{1-6}$alkyl, $C_{2-6}$alkoxycarbonyl, or cyano; or, $R^b$ and $R^c$ are taken together with the atoms to which they are attached to form a 5-8 membered monocyclic ring optionally substituted with oxo;

$R^c$ is hydrogen, $C_{1-10}$alkyl, $C_{2-10}$alkenyl, $C_{3-7}$cycloalkyl, adamantyl, amino, arylcarbonyl, aryl, heteroaryl, or heterocyclyl; wherein $C_{1-10}$alkyl is optionally substituted with one to two substituents independently selected from the group consisting of $C_{1-4}$alkoxy, trifluoromethyl, aryl, heteroaryl, and heterocyclyl; and wherein any aryl- or heteroaryl-containing substituents of $R^c$ are optionally substituted with one to three substituents independently selected from the group consisting of $C_{1-6}$alkyl, $C_{1-6}$alkoxy, halogen, fluorinated $C_{1-6}$alkyl, fluorinated $C_{1-6}$alkoxy, $C_{1-6}$alkylcarbonyl, $C_{1-6}$alkoxycarbonyl, nitro, methylthio, hydroxy, and cyano; or, $R^c$ and $R^d$ are taken together with the atoms to which they are attached to form a 5-8 membered monocyclic ring that optionally includes 1 to 2 O or S heteroatoms within the ring, and said ring is optionally substituted with oxo;

with the proviso that in any instance, only one ring optionally exists between $R^a$ and $R^b$, $R^b$ and $R^c$, or $R^c$ and $R^d$;

and enantiomers, diastereomers, tautomers, solvates, and pharmaceutically acceptable salts thereof.

A further aspect of the present invention is directed to a compound of Formula Ia wherein:

$A_1$ is hydrogen; aryl; heteroaryl; $C_{5-8}$cycloalkyl; or heterocyclyl other than piperidinyl; wherein substituents of $A_1$ other than hydrogen are optionally substituted with one to three substituents independently selected from the group consisting of $C_{1-6}$alkyl, hydroxy($C_{1-10}$alkyl), $C_{1-6}$alkoxy, halogen, nitro, halogenated $C_{1-6}$alkyl, halogenated $C_{1-6}$alkoxy, $C_{1-6}$alkylthio, $C_{1-6}$alkoxycarbonyl, amino, cyano, hydroxy, aminocarbonyl, $C_{1-6}$alkylaminocarbonyl, di($C_{1-6}$alkyl)aminocarbonyl, and $C_{1-6}$alkylcarbonyl;

$L_1$ is —$(CH_2)_r$— optionally substituted with a substituent selected from the group consisting of $C_{1-4}$alkyl, $C_{2-4}$alkenyl, and $C_{2-4}$alkynyl; provided that r is 1 to 3 when $A_1$ is other than hydrogen; or r is 4 or 5 when $A_1$ is hydrogen;

$A_2$ is phenyl, furanyl, pyridin-3-yl, or pyridin-4-yl; wherein phenyl is optionally substituted at the meta or para positions with, and substituents of $A_2$ other than phenyl are optionally substituted with, one to three substituents independently selected from the group consisting of $C_{1-4}$alkyl, $C_{1-4}$alkoxy, halogen, halogenated $C_{1-3}$alkoxy, $C_{1-3}$alkylthio, hydroxy, amino, aminocarbonyl, $C_{1-3}$alkylcarbonylamino, and a non fused $C_{3-6}$cycloalkyloxy; provided that no more than two substituents on $A_2$ are a non fused $C_{3-6}$cycloalkyloxy;

provided that when $A_1$ is unsubstituted phenyl and $L_2$ is —$X_1(CH_2)_2$— wherein $X_1$ is NH, $A_2$ is other than unsubstituted phenyl;

and, further provided that when $A_1$ is unsubstituted phenyl and $L_2$ is —$X_1(CH_2)_3$— wherein $X_1$ is NH, $A_2$ is other than phenyl substituted with methoxy;

and, provided that when $A_1$ is 3,4-dichloro-phenyl, $A_2$ is other than phenyl substituted in the meta position with trifluoromethoxy;

P is —$CH_2$—;

W is N or CH;

$L_2$ is a bivalent radical selected from the group consisting of —NH—$C_{5-6}$cycloalkyl-$(CH_2)_{0-2}$—; provided that when $C_{5-6}$cycloalkyl is cyclohexyl, Q is attached at either the 2- or cis-4-position relative to the position of —NH—;
—NH—$C_{2-6}$alkyl-; and
—NH—(R,R—$CH(CH_3)CH(CH_3)$)—;

m is 0 or 1;

G is —$C(=NR^b)NR^cR^d$;

$R^a$ and $R^d$ are independently hydrogen or $C_{1-3}$alkyl, wherein $C_{1-3}$alkyl is optionally substituted with one to three substituents independently selected from the group consisting of hydroxy, $C_{1-4}$alkoxy, fluoro, amino, $C_{1-4}$alkylamino, di$C_{1-4}$alkylamino, and $C_{1-4}$alkylcarbonyl; or $R^a$ and $R^c$ are taken together with the atoms to which they are attached to form a 5-8 membered monocyclic ring optionally substituted with oxo;

$R^b$ is hydrogen or $C_{1-4}$alkyl; or, $R^b$ and $R^c$ are taken together with the atoms to which they are attached to form a 5-8 membered monocyclic ring, optionally substituted with oxo;

$R^c$ is hydrogen, $C_{1-6}$alkyl, $C_{2-6}$alkenyl, $C_{3-7}$cycloalkyl, adamantyl, heterocyclyl, arylcarbonyl, phenyl, or heteroaryl; wherein $C_{1-6}$alkyl is optionally substituted with one to two substituents independently selected from the group consisting of $C_{1-3}$alkoxy, trifluoromethyl, phenyl, heteroaryl, and heterocyclyl; and wherein any aryl-, phenyl-, or heteroaryl-containing substituents of $R^c$ are optionally substituted with one to three substituents independently selected from the group consisting of $C_{1-6}$alkyl, $C_{1-6}$alkoxy, halogen, fluorinated $C_{1-6}$alkyl, fluorinated $C_{1-6}$alkoxy, $C_{1-6}$alkylcarbonyl, $C_{1-6}$alkoxycarbonyl, nitro, methylthio, hydroxy, and cyano; or, $R^c$ and $R^d$ are taken together with the atoms to which they are attached to form a 5 membered monocyclic ring and said ring is optionally substituted with oxo;

with the proviso that in any instance, only one ring optionally exists between $R^a$ and $R^b$, $R^b$ and $R^c$, or $R^c$ and $R^d$;

and enantiomers, diastereomers, tautomers, solvates, and pharmaceutically acceptable salts thereof.

A further aspect of the present invention is directed to a compound of Formula Ia wherein:

$A_1$ is substituted phenyl, benzofuranyl, thiazolyl, or thiophenyl; wherein phenyl is substituted with, and benzofuranyl, thiazolyl, and thiophenyl are optionally substituted with, one to two substituents independently selected from the group consisting of $C_{1-4}$alkyl, $C_{1-4}$alkoxy, halogen, nitro, halogenated $C_{1-4}$alkyl, halogenated $C_{1-4}$alkoxy, methylthio, amino, cyano, and $C_{1-4}$alkylcarbonyl;

$L_1$ is —$(CH_2)_r$— optionally substituted with a substituent selected from the group consisting of methyl and allyl, and r is 1 to 3;

$A_2$ is phenyl, pyridin-3-yl, or pyridin-4-yl, wherein phenyl is optionally substituted at the meta or para positions with, and substituents of $A_2$ other than phenyl are optionally substituted with one to two substituents independently selected from the group consisting of methyl, ethyl, methoxy, ethoxy, isopropyloxy, trifluoromethoxy, difluoromethoxy, hydroxy, aminocarbonyl, and methylcarbonylamino; provided that when $A_1$ is 3,4-dichloro-phenyl, $A_2$ is other than phenyl substituted in the meta position with trifluoromethoxy;

P is —$CH_2$—;

W is N or CH;

$L_2$ is a bivalent radical selected from the group consisting of
—NH-cyclohexyl-$(CH_2)_{0-2}$— and Q is attached at either the 2- or cis-4-position relative to the position of —NH—;
—NH—$C_{2-5}$alkyl-; and
—NH—(R,R—CH(CH$_3$)CH(CH$_3$))—;

m is 0;

G is —C(=NR$^b$)NR$^c$R$^d$;

R$^a$ and R$^d$ are independently hydrogen, methyl or ethyl; or R$^a$ and R$^c$ are taken together with the atoms to which they are attached to form a 5-8 membered monocyclic ring optionally substituted with oxo;

R$^b$ is hydrogen;

R$^c$ is hydrogen, $C_{1-6}$alkyl, $C_{2-6}$alkenyl, $C_{3-7}$cycloalkyl, heterocyclyl, phenylcarbonyl, phenyl, or heteroaryl; wherein $C_{1-6}$alkyl is optionally substituted with one to two substituents independently selected from the group consisting of $C_{1-3}$alkoxy, phenyl, pyridinyl, furanyl, and tetrahydrofuranyl; and wherein any phenyl- or heteroaryl-containing substituents of R$^c$ are optionally substituted with one to two substituents independently selected from the group consisting of $C_{1-6}$alkyl, $C_{1-6}$alkoxy, chloro, fluoro, bromo, fluorinated $C_{1-3}$alkoxy, nitro, methylthio, hydroxy, and cyano; or, R$^c$ and R$^d$ are taken together with the atoms to which they are attached to form a 5-8 membered monocyclic ring;

with the proviso that in any instance, only one ring optionally exists between R$^a$ and R$^b$, R$^b$ and R$^c$, or R$^c$ and R$^d$;

and enantiomers, diastereomers, tautomers, solvates, and pharmaceutically acceptable salts thereof.

Another aspect of the present invention is directed to a compound of Formula Ia wherein:

$A_1$ is phenyl or benzofuranyl; wherein phenyl is substituted at either the 4-position or 3 and 4-positions with one to two substituents independently selected from the group consisting of ethyl, methoxy, fluoro, chloro, nitro, difluoromethoxy, and methylthio;

$L_1$ is —$CH_2$— optionally substituted with methyl or allyl;

$A_2$ is phenyl substituted at the para position with a substituent selected from the group consisting of methoxy, ethoxy, isopropyloxy, difluoromethoxy, hydroxy, and aminocarbonyl; or $A_2$ is pyridin-3-yl or pyridin-4-yl substituted with methoxy;

P is —$CH_2$—;

W is N or CH;

$L_2$ is a bivalent radical selected from the group consisting of
—NH-cyclohexyl-$(CH_2)_{0-2}$— and Q is attached at either the 2- or cis-4-position relative to the position of —NH—;
—NHCH$_2$CH$_2$—; and
—NH—(R,R—CH(CH$_3$)CH(CH$_3$))—;

m is 0;

G is —C(=NR$^b$)NR$^c$R$^d$;

R$^a$ and R$^d$ are independently hydrogen, methyl or ethyl;

R$^b$ is hydrogen;

R$^c$ is hydrogen, $C_{1-4}$alkyl, $C_{2-4}$alkenyl, cyclohexyl, phenylcarbonyl, phenyl, pyrimidinyl, furanyl, benzo[1,3]dioxolyl, or pyridinyl; wherein $C_{1-4}$alkyl is optionally substituted with one to two substituents independently selected from the group consisting of $C_{1-3}$alkoxy, phenyl, pyridinyl, furanyl, and tetrahydrofuranyl; and wherein any phenyl- or heteroaryl-containing substituents of R$^c$ are optionally substituted with one to two substituents independently selected from the group consisting of $C_{1-6}$alkyl, $C_{1-6}$alkoxy, chloro, fluoro, bromo, fluorinated $C_{1-3}$alkoxy, nitro, methylthio, hydroxy, and cyano; or, R$^c$ and R$^d$ are taken together with the atoms to which they are attached to form a 5-8 membered monocyclic ring;

and enantiomers, diastereomers, tautomers, solvates, and pharmaceutically acceptable salts thereof.

Another aspect of the present invention is directed to compounds of Formula (I) in Table 1 wherein $A_1$, $L_1$, D, W, $L_2$, and Q are as defined in the present invention.

TABLE 1

| Cpd # | $A_1$ | $L_1$ | D | W | $L_2$ | Q |
|---|---|---|---|---|---|---|
| 1 | phenyl | —CH$_2$— | —CH$_2$-(4-fluoro-phenyl) | N | —NH(CH$_2$)$_2$— | —NHC(=NH)NH$_2$ |
| 2 | phenyl | —CH$_2$— | —CH$_2$-(4-methoxy-phenyl) | N | —NH(CH$_2$)$_2$— | —NHC(=NH)NH$_2$ |
| 3 | phenyl | —CH$_2$— | —CH$_2$-(4-methylcarboxy-phenyl) | N | —NH(CH$_2$)$_2$— | —NHC(=NH)NH$_2$ |
| 4 | phenyl | —(CH$_2$)$_2$— | —CH$_2$-(4-methoxy-phenyl) | N | —NH(CH$_2$)$_2$— | —NHC(=NH)NH$_2$, |
| 5 | H | —(CH$_2$)$_4$— | —CH$_2$-(4-methoxy-phenyl) | N | —NH(CH$_2$)$_2$— | —NHC(=NH)NH$_2$ |
| 6 | furan-2-yl | —CH$_2$— | —CH$_2$-(4-methoxy-phenyl) | N | —NH(CH$_2$)$_2$— | —NHC(=NH)NH$_2$ |

TABLE 1-continued

| Cpd # | $A_1$ | $L_1$ | D | W | $L_2$ | Q |
|---|---|---|---|---|---|---|
| 7 | phenyl | —$CH_2$— | —$CH_2$-(3-trifluoromethyl-phenyl) | N | —NH$(CH_2)_2$— | —NHC(=NH)$NH_2$ |
| 8 | phenyl | —$CH_2$— | —$CH_2$-(4-t-butyl-phenyl) | N | —NH$(CH_2)_2$— | —NHC(=NH)$NH_2$ |
| 9 | phenyl | —$CH_2$— | —$CH_2$-(4-nitro-phenyl) | N | —NH$(CH_2)_2$— | —NHC(=NH)$NH_2$ |
| 10 | phenyl | —$CH_2$— | —$CH_2$-(4-methoxy-phenyl) | N | —NH$(CH_2)_2$— | —ONHC(=NH)$NH_2$ |
| 11 | phenyl | —$CH_2$— | —$CH_2$-pyridin-4-yl | N | —NH$(CH_2)_2$— | —NHC(=NH)$NH_2$ |
| 12 | phenyl | —$CH_2$— | —$CH_2$-(4-ethoxy-phenyl) | N | —NH$(CH_2)_2$— | —NHC(=NH)$NH_2$ |
| 13 | phenyl | —$CH_2$— | —$CH_2$-(4-difluoromethoxy-phenyl) | N | —NH$(CH_2)_2$— | —NHC(=NH)$NH_2$ |
| 14 | phenyl | —$CH_2$— | —$CH_2$-(4-n-butyl-phenyl) | N | —NH$(CH_2)_2$— | —NHC(=NH)$NH_2$ |
| 15 | phenyl | —$CH_2$— | —$CH_2$-(4-trifluoromethyl-phenyl) | N | —NH$(CH_2)_2$— | —NHC(=NH)$NH_2$ |
| 16 | 2-fluoro-phenyl | —$CH_2$— | —$CH_2$-(4-methoxy-phenyl) | N | —NH$(CH_2)_2$— | —NHC(=NH)$NH_2$ |
| 17 | 4-fluoro-phenyl | —$CH_2$— | —$CH_2$-(4-methoxy-phenyl) | N | —NH$(CH_2)_2$— | —NHC(=NH)$NH_2$ |
| 18 | 3,4-dichloro-phenyl | —$CH_2$— | —$CH_2$-(4-methoxy-phenyl) | N | —NH$(CH_2)_2$— | —NHC(=NH)$NH_2$ |
| 19 | phenyl | —$CH_2$— | —$CH_2$-(4-trifluoromethoxy-phenyl) | N | —NH$(CH_2)_2$— | —NHC(=NH)$NH_2$ |
| 20 | 3-methoxy-phenyl | —$CH_2$— | —$CH_2$-(4-methoxy-phenyl) | N | —NH$(CH_2)_2$— | —NHC(=NH)$NH_2$ |
| 21 | 2-methoxy-phenyl | —$CH_2$— | —$CH_2$-(4-methoxy-phenyl) | N | —NH$(CH_2)_2$— | —NHC(=NH)$NH_2$ |
| 22 | phenyl | —$CH_2$— | —$CH_2$-(4-aminocarbonyl-phenyl) | N | —NH$(CH_2)_2$— | —NHC(=NH)$NH_2$ |
| 23 | phenyl | —$CH_2$— | —$CH_2$-(4-methylcarboxyl amino-phenyl) | N | —NH$(CH_2)_2$— | —NHC(=NH)$NH_2$ |
| 24 | 4-fluoro-phenyl | —$CH_2$— | —$CH_2$-(4-ethoxy-phenyl) | N | —NH$(CH_2)_2$— | —NHC(=NH)$NH_2$ |
| 25 | phenyl | —(R,R—CH($CH_3$)CH($CH_3$))— | —$CH_2$-(4-methoxy-phenyl) | N | —NH$(CH_2)_2$— | —NHC(=NH)$NH_2$ |
| 26 | phenyl | —(R,R—CH($CH_3$)CH($CH_3$))— | —$CH_2$-(4-methoxy-phenyl) | N | —NH$(CH_2)_2$— | —NHC(=NH)$NH_2$ |
| 27 | 3,4-dichloro-phenyl | —$CH_2$— | —$CH_2$-(4-methoxy-phenyl) | N | —NH$(CH_2)_2$— | —ONHC(=NH)$NH_2$ |
| 28 | 3,4-dichloro-phenyl | —$CH_2$— | —$CH_2$-(4-methoxy-phenyl) | N | —NH$(CH_2)_2$— | —NHC(=N—CN)$NH_2$ |
| 29 | 3,4-dichloro-phenyl | —$CH_2$— | —$CH_2$-(4-ethoxy-phenyl) | N | —NH$(CH_2)_2$— | —NHC(=NH)$NH_2$ |
| 30 | 4-chloro-phenyl | —$CH_2$— | —$CH_2$-(4-methoxy-phenyl) | N | —NH$(CH_2)_2$— | —NHC(=NH)$NH_2$ |
| 31 | 4-methoxy-phenyl | —$CH_2$— | —$CH_2$-(4-methoxy-phenyl) | N | —NH$(CH_2)_2$— | —NHC(=NH)$NH_2$ |
| 32 | 3,4-dichloro-phenyl | —$CH_2$— | —$CH_2$-(4-methoxy-phenyl) | N | —NH$(CH_2)_4$— | —NHC(=NH)$NH_2$ |
| 33 | 4-fluoro-phenyl | —$CH_2$— | —$(CH_2)_2$-(4-methoxy-phenyl) | N | —NH$(CH_2)_2$— | —NHC(=NH)$NH_2$ |
| 34 | 3,4-dichloro-phenyl | —$CH_2$— | —$CH_2$-(4-n-propyl-phenyl) | N | —NH$(CH_2)_2$— | —NHC(=NH)$NH_2$ |
| 35 | 3,4-dichloro-phenyl | —$CH_2$— | —$CH_2$-(4-i-propyl-phenyl) | N | —NH$(CH_2)_2$— | —NHC(=NH)$NH_2$ |
| 36 | 3,4-dichloro-phenyl | —$CH_2$— | —$CH_2$-(4-cyclopentyloxy-phenyl) | N | —NH$(CH_2)_2$— | —NHC(=NH)$NH_2$ |
| 37 | 3,4-dichloro-phenyl | —$CH_2$— | —$CH_2$-(4-methylthio-phenyl) | N | —NH$(CH_2)_2$— | —NHC(=NH)$NH_2$ |
| 38 | 3,4-dichloro-phenyl | —$CH_2$— | —$CH_2$-(4-ethyl-phenyl) | N | —NH$(CH_2)_2$— | —NHC(=NH)$NH_2$ |
| 39 | 3-chloro-phenyl | —$CH_2$— | —$CH_2$-(4-methoxy-phenyl) | N | —NH$(CH_2)_2$— | —NHC(=NH)$NH_2$ |
| 40 | 3,4-dichloro-phenyl | —$CH_2$— | —$CH_2$-(4-trifluoromethoxy-phenyl) | N | —NH$(CH_2)_2$— | —NHC(=NH)$NH_2$ |

TABLE 1-continued

| Cpd # | A₁ | L₁ | D | W | L₂ | Q |
|---|---|---|---|---|---|---|
| 41 | 3,4-dichloro-phenyl | —CH₂— | —CH₂-(4-difluoromethoxy-phenyl) | N | —NH(CH₂)₂— | —NHC(=NH)NH₂ |
| 42 | 3,4-dichloro-phenyl | —CH₂— | —CH₂-(4-methoxy-phenyl) | N | cis-racemic-1,2-cyclohexyl | —NHC(=NH)NH₂ |
| 43 | 3,4-dichloro-phenyl | —CH₂— | —CH₂-(4-methoxy-phenyl) | N | trans (1S,2S)-cyclohexyl- | —NHC(=NH)NH₂ |
| 44 | 3,4-dichloro-phenyl | —CH₂— | —CH₂-(4-methoxy-phenyl) | N | —NH(CH₂)₂— | —NHC(=NH)NH₂ |
| 45 | 4-methylthio-phenyl | —CH₂— | —CH₂-(4-methoxy-phenyl) | N | —NH(CH₂)₂— | —NHC(=NH)NH₂ |
| 46 | 4-ethyl-phenyl | —CH₂— | —CH₂-(4-methoxy-phenyl) | N | —NH(CH₂)₂— | —NHC(=NH)NH₂ |
| 47 | 3,4-dichloro-phenyl | —CH₂— | —CH₂-(4-methoxy-phenyl) | N | trans(1R,2R)-cyclohexyl- | —NHC(=NH)NH₂ |
| 48 | 3,4-dichloro-phenyl | —CH₂— | —CH₂-(4-methoxy-phenyl) | N | —NH(CH₂)₂— | —NH(3,5-dihydro-imidazol-4-on-2-yl) |
| 49 | 3,4-dichloro-phenyl | —CH₂— | —CH₂-(4-methoxy-phenyl) | N | —NH(CH₂)₂— | —NH(4,5-dihydro-1H-imidazol-2-yl) |
| 50 | 3,4-dichloro-phenyl | —CH₂— | —CH₂-(4-methylcarbonyl amino-phenyl) | N | —NH(CH₂)₂— | —NHC(=NH)NH₂ |
| 51 | 3,4-dichloro-phenyl | —CH₂— | —CH₂-(4-aminocarbonyl-phenyl) | N | —NH(CH₂)₂— | —NHC(=NH)NH₂ |
| 52 | 3,4-dichloro-phenyl | —CH₂— | —CH₂-(3-ethoxy-phenyl) | N | —NH(CH₂)₂— | —NHC(=NH)NH₂ |
| 53 | 3,4-dichloro-phenyl | —CH₂— | —CH₂-(4-ethoxy-phenyl) | N | —NH(CH₂)₂— | —NHC(=NH)NH-ethyl |
| 54 | 3,4-dichloro-phenyl | —CH₂— | —CH₂-(4-methoxy-phenyl) | N | —NH(CH₂)₂— | —NHC(=NH)NH-propyl |
| 55 | 3,4-dichloro-phenyl | —CH₂— | —CH₂-(4-methoxy-phenyl) | N | pyrrolindin-1-yl | 3-NHC(=NH)NH₂ |
| 56 | 4-chloro-phenyl | —CH₂— | —CH₂-(4-methoxy-phenyl) | N | -trans (1R,2R)-cyclohexyl- | —NHC(=NH)NH₂ |
| 57 | 3,4-dichloro-phenyl | —CH₂— | —CH₂-(3-difluoromethoxy-phenyl) | N | —NH(CH₂)₂— | —NHC(=NH)NH₂ |
| 58 | 3,4-dichloro-phenyl | —CH₂— | —CH₂-(4-methoxy-phenyl) | N | —NH(CH₂)₂— | —NHC(=NH)NH(i-propyl) |
| 59 | 3,4-dichloro-phenyl | —CH₂— | —CH₂-(4-methoxy-phenyl) | N | —NH(CH₂)₂— | —N(ethyl)C(=NH)NH₂ |
| 60 | 3,4-dichloro-phenyl | —CH₂— | —CH₂-(4-methoxy-phenyl) | N | —NH(CH₂)₂— | 2-imino-imidazolid-1-yl |
| 61 | 3,4-dichloro-phenyl | —CH₂— | —CH₂-(4-methoxy-phenyl) | N | —NH(CH₂)₂— | —NHC(=NH)NH(n-butyl) |
| 62 | 3,4-dichloro-phenyl | —CH₂— | —CH₂-(4-methoxy-phenyl) | N | —NH(CH₂)₂— | —NHC(=NH)NH(cyclohexyl) |
| 63 | 3,4-dichloro-phenyl | —CH₂— | —CH₂-(4-methoxy-phenyl) | N | —NH(CH₂)₂— | —NHC(=NH)NH(benzyl) |
| 64 | 3,4-dichloro-phenyl | —CH₂— | —CH₂-(4-methoxy-phenyl) | N | —NH(CH₂)₂— | —NHC(=NH)NH(tetrahydrofuran-2-ylmethyl) |
| 65 | 3,4-dichloro-phenyl | —CH₂— | —CH₂-(4-methoxy-phenyl) | N | —NH(CH₂)₂— | —NHC(=NH)NH(phenylethyl) |
| 66 | 3,4-dichloro-phenyl | —CH₂— | —CH₂-(4-methoxy-phenyl) | N | —NH(CH₂)₂— | —NHC(=NH)NH(furan-2-ylmethyl) |
| 67 | 3,4-dichloro-phenyl | —CH₂— | —CH₂-(4-methoxy-phenyl) | N | —NH(CH₂)₂— | —NHC(=NH)NH(2-methoxy-ethyl) |
| 68 | 3,4-dichloro-phenyl | —CH₂— | —CH₂-(4-methoxy-phenyl) | N | —NH(CH₂)₃— | —NHC(=NH)NH₂ |
| 69 | 3,4-dichloro-phenyl | —CH₂— | —(CH₂)₆—H | N | —NH(CH₂)₃— | —NHC(=NH)NH₂ |
| 70 | 3,4-dichloro-phenyl | —CH₂— | —CH₂-(4-methoxy-phenyl) | N | —NH(CH₂)₂— | —NHC(=NH)NH(allyl) |
| 71 | 3,4-dichloro-phenyl | —CH₂— | —CH₂-(4-methoxy-phenyl) | N | —NH(CH₂)₂— | —NHC(=NH)NH(phenyl) |
| 72 | 3,4-dichloro-phenyl | —CH₂— | —CH₂-(4-methoxy-phenyl) | N | —NH(CH₂)₂— | —NHC(=NH)NH(4-methoxy-phenyl) |
| 73 | 3,4-dichloro-phenyl | —CH₂— | —CH₂-(4-methoxy-phenyl) | N | —NH(CH₂)₂— | —NHC(=NH)NH(4-chloro-phenyl) |
| 74 | 3,4-dichloro-phenyl | —CH₂— | —CH₂-(4-methoxy-phenyl) | N | —NH(CH₂)₂— | —NHC(=NH)NH(4-trifluoromethyl-phenyl) |
| 75 | 3,4-dichloro-phenyl | —CH₂— | —CH₂-(4-methoxy-phenyl) | N | —NH(CH₂)₂— | —NHC(=NH)NH(pyridin-3-yl) |

TABLE 1-continued

| Cpd # | A₁ | L₁ | D | W | L₂ | Q |
|---|---|---|---|---|---|---|
| 76 | 3,4-dichloro-phenyl | —CH₂— | —CH₂-(4-methoxy-phenyl) | N | —NH(CH₂)₂— | —NHC(=NH)NH(4-methylcarbonyl-phenyl) |
| 77 | furan-3-yl | —CH₂— | —CH₂-(4-methoxy-phenyl) | N | —NH(CH₂)₂— | —NHC(=NH)NH₂ |
| 78 | thiophen-2-yl | —CH₂— | —CH₂-(4-methoxy-phenyl) | N | —NH(CH₂)₂— | —NHC(=NH)NH₂ |
| 79 | 4-methoxy-phenyl | R,S-mixture-CH(CH₃)— | —CH₂-(4-methoxy-phenyl) | N | —NH(CH₂)₂— | —NHC(=NH)NH₂ |
| 80 | 4-difluoromethoxy-phenyl | —CH₂— | —CH₂-(4-methoxy-phenyl) | N | —NH(CH₂)₂— | —NHC(=NH)NH₂ |
| 81 | phenyl | —CH₂— | —CH₂-(4-methoxy-phenyl) | C | —NH(CH₂)₂— | —NHC(=NH)NH₂ |
| 82 | 4-methoxy-phenyl | R,S-mixture-CH(allyl)- | —CH₂-(4-methoxy-phenyl) | N | —NH(CH₂)₂— | —NHC(=NH)NH₂ |
| 83 | 4-chloro-phenyl | R,S-mixture-CH(allyl)- | —CH₂-(4-methoxy-phenyl) | N | —NH(CH₂)₂— | —NHC(=NH)NH₂ |
| 84 | 4-methoxy-phenyl | —CH₂— | —CH₂-(4-methoxy-phenyl) | C | —NH(CH₂)₂— | —NHC(=NH)NH₂ |
| 85 | 4-methoxy-phenyl | —CH₂— | —CH₂-(6-methoxy-pyridin-3-yl) | N | —NH(CH₂)₂— | —NHC(=NH)NH₂ |
| 86 | 4-methoxy-phenyl | —CH₂— | —CH₂-(4-methoxy-cyclohexyl) | N | —NH(CH₂)₂— | —NHC(=NH)NH₂ |
| 87 | 4-fluoro-phenyl | —CH₂— | —CH₂-(4-nitro-phenyl) | N | —NH(CH₂)₂— | —NHC(=NH)NH₂ |
| 88 | 4-fluoro-phenyl | —CH₂— | —CH₂-(4-methoxy-phenyl) | N | —NH(CH₂)₂— | —NHC(=NH)NH(2-(morpholin-4-yl)-eth-1-yl) |
| 89 | 4-fluoro-phenyl | —CH₂— | —CH₂-(4-methoxy-phenyl) | N | —NH(CH₂)₂— | —NHC(=NH)NH(3-(morpholin-4-yl)-prop-1-yl) |
| 90 | 4-fluoro-phenyl | —CH₂— | —CH₂-(4-methoxy-phenyl) | N | —NH(CH₂)₂— | —NHC(=NH)NH(4-cyano-phenyl) |
| 91 | 4-fluoro-phenyl | —CH₂— | —CH₂-(4-methoxy-phenyl) | N | —NH(CH₂)₂— | —NHC(=NH)NH(4-nitro-phenyl) |
| 92 | 4-fluoro-phenyl | —CH₂— | —CH₂-(4-methoxy-phenyl) | N | —NH(CH₂)₂— | —NHC(=NH)NH(1,3-benzodioxol-5-yl) |
| 93 | 4-fluoro-phenyl | —CH₂— | —CH₂-(4-methoxy-phenyl) | N | —NH(CH₂)₂— | —NHC(=NH)NHNH₂ |
| 94 | 3-nitro-phenyl | —CH₂— | —CH₂-(4-methoxy-phenyl) | N | —NH(CH₂)₂— | —NHC(=NH)NH₂ |
| 95 | 4-nitro-phenyl | —CH₂— | —CH₂-(4-methoxy-phenyl) | N | —NH(CH₂)₂— | —NHC(=NH)NH₂ |
| 96 | 3-amino-phenyl | —CH₂— | —CH₂-(4-methoxy-phenyl) | N | —NH(CH₂)₂— | —NHC(=NH)NH₂ |
| 97 | 4-cyano-phenyl | —CH₂— | —CH₂-(4-methoxy-phenyl) | N | —NH(CH₂)₂— | —NHC(=NH)NH₂ |
| 98 | 3-cyano-phenyl | —CH₂— | —CH₂-(4-methoxy-phenyl) | N | —NH(CH₂)₂— | —NHC(=NH)NH₂ |
| 99 | 4-methoxycarbonyl-phenyl | —CH₂— | —CH₂-(4-methoxy-phenyl) | N | —NH(CH₂)₂— | —NHC(=NH)NH₂ |
| 100 | 3-methoxycarbonyl-phenyl | —CH₂— | —CH₂-(4-methoxy-phenyl) | N | —NH(CH₂)₂— | —NHC(=NH)NH₂ |
| 101 | 4-carboxy-phenyl | —CH₂— | —CH₂-(4-methoxy-phenyl) | N | —NH(CH₂)₂— | —NHC(=NH)NH₂ |
| 102 | 3,4-dichloro-phenyl | —CH₂— | —CH₂-(4-methoxy-phenyl) | N | —NH(CH₂)C(Me)₂— | —NHC(=NH)NH₂ |
| 103 | 4-fluoro-phenyl | —CH₂— | —CH₂-(4-methoxy-phenyl) | N | —NH(CH₂)₂— | —NHC(=NH)NH(4-bromo-phenyl) |
| 104 | 4-fluoro-phenyl | —CH₂— | —CH₂-(4-methoxy-phenyl) | N | —NH(CH₂)₂— | —NHC(=NH)NH(pyridin-2-yl) |
| 105 | 4-fluoro-phenyl | —CH₂— | —CH₂-(4-methoxy-phenyl) | N | —NH(CH₂)₂— | —NHC(=NH)NH(pyridin-2-yl-ethyl) |
| 106 | 4-fluoro-phenyl | —CH₂— | —CH₂-(4-methoxy-phenyl) | N | —NH(CH₂)₂— | —NHC(=NH)NH(4-ethoxycarbonyl-phenyl) |
| 107 | 4-fluoro-phenyl | —CH₂— | —CH₂-(4-methoxy-phenyl) | N | —NH(CH₂)₂— | —NHC(=NH)NH(2,4-difluoro-phenyl) |
| 108 | 4-fluoro-phenyl | —CH₂— | —CH₂-(4-methoxy-phenyl) | N | —NH(CH₂)₂— | —NHC(=NH)NH(n-decanyl) |

TABLE 1-continued

| Cpd # | A₁ | L₁ | D | W | L₂ | Q |
|---|---|---|---|---|---|---|
| 109 | 4-t-butoxy-phenyl | —CH₂— | —CH₂-(4-methoxy-phenyl) | N | —NH(CH₂)₂— | —NHC(=NH)NH₂ |
| 110 | 4-hydroxy-phenyl | —CH₂— | —CH₂-(4-methoxy-phenyl) | N | —NH(CH₂)₂— | —NHC(=NH)NH₂ |
| 111 | 2-chloro-thiazol-4-yl | —CH₂— | —CH₂-(4-methoxy-phenyl) | N | —NH(CH₂)₂— | —NHC(=NH)NH₂ |
| 112 | benzofuran-2-yl | —CH₂— | —CH₂-(4-methoxy-phenyl) | N | —NH(CH₂)₂— | —NHC(=NH)NH₂ |
| 113 | 3,4-dichloro-phenyl | —CH₂— | —CH₂-(4-methoxy-phenyl) | N | —NH(CH₂)₂— | —N(Me)C(=NH)NH₂ |
| 114 | 4-fluoro-phenyl | —CH₂— | —CH₂-(4-methoxy-phenyl) | N | —NH(CH₂)₂— | —NHC(=NH)NH(CH₂CF₃) |
| 115 | 4-fluoro-phenyl | —CH₂— | —CH₂-(4-methoxy-phenyl) | N | —NH(CH₂)₂— | —NHC(=NH)NH(3-methoxypropyl) |
| 116 | 4-fluoro-phenyl | —CH₂— | —CH₂-(4-methoxy-phenyl) | N | —NH(CH₂)₂— | —NHC(=NH)piperidin-1-yl |
| 117 | 4-fluoro-phenyl | —CH₂— | —CH₂-(4-methoxy-phenyl) | N | —NH(CH₂)₂— | —NHC(=NH)N(Me)phenyl |
| 118 | 4-fluoro-phenyl | —CH₂— | —CH₂-(4-methoxy-phenyl) | N | —NH(CH₂)₂— | —NHC(=NH)NH(2-fluoro-phenyl) |
| 119 | 4-fluoro-phenyl | —CH₂— | —CH₂-(4-methoxy-phenyl) | N | —NH(CH₂)₂— | —NHC(=NH)NH(4-fluoro-phenyl) |
| 120 | 4-fluoro-phenyl | —CH₂— | —CH₂-(4-methoxy-phenyl) | N | —NH(CH₂)₂— | —NHC(=NH)NH(4-methyl-phenyl) |
| 121 | 4-fluoro-phenyl | —CH₂— | —CH₂-(4-methoxy-phenyl) | N | —NH(CH₂)₂— | —NHC(=NH)NH(t-butyl) |
| 122 | 4-chloro-phenyl | —CH₂— | —CH₂-(4-amino-phenyl) | N | —NH(CH₂)₂— | —NHC(=NH)NH₂ |
| 123 | t-butyl | —CH₂— | —CH₂-(4-methoxy-phenyl) | N | —NH(CH₂)₂— | —NHC(=NH)NH₂ |
| 124 | cyclopentyl | —CH₂— | —CH₂-(4-methoxy-phenyl) | N | —NH(CH₂)₂— | —NHC(=NH)NH₂ |
| 125 | 4-amino-phenyl | —CH₂— | —CH₂-(4-methoxy-phenyl) | N | —NH(CH₂)₂— | —NHC(=NH)NH₂ |
| 126 | 4-fluoro-phenyl | —CH₂— | —CH₂-(4-methoxy-phenyl) | N | —NH(CH₂)₂— | —NHC(=NH)NH(adamantan-2-yl) |
| 127 | 4-fluoro-phenyl | —CH₂— | —CH₂-(4-methoxy-phenyl) | N | —NH(CH₂)₂— | —NHC(=NH)NH(4-trifluoromethoxy-phenyl) |
| 128 | 4-fluoro-phenyl | —CH₂— | —CH₂-(4-methoxy-phenyl) | N | —NH(CH₂)₂— | —NHC(=NH)NH(4-hydroxy-phenyl) |
| 129 | 4-chloro-phenyl | —CH₂— | —CH₂-phenyl | N | —NH(CH₂)₂— | —NHC(=NH)NH₂ |
| 130 | 4-chloro-phenyl | —CH₂— | —CH₂-furan-3-yl | N | —NH(CH₂)₂— | —NHC(=NH)NH₂ |
| 131 | 4-fluoro-phenyl | —CH₂— | —CH₂-(4-methoxy-phenyl) | N | 1,4-cyclohexyl | —NHC(=NH)NH₂ |
| 132 | 4-fluoro-phenyl | —CH₂— | —CH₂-(4-methoxy-phenyl) | N | —NHCH₂C(=O)— | —NHC(=NC(=O)O-t-butyl)NH₂ |
| 133 | 4-fluoro-phenyl | —CH₂— | —CH₂-(4-methoxy-phenyl) | N | —NH(CH₂)₂— | —NHC(=NH)NH(2-methylthio-phenyl) |
| 134 | 4-fluoro-phenyl | —CH₂— | —CH₂-(4-methoxy-phenyl) | N | —NH(CH₂)₂— | —NHC(=NH)NH(C(=O)phenyl) |
| 135 | 4-fluoro-phenyl | —CH₂— | —CH₂-(4-methoxy-phenyl) | N | —NH(CH₂)₂— | —NHC(=NH)NH(pyrimidin-2-yl) |
| 136 | 4-fluoro-phenyl | —CH₂— | —CH₂-(4-methoxy-phenyl) | N | —NH((S)—CHMe)₂— | —NHC(=NH)NH₂ |
| 137 | 4-fluoro-phenyl | —CH₂— | —CH₂-(4-methoxy-phenyl) | N | —NH((R)—CHMe)₂— | —NHC(=NH)NH₂. |
| 138 | 4-fluoro-phenyl | —CH₂— | —CH₂-(4-methoxy-phenyl) | N | —NH(CH₂)₂— | —NH(=NH)NH(4-trifluoromethyl-5,6,7,8-tetrahydro-quinazolin-2-yl) |
| 139 | 4-fluoro-phenyl | —CH₂— | —CH₂-(4-methoxy-phenyl) | N | —NH(CH₂)₂— | —NHC(=NH)NH(5-methyl-pyridin-2-yl) |
| 140 | 4-fluoro-phenyl | —CH₂— | —CH₂-(4-methoxy-phenyl) | N | —NH(CH₂)₂— | —NHC(=NH)morpholin-4-yl |
| 141 | 4-chloro-phenyl | —CH₂— | —CH₂-furan-2-yl | N | —NH(CH₂)₂— | —NHC(=NH)NH₂ |
| 142 | 4-chloro-phenyl | —CH₂— | —CH₂-(4-methoxy-phenyl) | N | —NH(CH₂)₅— | —NHC(=NH)NH₂ |
| 143 | 4-methoxy-phenyl | —CH₂— | —CH₂-(4-hydroxy-phenyl) | N | —NH(CH₂)₂— | —NHC(=NH)NH₂ |
| 144 | 4-chloro-phenyl | —CH₂— | —CH₂-(4-methoxy-phenyl) | N | —NH(CH₂)₆— | —NHC(=NH)NH₂ |

TABLE 1-continued

| Cpd # | $A_1$ | $L_1$ | D | W | $L_2$ | Q |
|---|---|---|---|---|---|---|
| 145 | 4-methoxyphenyl | —(CH$_2$)$_2$— | —CH$_2$-(4-methoxyphenyl) | N | —NH(CH$_2$)$_2$— | —NHC(=NH)NH$_2$ |
| 146 | 4-methoxyphenyl | —(CH$_2$)$_3$— | —CH$_2$-(4-methoxyphenyl) | N | —NH(CH$_2$)$_2$— | —NHC(=NH)NH$_2$ |
| 147 | 3,4-dichlorophenyl | —CH$_2$— | —CH$_2$-(4-methoxycarbonylphenyl) | N | —NH(CH$_2$)$_2$— | —NHC(=NH)NH$_2$ |

The compounds of the present invention may also be present in the form of pharmaceutically acceptable salts. For use in medicine, the salts of the compounds of this invention refer to non-toxic "pharmaceutically acceptable salts" (Rcf. International J. Pharm., 1986, 33, 201-217; J. Pharm. Sci., 1997 (January), 66, 1, 1). Other salts well known to those in the art may, however, be useful in the preparation of compounds according to this invention or of their pharmaceutically acceptable salts. Representative organic or inorganic acids include, but are not limited to, hydrochloric, hydrobromic, hydroiodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are intended to be encompassed within the scope of this invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

Even though the compounds of the present invention (including their pharmaceutically acceptable salts and pharmaceutically acceptable solvates) can be administered alone, they will generally be administered in admixture with a pharmaceutical carrier, excipient, or diluent selected with regard to the intended route of administration and standard pharmaceutical or veterinary practice. Thus, the present invention is directed to pharmaceutical and veterinary compositions comprising compounds of Formula (I) and one or more pharmaceutically acceptable carriers, excipients or diluents.

By way of example, in the pharmaceutical and veterinary compositions of the present invention, the compounds of the present invention may be admixed with any suitable binder(s), lubricant(s), suspending agent(s), coating agent(s), and/or solubilising agent(s).

Tablets or capsules of the compounds may be administered singly or two or more at a time, as appropriate. It is also possible to administer the compounds in sustained release formulations.

Alternatively, the compounds of the general Formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilisers and preservatives as may be required.

For some applications, preferably the compositions are administered orally in the form of tablets containing excipients such as starch or lactose, or in capsules or ovules either alone or in admixture with excipients, or in the form of elixirs, solutions or suspensions containing flavouring or coloring agents.

The compositions (as well as the compounds alone) can also be injected parenterally, for example intracavernosally, intravenously, intramuscularly or subcutaneously. In this case, the compositions will comprise a suitable carrier or diluent.

For parenteral administration, the compositions are best used in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

By way of further example, pharmaceutical and veterinary compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate the major site of absorption. For parenteral administration, the carrier will usually consist of sterile water and other ingredients may be added to increase solubility or preservation. Injectable suspensions or solutions may also be prepared utilizing aqueous carriers along with appropriate additives.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those skilled in that art. To be administered in the form of a transdermal delivery system, the dosage administration will, of course, be continuous rather than intermittent throughout the dosage regimen.

A therapeutically effective amount for use of the instant compounds or a pharmaceutical composition thereof comprises a dose range of from about 0.001 mg to about 1,000 mg, in particular from about 0.1 mg to about 500 mg or, more particularly from about 1 mg to about 250 mg of active ingredient per day for an average (70 kg) human.

For oral administration, a pharmaceutical composition is preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated.

It is also apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Compounds of this invention may be administered in any of the foregoing compositions and dosage regimens or by means of those compositions and dosage regimens established in the art whenever use of the compounds of the invention as prokineticin receptor antagonists is required for a subject in need thereof.

The invention also provides a pharmaceutical or veterinary pack or kit comprising one or more containers filled with one or more of the ingredients of the pharmaceutical and veterinary compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

As antagonists of a PK1 receptor, the compounds of Formula (I) are useful in methods for treating or preventing a disease or condition in a mammal which disease or condition is affected by the antagonistic activity of one or more PK1 receptors. Such methods comprise administering to a mammal in need of such treatment or prevention a therapeutically effective amount of a compound, salt or solvate of Formula (I). The compounds of Formula (I) are useful in methods for preventing or treating gastrointestinal (GI) diseases, cancers of the GI tract and reproductive organs, and pain. Examples of GI diseases to be within the scope of the present invention include, but are not limited to: irritable bowel syndrome (IBS, including diarrhea-predominant, as well as alternating diarrhea/constipation forms of IBS), inflammatory bowel disease (IBD, including ulcerative colitis, and Crohn's disease), and GERD and secretory bowel disorders induced by pathogens. Examples of cancers within the scope of the present invention include, but are not limited to, testicular cancer, ovarian cancer, Leydig cell carcinoma, and cancers of the small or large bowel. An example of pain to be covered within the scope of the present invention, is, but not restricted to, visceral hyperalgesia often associated with IBS and IBD.

While the present invention comprises compositions comprising one or more of the compounds of Formula (I) the present invention also comprises compositions comprising intermediates used in the manufacture of compounds of Formula (I).

Representative IUPAC names for the compounds of the present invention were derived using the ACD/LABS SOFTWARE™ Index Name Pro Version 4.5 nomenclature software program provided by Advanced Chemistry Development, Inc., Toronto, Ontario, Canada.

Abbreviations used in the instant specification, particularly the Schemes and Examples, are as follows:
Cpd or Cmpd=compound
d=day/days
DIAD=diisopropyl azodicarboxylate
DIPEA
or DIEA=diisopropylethylamine
DMEM=Dulbecco's Modified Eagle Medium
DMF=N,N-dimethylformamide
DMSO=dimethylsulfoxide
EtOAc=ethyl acetate
EtOH=ethanol
h=hour/hours M=molar
MeCN=acetonitrile
MeOH=methanol
min=minutes
NaOMe=sodium methoxide
PyBOP=benzotriazole-1-yl-oxy-tris-pyrrolidino-phosphonium hexafluorophosphate NH. A compound of formula A1 may be methylated with a methylating agent such as methyl iodide in a polar solvent such as methanol to give a compound of formula A2. A compound of formula A2 may be condensed with an appropriately substituted isocyanate such as N-chlorocarbonyl isocyanate in the presence of excess tertiary amine such as diisopropylethylamine to give a triazine of formula A3.

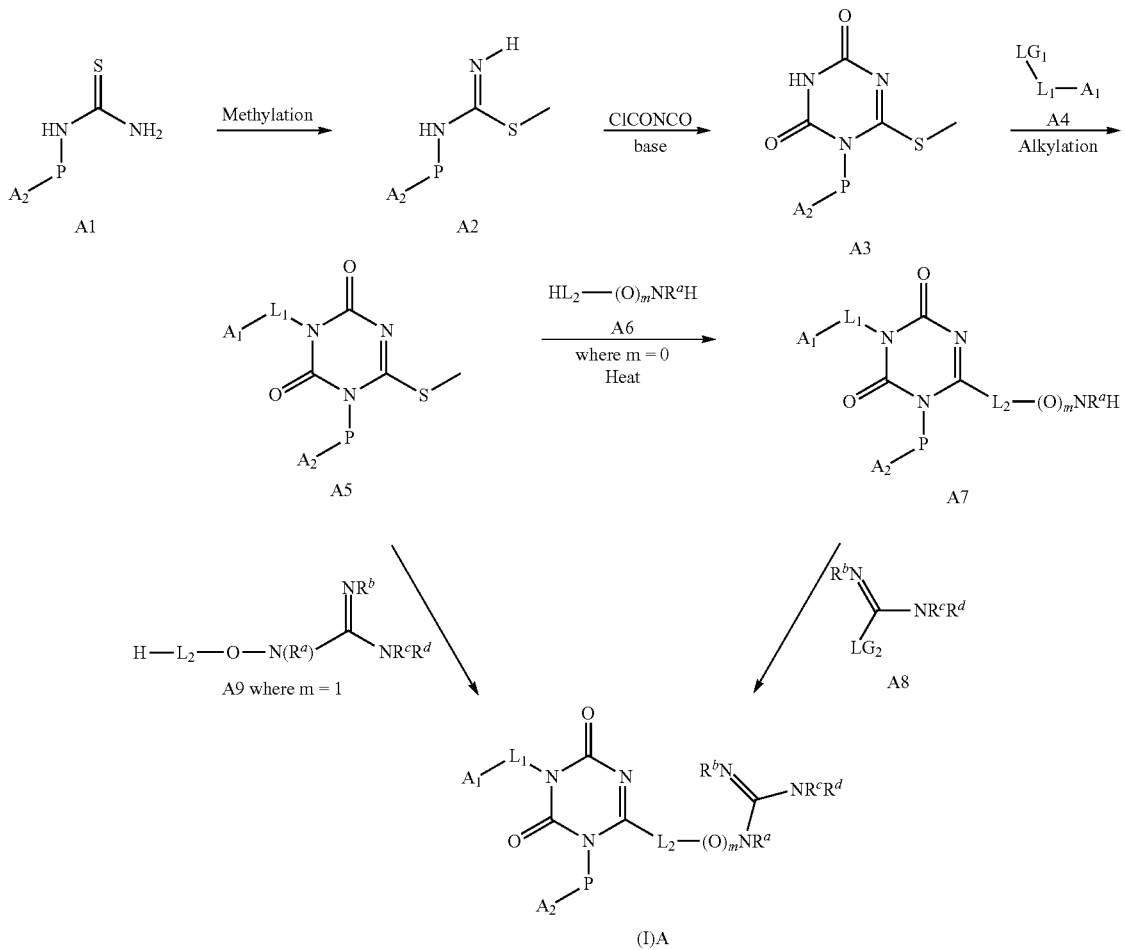

rt/RT=room temperature
THF=tetrahydrofuran
TFA=trifluoroacetic acid

General Schemes

Representative compounds of the present invention can be synthesized in accordance with the general synthetic methods described below and are illustrated in the schemes that follows. The starting materials and reagents used in the schemes that follow are understood to be either commercially available or prepared by methods known to those skilled in the art. Since the schemes are an illustration, the invention should not be construed as being limited by the chemical reactions and conditions expressed.

Scheme A illustrates the general synthesis of compounds of the present invention wherein $L_2$ is other than —NHC(=O)—(CH$_2$)$_{1-4}$—, and —X$_2$—(CH$_2$)$_{0-4}$—, and X$_1$ of L$_2$ is A compound of formula A3 may be alkylated with a compound of formula A4, wherein LG$_1$ is a leaving group, using conventional chemistry known to one versed in the art. For instance, when LG$_1$ is a hydroxy group, compound A4 may be coupled with compound A3 with the aid of a coupling agent such as DIAD in the presence of triphenylphosphine in a non-alcoholic polar solvent such as THF or methylene chloride. Alternatively, LG$_1$ may be a halide, tosylate, or the like such that LG$_1$ is displaced by the amino portion of a compound of A3 to give a compound of formula A5.

A compound of formula A5 may be further elaborated by nucleophilic substitution with a compound of formula A6 (wherein X$_1$ is NH and m is zero) to provide a compound of formula A7. One versed in the art will recognize that when L$_2$ is asymmetrical, a nitrogen-protecting group may be necessary to avoid competing reactions. A G-substituent of Formula (I) may be installed by treatment of the terminal amine of a compound of formula A7 with an activated amidine of formula A8 wherein LG$_2$ is a leaving group such as a halide, an alkoxide, an imidazole or pyrazole, an activated alkoxide, or the like, to give compound IA of Formula (I) wherein m is zero. Alternatively, when m is equal to one, an oxy-guanidine substituent may be incorporated by treatment of a compound of formula A7 with a compound of formula A9 to form a compound (I)A of Formula (I) wherein m is one.

Scheme B illustrates the general synthesis of compounds of the present invention wherein L$_2$ is —NHC(=O)—(CH$_2$)$_{1-4}$—. A compound of formula A5 may be converted to its corresponding amine by treatment with ammonia, or other source of ammonia such as ammonium hydroxide, to give a compound of formula B1. The amino group of a compound B1 may be acylated using conventional chemistry with a compound of formula B2, wherein LG$_3$ is a leaving group such as a halide when B2 is an acid chloride, a hydroxy group when B2 is a carboxylic acid, an alkylcarboxylate when B2 is an anhydride, or an imidazole when B2 is an acylimidazole. Alternatively, B2 may be an activated ester or the like. The K substituent of compounds of formula B2 is either a leaving group LG$_1$ as defined herein, or K is an R$^a$-substituted amino group protected with an appropriate amino-protecting group (PG).

duced into a compound of formula C6 using the methods described herein to provide a compound (I)C of Formula (I).

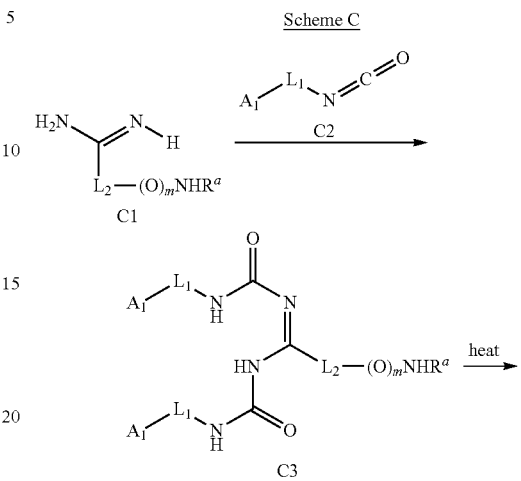

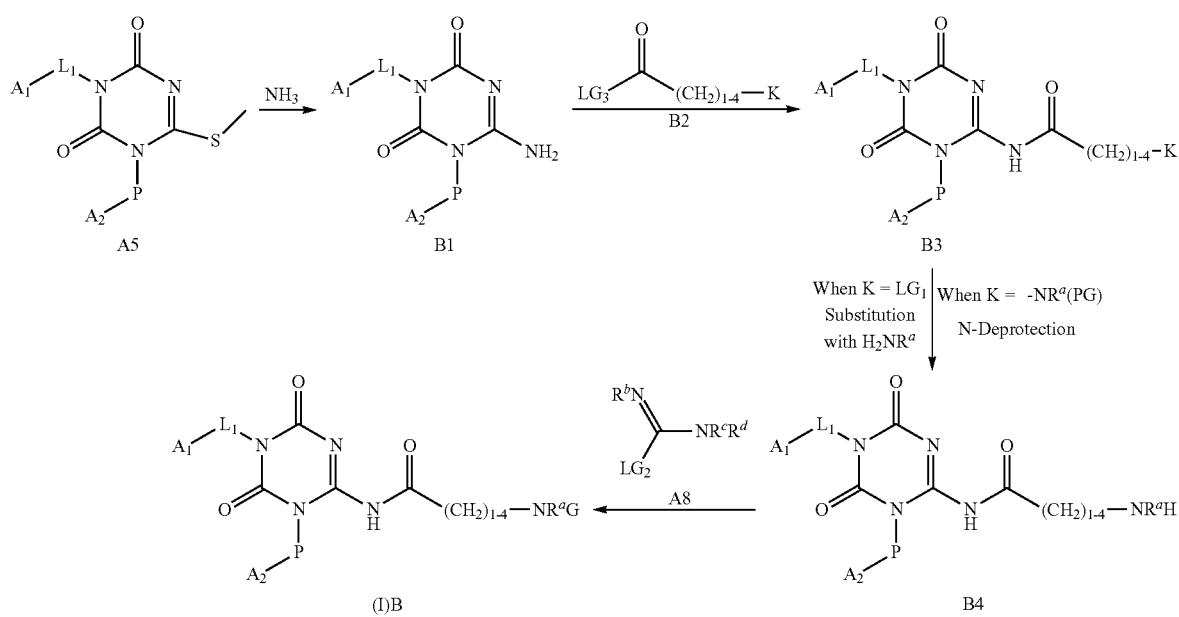

To prepare a compound of formula B4, a compound of formula B3 may either be N-deprotected (when K is —NR$^a$(PG)) using reagents and methods known to one versed in the art, or may undergo a nucleophilic displacement with amine H$_2$NR$^a$ (when K is a LG$_1$). The resulting amine of formula B4 may then be treated with an activated amidine of formula A8 to give a compound (I)B of Formula (I).

Scheme C describes the general synthesis of compounds of the present invention wherein X$_1$ of L$_2$ is a direct bond. A compound of formula C1 may be condensed with an isocyanate of formula C2 to give a compound of formula C3 which, upon heating, affords a triazine of formula C4. The amino group of a compound of formula C4 may be appropriately substituted using an alkylating agent of formula C5 to afford a compound of formula C6. A G-substituent may be intro- -continued

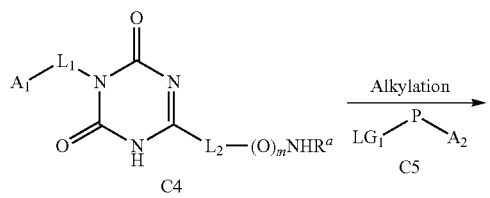

-continued

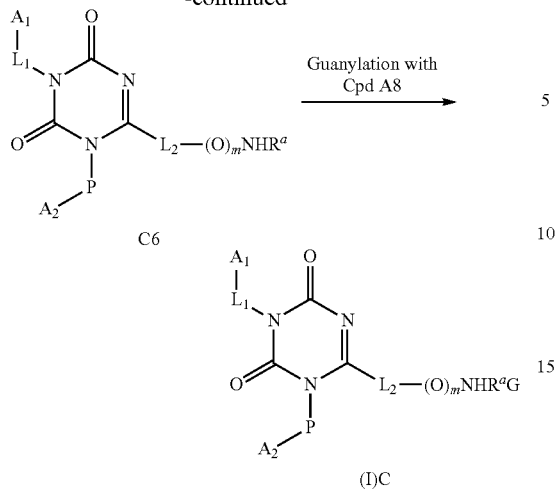

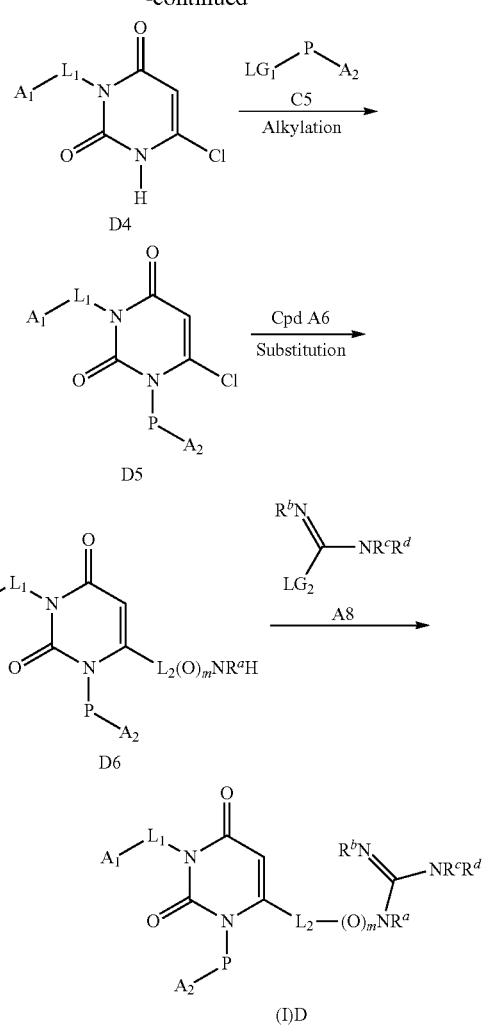

Scheme D illustrates the general synthesis of compounds of the present invention wherein W is CH, $L_2$ is other than —NHC(=O)—(CH$_2$)$_{1-4}$—, and $X_1$ of $L_2$ is NH. A compound of formula D1 may be condensed with a compound of formula D2 with heating, wherein $LG_2$ is as defined herein, to form a compound of formula D3. A compound of formula D3 may then be treated with phosphorus oxychloride, $PCl_5$, or the like and heat to afford a compound of formula D4. A compound of formula C5 may be used to install —P-$A_2$ via conventional alkylation procedures. A compound of formula D5 may be elaborated via a nucleophilic displacement of the chloride with an amine A6 (when $X_1$ is NH) to afford a compound of formula D6. Further elaboration using the chemistry described herein may be employed to provide compound (I)D of Formula (I).

Scheme D

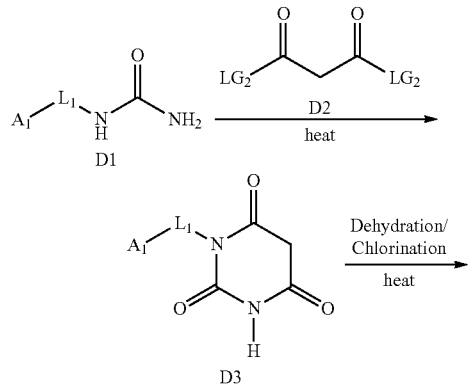

Scheme E illustrates the general synthesis of compounds of the present invention wherein W is CH and $L_2$ is —NHC(=O)—(CH$_2$)$_{1-4}$—. A compound of formula D5 may be treated with ammonia or other source of ammonia such as ammonium hydroxide to afford the corresponding amino compound of formula E1. The amino group may be acylated with a compound of formula B2 and further elaborated to a compound (I)E of Formula (I) using the methods described herein.

Scheme E

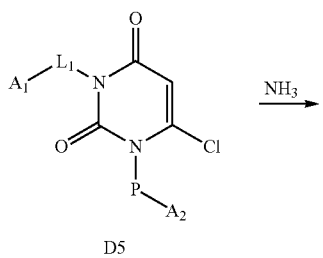

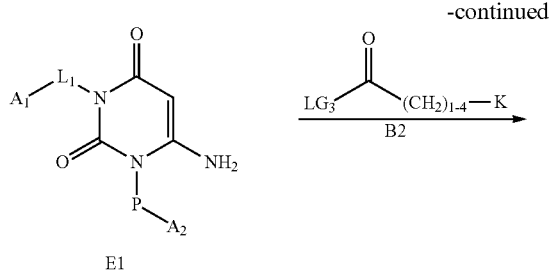

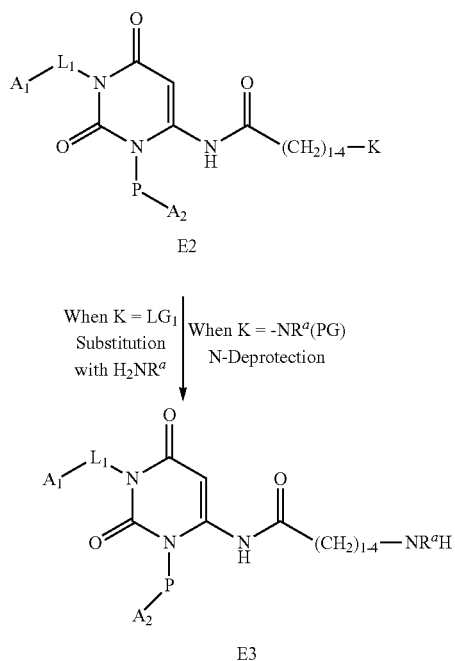

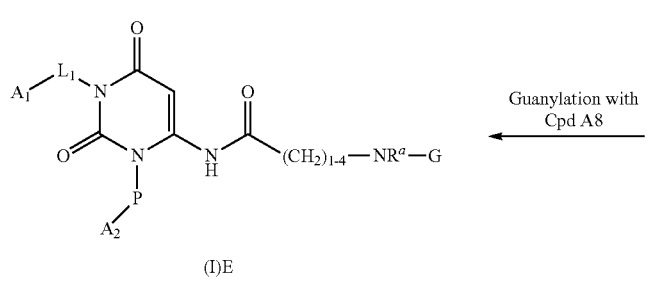

Scheme F illustrates the general synthesis of compounds of the present invention wherein W is CH, $X_1$ of $L_2$ is a direct bond and $L_2$ is any one of those which includes $X_1$. A compound of formula F1 may be condensed with a compound of formula F2 under basic conditions in the presence of a lower alkyl alcohol to form a compound of formula F3. A compound of formula F3 may be condensed with a urea of formula F4 to form a cyclic compound of formula F5.

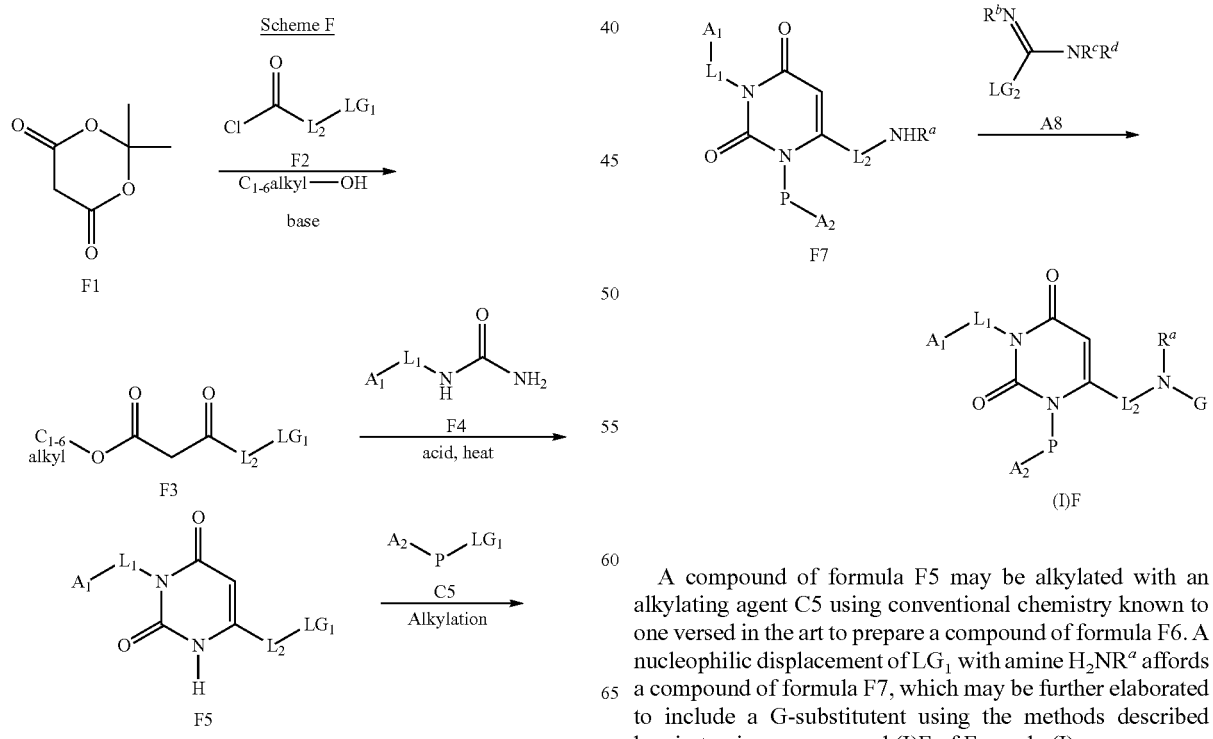

A compound of formula F5 may be alkylated with an alkylating agent C5 using conventional chemistry known to one versed in the art to prepare a compound of formula F6. A nucleophilic displacement of $LG_1$ with amine $H_2NR^a$ affords a compound of formula F7, which may be further elaborated to include a G-substitutent using the methods described herein to give a compound (I)F of Formula (I).

Scheme G illustrates the general synthesis of compounds of the present invention wherein W is N and $L_2$ is —$X_2$—$(CH_2)_{0-4}$—. A compound of formula G1 may be treated with a base followed by alkylation with a compound of formula A4 to afford a compound of formula G2. Treatment of a compound of formula G2 with hydrogen peroxide in the presence of an aqueous base such as hydroxide gives a bis-amido compound of formula G3, which may then be condensed with a compound of formula G4 to form a triazine compound of formula G5.

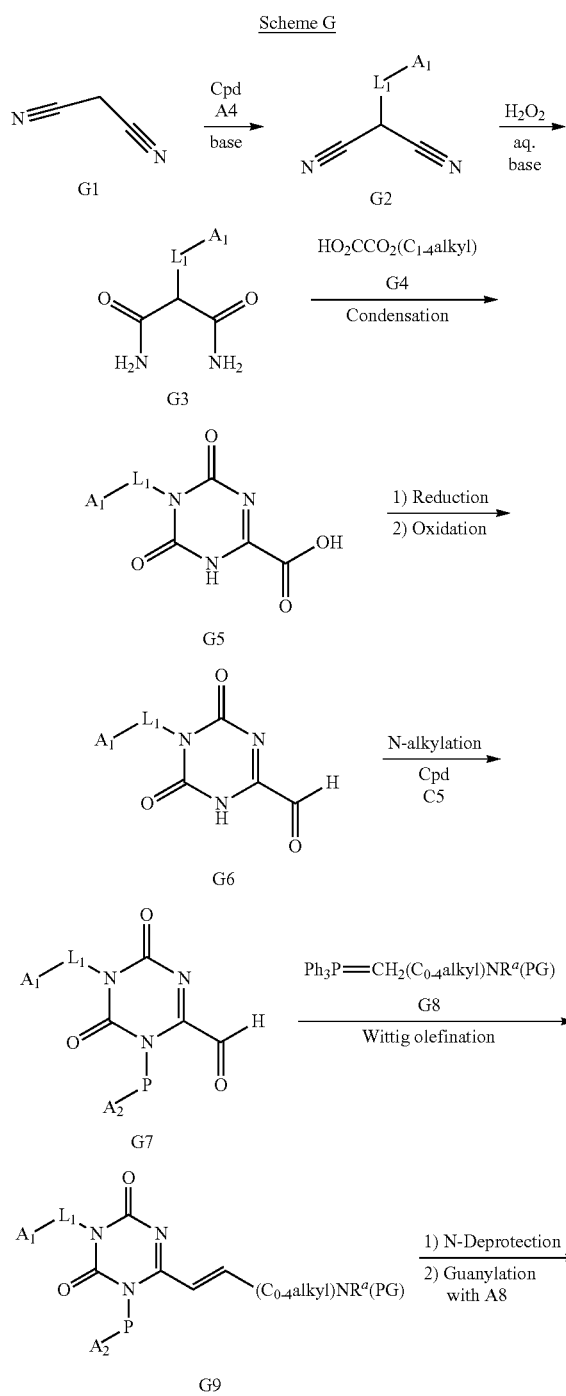

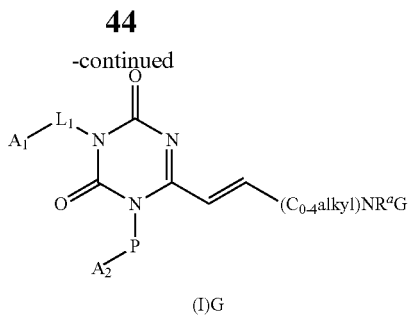

Using conventional reagents and methods known to one skilled in the art, the carboxy group of compounds of G5 may be reduced to the corresponding alcohol, followed by oxidation to an aldehyde of formula G6. The secondary amino group may be substituted with a compound of formula C5 using coupling chemistry or standard alkylation chemistry to afford a compound of formula G7. The aldehyde portion of the compound may participate in a Wittig olefination with a compound of formula G8 (wherein PG is as previously defined) to provide a compound of formula G9 wherein $L_2$ includes an alkenyl group, $X_2$. Subsequent removal of the amino-protecting group followed by guanylation gives a compound (I) G of Formula (I).

Scheme H illustrates the general synthesis of compounds of the present invention wherein W is CH and $L_2$ is —$X_2$—$(CH_2)_{0-4}$—. A compound of formula H1 may be condensed with an O-alkylated isourea to afford a cyclic compound of formula H2. The amine may be deprotonated with an organometallic base and subsequently treated with a compound of formula A4 to install the -$L_1A_1$ substituents of Formula (I). O-demethylation of the alkylated compounds of H2 afford compounds of formula H3. Using conventional oxidation chemistry, the methyl substituent of H3 may be converted to its corresponding aldehyde, affording a compound of formula H4. The aldehyde may be elaborated to a compound of Formula (I) wherein $L_2$ is —$X_2$—$(CH_2)_{0-4}$— using the synthetic steps described in Scheme G for the conversion of a compound G7 to compounds of formula (I)G.

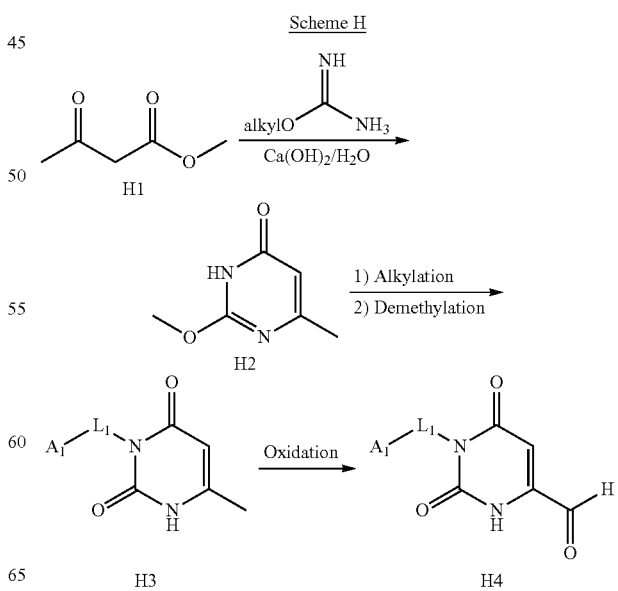

SPECIFIC EXAMPLES

Specific compounds which are representative of this invention were prepared as per the following examples and reaction sequences; the examples and the diagrams depicting the reaction sequences are offered by way of illustration, to aid in the understanding of the invention and should not be construed to limit in any way the invention set forth in the claims which follow thereafter. The instant compounds may also be used as intermediates in subsequent examples to produce additional compounds of the present invention. No attempt has been made to optimize the yields obtained in any of the reactions. One skilled in the art would know how to increase such yields through routine variations in reaction times, temperatures, solvents and/or reagents.

Reagents were purchased from commercial sources. Nuclear magnetic resonance (NMR) spectra for hydrogen atoms were measured in the indicated solvent with (TMS) as the internal standard on a Bruker AM-360 (360 MHz) spectrometer. The values are expressed in parts per million downfield from TMS. The mass spectra (MS) were determined on a Micromass Platform LC spectrometer or an Agilent LC spectrometer using electrospray techniques. Microwave accelerated reactions were performed using either a CEM Discover or a Personal Chemistry Smith Synthesizer microwave instrument. Stereoisomeric compounds may be characterized as racemic mixtures or as separate diastereomers and enantiomers thereof using X-ray crystallography and other methods known to one skilled in the art. Unless otherwise noted, the materials used in the examples were obtained from readily available commercial suppliers or synthesized by standard methods known to one skilled in the art of chemical synthesis. The substituent groups, which vary between examples, are hydrogen unless otherwise noted.

Example 1

N-{2-[5-(4-Ethyl-benzyl)-1-(4-methoxy-benzyl)-4,6-dioxo-1,4,5,6-tetrahydro-[1,3,5]triazin-2-ylamino]-ethyl}-guanidine (Cpd 46)

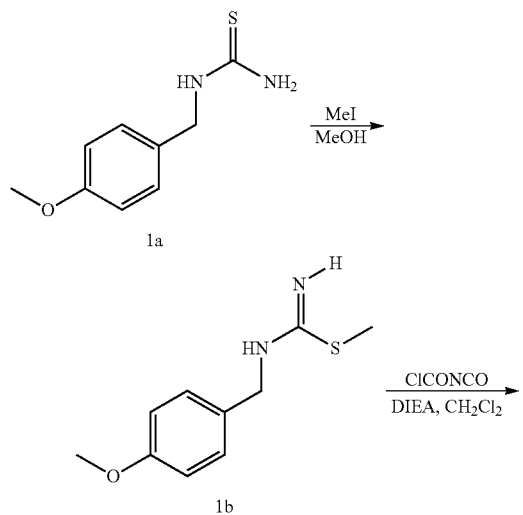

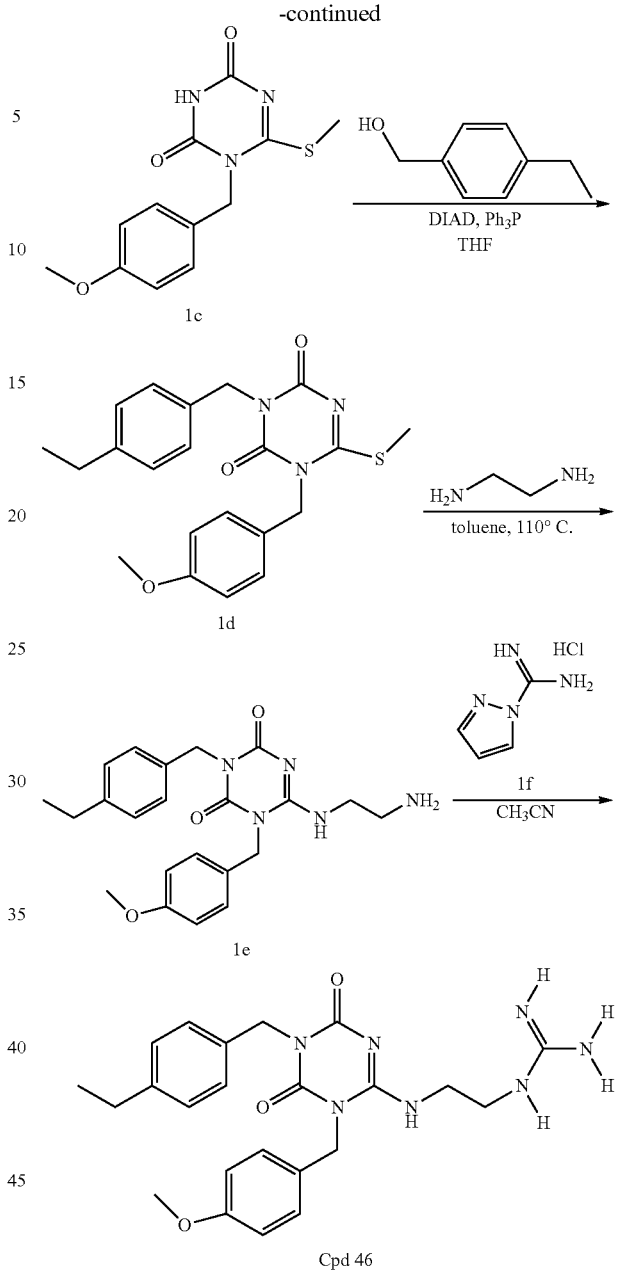

A. 1-(4-Methoxy-benzyl)-6-methylsulfanyl-1H-[1,3,5]triazine-2,4-dione (Cpd 1c). To (4-methoxy-benzyl) thiourea (2.00 g, 10.1 mmol) in MeOH (40 mL) was added methyl iodide (0.64 mL, 10.1 mmol). The reaction was stirred at room temperature for 24 h. The reaction mixture was concentrated to yield 2.00 g of crude compound (1b) that was used in the next step without further purification.

B. To Compound 1b (3.6 g, 17 1 mmol) in methylene chloride (40 mL) was added excess diisopropylethylamine (6.61 g, 51.3 mmol). The reaction mixture was cooled to 0° C. A portion of N-chlorocarbonyl isocyanate (1.78 g, 17.1 mmol) was added dropwise. The reaction mixture was allowed to slowly warm to room temperature. After 24 h, water was added and the reaction mixture was extracted with ethyl acetate. The phases were separated, and the organic layer was dried over sodium sulfate, filtered, and concentrated. Methanol was added to the crude product, and the solid was collected by vacuum filtration to give Compound 1c (1.5 g). $^1$H NMR (DMSO-$d_6$) δ 2.45 (3H, s), 3.73 (3H, s), 4.98 (2H, s), 6.89-6.92 (2H, d, J=8.5 Hz), 7.22-7.25 (2H, d, J=8.5 Hz), 11.58 (1H, s).

C. 3-(4-Ethyl-benzyl)-1-(4-methoxy-benzyl)-6-methyl-sulfanyl-1H-[1,3,5]triazine-2,4-dione (Cpd 1d). To Cpd 1c (0.1 g, 0.35 mmol) in tetrahydrofuran was added 4-ethylbenzyl alcohol (0.049 g, 0.35 mmol), triphenylphosphine (0.19 g 0.71 mmol) and diisopropyl azodicarboxylate (0.087 g, 0.43 mmol). The reaction stirred at room temperature for 64 h. The reaction mixture was taken up in ethyl acetate, washed with water, and the phases were separated. The organic layer was dried over sodium sulfate, filtered, and concentrated. The resulting material was purified by normal phase chromatography using an ISCO automated system to give Cpd 1d (0.14 g) as a white solid.

D. 6-(2-Amino-ethylamino)-3-(4-ethyl-benzyl)-1-(4-methoxy-benzyl)-1H-[1,3,5]-triazine-2,4-dione (Cpd 1e). To 1-(4-methoxy-benzyl)-6-methylsulfanyl-1H-[1,3,5]triazine-2,4-dione (0.14 g, 0.33 mmol) in toluene was added excess ethylenediamine (0.10 g, 1.76 mmol). The reaction mixture was heated at 110° C. for 18 h. The reaction mixture was cooled to room temperature, diluted with water and extracted with ethyl acetate. The phases were separated and the organic layer was dried over sodium sulfate, filtered and concentrated. The resultant Cpd 1e (0.11 g) was used in the next step without further purification.

E. N-{2-[5-(4-Ethyl-benzyl)-1-(4-methoxy-benzyl)-4,6-dioxo-1,4,5,6-tetrahydro-[1,3,5]triazin-2-ylamino]-ethyl}-guanidine (Cpd 46). To a mixture of Cpd 1e (0.11 g, 0.26 mmol) in acetonitrile (4 mL) was added excess diisopropylamine (0.069 g, 0.53 mmol) and 1H-pyrazolo-1-carboxamidine hydrochloride, Cpd 1f, (0.039 g, 0.26 mmol). The reaction mixture was stirred for 18 h at room temperature. A white solid precipitated from the reaction mixture and was collected by filtration to give the title compound 46 (98% pure by HPLC, 0.0119 g). $^1$H NMR (DMSO-$d_6$) δ 1.01-1.04 (3H, t, J=7.5 Hz), 2.41-2.47 (2H, q, J=7.4 Hz), 3.26-3.16 (4H, m) 3.61 (3H, s), 4.75 (2H, s), 4.93 (2H, s), 6.77-6.79 (2H, d, J=8.64 Hz), 7.00-7.12 (6H, m), 7.55 (1H, m), 8.06 (1H, m).

Using the procedures of Example 1 and the appropriate reagents, starting materials and purification methods known to those skilled in the art, the following compounds of the present invention were prepared: compounds 39, 45, 77, 78, 79, 80, 82, 83, 109, 111, 112, 123, 124, 131, 136, 137, 145, and 146.

Example 2

N-{2-[5-(4-Fluoro-benzyl)-1-(4-methoxy-benzyl)-4, 6-dioxo-1,4,5,6-tetrahydro-[1,3,5]triazin-2-ylamino]-ethyl}-guanidine (Cpd 17)

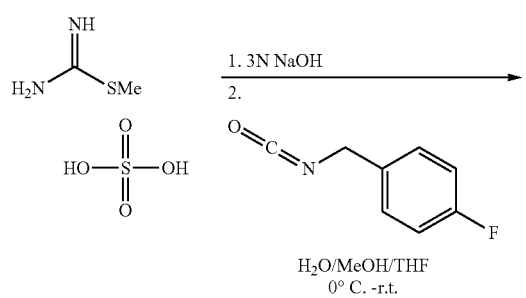

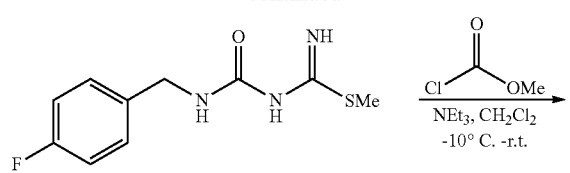

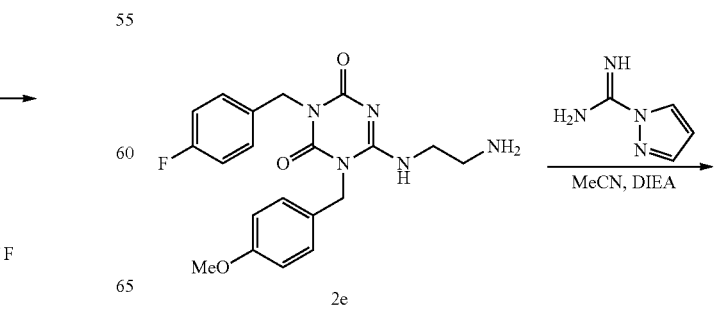

-continued

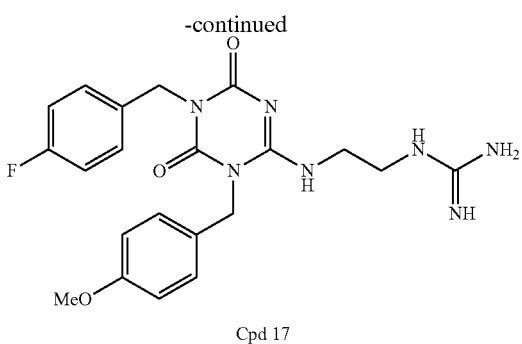

Cpd 17

A. ((4-Fluorobenzyl)amino)carbonyl)carbamimidothioic acid methyl ester (Cpd 2a). S-methylisothiouronium sulfate (10.0 g, 35.9 mmol) was dissolved in 8:2:1 MeOH/H$_2$O/THF and the mixture was treated with 3 N NaOH (12 mL, 35.9 mmol). The solution was then cooled to 0° C. and 4-fluorobenzyl isocyanate (5.43 g, 35.9 mmol) was added dropwise over 30 min. The reaction was stirred overnight and gradually warmed to room temperature. The mixture was then washed with saturated aqueous NH$_4$Cl and extracted with dichloromethane. The combined organic phases were dried over Na$_2$SO$_4$, filtered and concentrated under reduced pressure. The resultant residue was purified on an Isco flash column (20% EtOAc—100% EtOAc in heptanes), to give Compound 2a (4.1 g) as a white powder.

B. 5-(Methylthio)-3,7-dioxo-1-(4-fluorobenzyl)-2-oxa-4,6,8-triazanon-4-en-9-oic acid methyl ester (Cpd 2b). A solution of Compound 2a (4.1 g, 17.0 mmol) in dichloromethane was treated with triethylamine (3.08 mL, 22.1 mmol) and the mixture was cooled to −10° C. Methyl chloroformate (2.62 mL, 34.0 mmol) was added dropwise via an addition funnel over 15 min and the reaction was allowed to stir for 4 h while gradually warming to room temperature. The solution was then washed with saturated aqueous NH$_4$Cl and extracted with dichloromethane. The combined organic phases were dried over Na$_2$SO$_4$, filtered and concentrated. The resultant residue was purified on an Isco flash column (5% MeOH) to afford Compound 2b (3.63 g) as a white solid.

C. 3-(4-Fluoro-benzyl)-6-methylsulfanyl-1H-[1,3,5]triazine-2,4-dione (Cpd 2c). Compound 2b (3.63 g, 12.1 mmol) was dissolved in MeOH (100 mL) and the solution was treated with NaOMe in MeOH (4.6 M, 2.90 mL, 13.3 mmol) and the reaction was allowed to stir at room temperature for 1 h. A white precipitate formed upon addition of the NaOMe. The reaction mixture was diluted with 1N HCl (50 mL) and the resultant precipitate was collected by filtration. The solid was dried under reduced pressure at 160° C. over xylenes to afford Compound 2c (3.6 g) as its HCl salt.

D. 3-(4-Fluoro-benzyl)-1-(4-methoxy-benzyl)-6-methylsulfanyl-1H-[1,3,5]triazine-2,4-dione (Cpd 2d). Compound 2c (500 mg, 1.65 mmol) was dissolved in THF and was treated with 4-methoxybenzyl alcohol (227 mg, 1.65 mmol), triphenylphospine (866 mg, 3.30 mmol), and diisopropyl azodicarboxylate (334 mg, 1.65 mmol). The reaction was allowed to stir overnight at room temperature. After monitoring the reaction via HPLC, the solution was partitioned between water and ethyl acetate. Combined organic layers were dried over anhydrous sodium sulfate, filtered and reduced. The crude mixture was purified via Isco flash column (20% ethyl acetate—100% ethyl acetate in heptanes, 40 min) to afford 390 mg of Cpd 2d as a white solid. $^1$H NMR (DMSO, d$_6$). δ 3.29 (s, 3H), 3.74 (s, 3H), 4.93 (s, 2H), 5.03 (s, 2H), 6.89-6.92 (d, 2H, J=8.62), 7.12-7.36 (m, 4H), 7.38-7.41 (m, 2H).

E. 4-[3-(3,4-Dichloro-benzyl)-6-methylsulfanyl-2,4-dioxo-3,4-dihydro-2H-[1,3,5]triazin-1-ylmethyl]-benzamide (Cpd 2d). Compound 2c (dichlorobenzyl) (200 mg, 0.56 mmol) was dissolved in MeCN and was treated with diisopropylethylamine (0.196 mL, 1.13 mmol) and 4-chloromethyl benzyl chloride (96 mg, 0.56 mmol). The reaction mixture was heated to 80° C. and was allowed to stir overnight. The reaction mixture was washed with saturated aqueous NH$_4$Cl and extracted with ethyl acetate. The combined organic extracts were dried over Na$_2$SO$_4$, filtered and concentrated. The resultant crude mixture was purified by Isco flash column (20%-100% EtOAc in heptanes, 40 min) to afford 70 mg of Cpd 2d as a white powder.

F. 6-(2-Amino-ethylamino)-3-(4-fluoro-benzyl)-1-(4-methoxy-benzyl)-1H-[1,3,5]triazine-2,4-dione (Cpd 2e). A solution of Compound 2d (390 mg, 1.01 mmol) in toluene (8 mL) and was treated with ethylenediamine (302 mg, 5.03 mmol). The reaction was heated to 90° C. and was allowed to stir overnight. The mixture was then partitioned between water and ethyl acetate. The combined organic layers were dried over Na$_2$SO$_4$, filtered and reduced. Reduction provided 390 mg of Cpd 2e as a crude mixture. The crude compound was used in further synthesis without additional purification.

G. N-{2-[5-(4-Fluoro-benzyl)-1-(4-methoxy-benzyl)-4,6-dioxo-1,4,5,6-tetrahydro-[1,3,5]triazin-2-ylamino]-ethyl}-guanidine (Cpd 17). A crude mixture of Cpd 2e (390 mg, 0.98 mmol) was dissolved in acetonitrile (10 mL) and was treated with pyrazole1-carboxamidine hydrochloride (143 mg, 0.98 mmol) and diisopropylethylamine (0.340 mL, 1.95 mmol). The reaction was allowed to proceed overnight at room temperature. Inspection of the reaction mixture showed that a white precipitate had formed and the precipitate was collected and dried by vacuum filtration. The solid collected afforded 307 mg of Cpd 17 as white powder. M$^+$ (ES+)= 442.3.

$^1$H NMR (DMSO, d$_6$). δ 3.33 (m, 4H), 3.73 (s, 3H), 4.89 (s, 2H), 5.04 (s, 2H), 6.89-6.91 (d, 2H, J=8.66 Hz), 7.10-7.16 (t, 2H, J=8.91 Hz), 7.21-7.24 (d, 2H, J=8.63 Hz), 7.32-7.36 (dd, 2H, J=2.90, 5.57 Hz), 7.66 (s, 1H), 8.19 (s, 1H).

Using the procedures of Example 2 and the appropriate reagents, starting materials and purification methods known to those skilled in the art, the following compounds of the present invention were prepared: compounds 1, 2, 3, 4, 5, 6, 7, 8, 9, 11, 12, 13, 14, 15, 16, 18, 19, 20, 21, 22, 23, 24, 25, 25, 29, 30, 31, 32, 33, 34, 35, 36, 37, 38, 40, 41, 50, 51, 52, 57, 68, 69, 85, 86, 87, 129, 130, 142, 144, and 147.

Cpd 51: 4-[3-(3,4-Dichlorobenzyl)-6-(2-guanidinoethylamino)-2,4-dioxo-3,4-dihydro-2H-[1,3,5]triazin-1-yl-methyl]-benzamide δ(DMSO, d$_6$) 3.30-3.37 (m, 4H), 4.90 (s, 2H), 5.10 (s, 1H), 7.27-7.32 (m, 3H), 7.51-7.61 (m, 2H), 7.83 (d, 2H, J=9.7 Hz), 7.94 (s, 1H), 8.08 (t, 1H, J=3.7 Hz).

Example 3

N-{2-[1-Benzyl-3-(4-methoxy-benzyl)-2,6-dioxo-1,2,3,6-tetrahydro-pyrimidin-4-ylamino]-ethyl}-guanidine (Cpd 81)

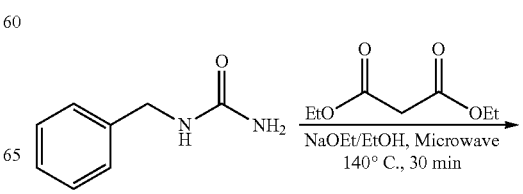

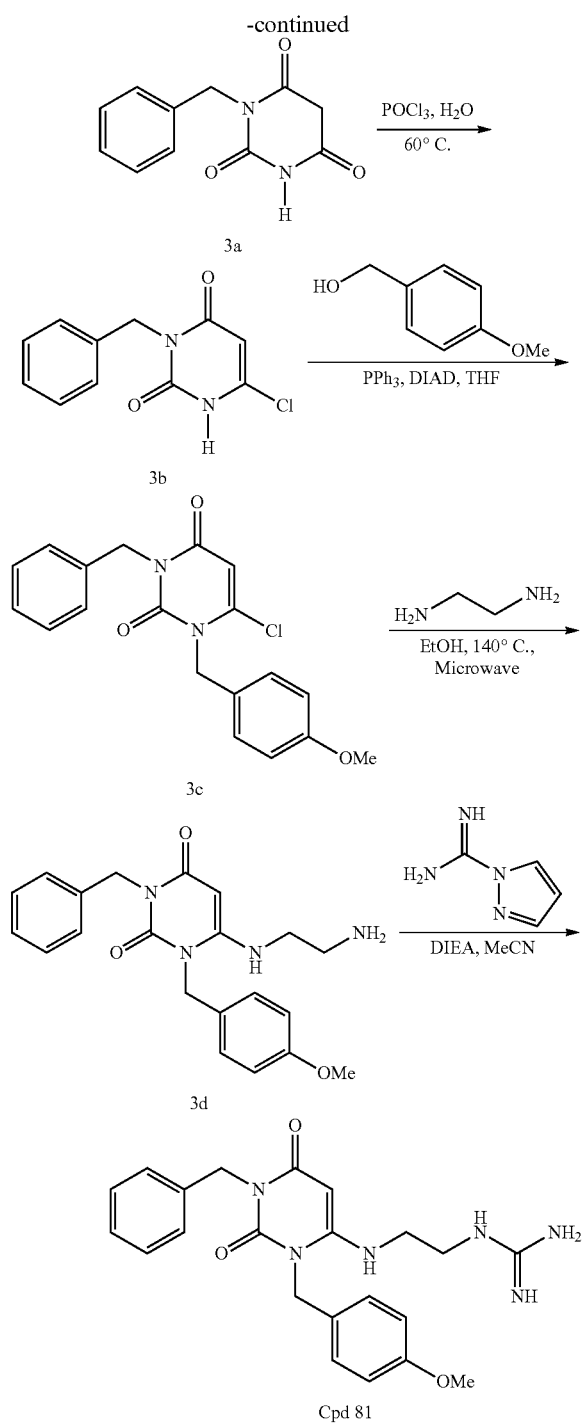

mL, 22 9 mmol) and the reaction mixture was cautiously treated with water (0.103 mL, 5.7 mmol). The solution was heated to 60° C. and was stirred overnight. The reaction mixture was then concentrated and the residue was poured over 2N NaOH (15 mL). The crude material was collected by vacuum filtration and purified by recrystallization from ethanol to afford Cpd 3b (60 mg) as a white powder. A second crop of 300 mg of crude 3b was recovered from the recrystallization and used in subsequent reactions without further purification. $^1$H NMR (MeOD, $d_4$). δ 5.04 (s, 2H), 5.87 (s, 1H), 7.25-7.38 (m, 5H).

C. 1-(4-Methoxylbenzyl)-6-chloro-3-benzyl uracil (Cpd 3c). A stirred solution of Cpd 3b (60 mg, 0.25 mmol) in THF was treated with 4-methoxybenzyl alcohol (35 mg, 0.25 mmol), triphenylphosphine (133 mg, 0.51 mmol) and diisopropyl azocarboxylate (51 mg, 0.25 mmol). The reaction was allowed to stir overnight at room temperature. The mixture was washed with water and extracted with ethyl acetate. Combined organic extracts were dried over $Na_2SO_4$, filtered and concentrated. The resultant residue was purified by Isco flash column chromatography (20% EtOAc-100 EtOAc in heptanes, 40 min) to afford Cpd 3c (60 mg) as a white powder. M$^+$ (ES+)=356.9.

D. 6-(2-Amino-ethylamino)-3-benzyl-1-(4-methoxybenzyl)-uracil (Cpd 3d). Cpd 3c (60 mg, 0.17 mmol) was dissolved in ethanol (3 mL) and the reaction mixture was treated with ethylenediamine (51 mg, 0.84 mmol). The solution was run at 140° C. for 20 min under power max conditions in a microwave reactor. The solution was washed with water and extracted with ethyl acetate. Combined organic phases were dried over $Na_2SO_4$, filtered and concentrated to give crude Cpd 3d (35 mg) as a yellow oil. The crude mixture was used in subsequent reactions without further purification.

E. N-{2-[1-Benzyl-3-(4-methoxy-benzyl)-2,6-dioxo-1,2,3,6-tetrahydro-pyrimidin-4-ylamino]-ethyl}-guanidine (Cpd 81). The title compound was prepared as described in Example 2, Step G. The crude material was purified by reverse phase preparative HPLC to give the title compound as its TFA salt (8.2 mg). M+ (ES+)=422.9. $^1$H NMR (MeOD, $d_4$). δ 3.19-3.24 (m, 4H), 3.67 (s, 3H), 4.77 (s, 1H), 4.99 (s, 2H), 5.03 (s, 2H), 6.77-6.80 (d, 2H, J=8.79 Hz), 7.01-7.04 (d, 2H, J=8.75 Hz), 7.12-7.25 (m, 5H).

Using the procedures of Example 3 and the appropriate reagents, starting materials and purification methods known to those skilled in the art, the following compounds of the present invention were prepared: compound 84.

Cpd 84:N-{2-[1,3-Bis-(4-methoxy-benzyl)-2,6-dioxo-1,2,3,6-tetrahydro-pyrimidin-4-ylamino]-ethyl}-guanidine (DMSO, $d_6$) δ 3.25-3.27 (m, 2H), 3.35-3.37 (m, 2H), 3.74 (s, 3H), 3.75 (s, 3H), 4.83 (s, 1H), 4.90 (s, 2H), 5.15 (s, 2H), 6.81-6.89 (m, 4H), 7.14-7.24 (m, 4H), 7.70 (s, 1H).

Example 4

N-{2-[5-(4-Fluoro-benzyl)-1-(4-methoxy-benzyl)-4,6-dioxo-1,4,5,6-tetrahydro-[1,3,5]triazin-2-ylamino]-ethyl}-N-(4-fluoro-phenyl)-guanidine (Cpd 119)

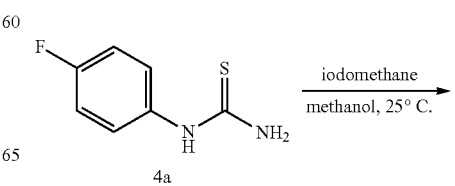

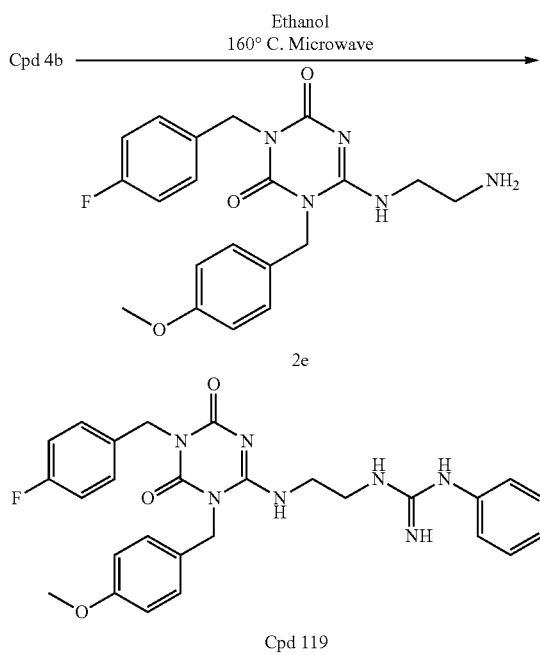

Cpd 90: N-(4-Cyano-phenyl)-N'-{2-[5-(4-fluoro-benzyl)-1-(4-methoxy-benzyl)-4,6-dioxo-1,4,5,6-tetrahydro-[1,3,5]triazin-2-ylamino]-ethyl}. $^1$H NMR (methanol-d$_4$): 7.74 (d, 2H, J=8.7 Hz), 7.44 (m, 2H), 7.35 (d, 2H, J=8.3 Hz), 7.21 (d, 2H, J=8.6 Hz), 7.01 (t, 2H, J=8.8 Hz), 6.88 (d, 2H, J=8.8 Hz), 5.11 (s, 2H), 5.02 (s, 2H), 3.75 (s, 3H), 3.61 (t, 2H, J=6.3 Hz), 3.51 (m, 2H); HRMS m/z (M+H)$^+$ calcd 543.2268, found 543.2273.

Cpd 104: N-{2-[5-(4-Fluoro-benzyl)-1-(4-methoxy-benzyl)-4,6-dioxo-1,4,5,6-tetrahydro-[1,3,5]triazin-2-ylamino]-ethyl}-N-pyridin-2-yl-guanidine. $^1$H NMR (DMSO-d$_6$): 10.90 (br, 1H), 9.78 (br, 1H), 8.65 (br, 2H), 8.17 (d, 1H, J=5.4 Hz), 8.07 (m, 1H), 7.87 (t, 1H, J=7.8 Hz), 7.33 (m, 2H), 7.13 (m, 4H), 7.05 (d, 1H, J=8.2 Hz), 6.78 (d, 2H, J=8.7 Hz), 4.98 (s, 2H), 4.86 (s, 2H), 3.67 (s, 3H), 3.54 (m, 2H), 3.36 (br, 2H); HRMS m/z (M+H)$^+$ calcd 519.2268, found 519.2253.

Cpd 118: N-{2-[5-(4-Fluoro-benzyl)-1-(4-methoxy-benzyl)-4,6-dioxo-1,4,5,6-tetrahydro-[1,3,5]triazin-2-ylamino]-ethyl}-N-(2-fluoro-phenyl)-guanidine. $^1$H NMR (methanol-d$_4$): 7.47-7.37 (m, 3H), 7.31 (t, 1H, J=7.8 Hz), 7.23 (m, 2H), 7.18 (d, 2H, J=8.6 Hz), 7.01 (t, 2H, J=8.8 Hz), 6.89 (d, 2H, J=8.8 Hz), 5.06 (s, 2H), 5.01 (s, 2H), 3.76 (s, 3H), 3.56 (t, 2H, J=6.3 Hz), 3.45 (t, 2H, J=6.3 Hz); HRMS m/z (M+H)$^+$ calcd 536.2222, found 536.2227.

Cpd 134: N-Benzoyl-N-{2-[5-(4-fluoro-benzyl)-1-(4-methoxy-benzyl)-4,6-dioxo-1,4,5,6-tetrahydro-[1,3,5]triazin-2-ylamino]-ethyl}-guanidine. $^1$H NMR (methanol-d$_4$): 7.93 (d, 2H, J=8.2 Hz), 7.70 (t, 1H, J=7.5 Hz), 7.57 (t, 2H, J=7.5 Hz), 7.41 (m, 2H), 7.16 (d, 2H, J=8.7 Hz), 6.97 (t, 2H, J=8.7 Hz), 6.85 (d, 2H, J=8.7 Hz), 5.08 (s, 2H), 4.99 (s, 2H), 3.70 (s, 3H), 3.66 (t, 2H, J=6.2 Hz), 3.55 (t, 2H, J=6.2 Hz); HRMS m/z (M+H)$^+$ calcd 546.2265, found 546.2259.

Example 5

N-{2-[5-Benzyl-1-(4-methoxy-benzyl)-4,6-dioxo-1,4,5,6-tetrahydro-[1,3,5]triazin-2-ylamino]-ethyl}-oxyguanidine (Cpd 27)

A. 1-(4-Fluoro-phenyl)-2-methyl-isothiourea (Cpd. 4b). To a solution of (4-Fluoro-phenyl)-thiourea (18.7 mg, 0.11 mmol) and methanol (0.25 mL) was added iodomethane (8 L, 0.13 mmol). The mixture was stirred at 25° C. for 16 h, then concentrated to a residue to provide crude compound 4b.

C. N-{2-[5-(4-Fluoro-benzyl)-1-(4-methoxy-benzyl)-4,6-dioxo-1,4,5,6-tetrahydro-[1,3,5]triazin-2-ylamino]-ethyl}-N'-(4-fluoro-phenyl)-guanidine (Cpd 127). To a solution of Compound 4b in ethanol (0.5 mL) was added Compound 2e (40 mg, 0.10 mmol). The mixture was irradiated in a microwave reactor at 160° C. for 15 min, then concentrated. The resulting residue was dissolved into dimethylsulfoxide and purified by reversed-phase chromatography to furnish the title compound 119 (18.3 mg, 0.024 mmol) as its TFA salt. $^1$H NMR (methanol-d$_4$): δ 7.42 (m, 2H), 7.24-7.12 (m, 6H), 7.00 (m, 2H), 6.89 (m, 2H), 5.06 (s, 2H), 5.01 (s, 2H), 3.75 (s, 3H), 3.56 (m, 2H), 3.43 (m, 2H); HRMS m/z (M+H)$^+$ calcd 536.2222, found 536.2227.

Using the procedures of Example 4 and the appropriate reagents, starting materials and purification methods known to those skilled in the art, the following compounds of the present invention were prepared: compounds 44, 53, 54, 58, 61, 62, 63, 64, 65, 66, 67, 70, 71, 72, 73, 74, 75, 76, 88, 89, 90, 91, 92, 103, 104, 105, 106, 107, 108, 114, 115, 116, 117, 118, 120, 121, 126, 127, 128, 133, 134, 135, 138, 139, and 140.

Cpd 58: N-{2-[5-(3,4-Dichloro-benzyl)-1-(4-methoxy-benzyl)-4,6-dioxo-1,4,5,6-tetrahydro-[1,3,5]triazin-2-ylamino]-ethyl}-N-isopropyl-guanidine. $^1$H NMR (methanol-d$_4$): 7.56 (s, 1H), 7.45 (d, 1H, J=8.3 Hz), 7.35 (d, 1H, J=8.3 Hz), 7.22 (d, 2H, J=8.3 Hz), 6.89 (d, 2H, J=8.4 Hz), 5.12 (s, 2H), 5.01 (s, 2H), 3.77 (s, 3H), 3.68 (m, 1H), 3.57 (t, 2H, J=6.3 Hz), 3.41 (t, 2H, J=6.3 Hz), 1.17 (d, 6H, J=6.5 Hz); HRMS m/z (M+H)$^+$ calcd 534.1787, found 534.1792.

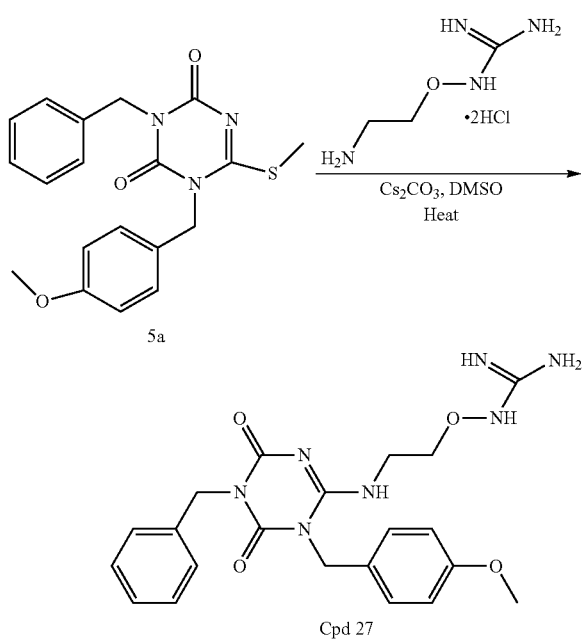

A. Compound 5a was prepared by the method described in Example 1, Step C, substituting phenyl methanol for 4-ethylbenzyl alcohol.

B. To 3-benzyl-1-(4-methoxy-benzyl)-6-methylsulfanyl-1H-[1,3,5]triazine-2,4-dione 5a (0.056 g, 0.15 mmol) in DMSO (1 mL) was added N-(2-amino-ethyl)-oxyguanidine dihydrochloride salt (0.058 g, 0.30 mmol) and $Cs_2CO_3$ (0.098 mg, 0.30 mmol). The reaction mixture was heated at 70° C. for 5 h and cooled to rt. N-(2-Amino-ethyl)-oxyguanidine dihydrochloride salt (0.058 g, 0.30 mmol) and $Cs_2CO_3$ (0.098 mg, 0.30 mmol) were again added and the resulting slurry stirred at 40° C. for 16 h. The reaction mixture was cooled to room temperature, loaded onto a 1g C-18 SPE cartridge, and eluted with $CH_3CN$. The eluant was concentrated and the resulting residue was purified by reverse-phase liquid chromatography using a gradient of 90:10 (acetonitrile:water, with 0.1% TFA) to 90:10 (acetonitrile:water, with 0.1% TFA) to give the title compound 27 (99% pure by HPLC, 0.0289 g). $^1$H NMR ($d^6$-DMSO/$CDCl_3$) δ 3.65-3.73 (2H, m), 3.78 (3H, s), 3.96-4.04 (2H, m), 5.01 (2H, s), 5.10 (2H, s), 6.85 (2H, d, J=8.7 Hz), 7.21-7.40 (7H. m), 7.74 (4H, bs); 7.89 (1H, m) 11.58 (1H, bs); HRMS calcd. for $C_{21}H_{26}N_7O_4$ m/z 440.2046 (M+H), found: 440.2030.

Using the procedures of Example 5 and the appropriate reagents, starting materials and purification methods known to those skilled in the art, the following compounds of the present invention were prepared: compound 10.

Example 6

4-[4-(2-Guanidino-ethylamino)-3-(4-methoxy-benzyl)-2,6-dioxo-3,6-dihydro-2H-[1,3,5]triazin-1-ylmethyl]-benzoic acid (Cpd 101)

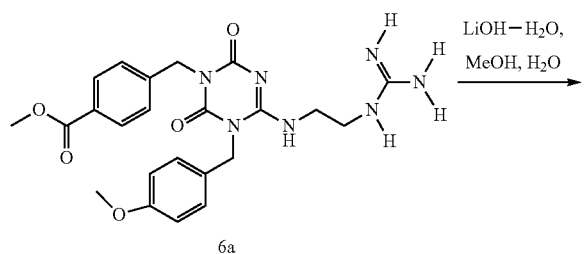

6a

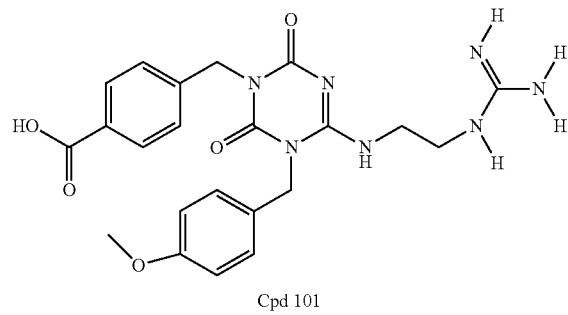

Cpd 101

A. Compound 6a was prepared according to the methods described in Example 1, and substituting 4-hydroxymethyl-benzoic acid methyl ester for 4-ethylbenzyl alcohol.

B. 4-[4-(2-Guanidino-ethylamino)-3-(4-methoxy-benzyl)-2,6-dioxo-3,6-dihydro-2H-[1,3,5]triazin-1-ylmethyl]-benzoic acid (Cpd. 101). A mixture of compound 6a (20 mg, 0.028 mmol) and lithium hydroxide (6 mg, 0.014 mmol) in 5 mL of MeOH and 1 mL of $H_2O$ was allowed to stir overnight at room temperature. At that time, an additional 6 mg of lithium hydroxide was added and the mixture stirred for and additional 18 h. The mixture was then concentrated and purified by HPLC. The title compound 101 was obtained as its TFA salt (10 mg, 0.014 mmol). $^1$H NMR (DMSO-$d_6$) δ 3.26 (m, 2H), 3.40 (m, 2H), 3.68 (s, 3H), 4.97 (s, 2H), 5.02 (s, 2H), 6.79-6.82 (d, 2H, J=8.7 Hz), 7.06-7.09 (d, 2H, J=8.7 Hz), 7.35-7.38 (d, 2H, J=8.2 Hz), 7.86-7.88 (d, 2H, J=8.3 Hz).

Example 7

N-{2-[5-(4-Hydroxy-benzyl)-1-(4-methoxy-benzyl)-4,6-dioxo-1,4,5,6-tetrahydro-[1,3,5]triazin-2-ylamino]-ethyl}-guanidine (Cpd 110)

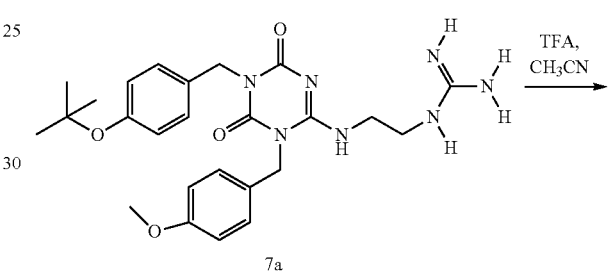

7a

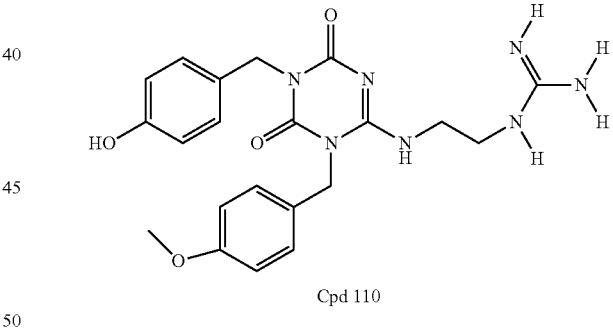

Cpd 110

A. Compound 7a was prepared according to the methods described in Example 1, and substituting (4-tert-butoxy-phenyl)-methanol) for 4-ethylbenzyl alcohol.

B. N-{2-[5-(4-Hydroxy-benzyl)-1-(4-methoxy-benzyl)-4,6-dioxo-1,4,5,6-tetrahydro-[1,3,5]triazin-2-ylamino]-ethyl}-guanidine (Cpd 110). The crude Compound 7a (assumed to be about 0.24 mmol) was dissolved in $CH_3CN$. To this mixture was added 3 mL of TFA. The resulting mixture was allowed to stir overnight at room temperature. The mixture was concentrated and purified by HPLC to give the title compound 110 as its TFA salt (31 mg, 0.046 mmol). $^1$H NMR (DMSO-$d_6$) δ 1.25-1.28 (m, 1H), 3.28-2.31 (m, 2H), 3.31-3.36 (m, 2H), 3.73 (s, 3H), 4.78 (s, 2H), 4.98 (s, 2H), 6.65-6.68 (d, 2H, J=8.4 Hz), 6.89-6.91 (d, 2H, J=8.7 Hz), 7.11-7.14 (d, 2H, J=8.6 Hz), 7.52-7.54 (d, 2H, J=5.5 Hz), 7.99 (m, 1H).

Example 8

N-{2-[1-(4-Methoxy-benzyl)-5-(4-nitro-benzyl)-4,6-dioxo-1,4,5,6-tetrahydro-[1,3,5]triazin-2-ylamino]-ethyl}-guanidine (Cpd 95)

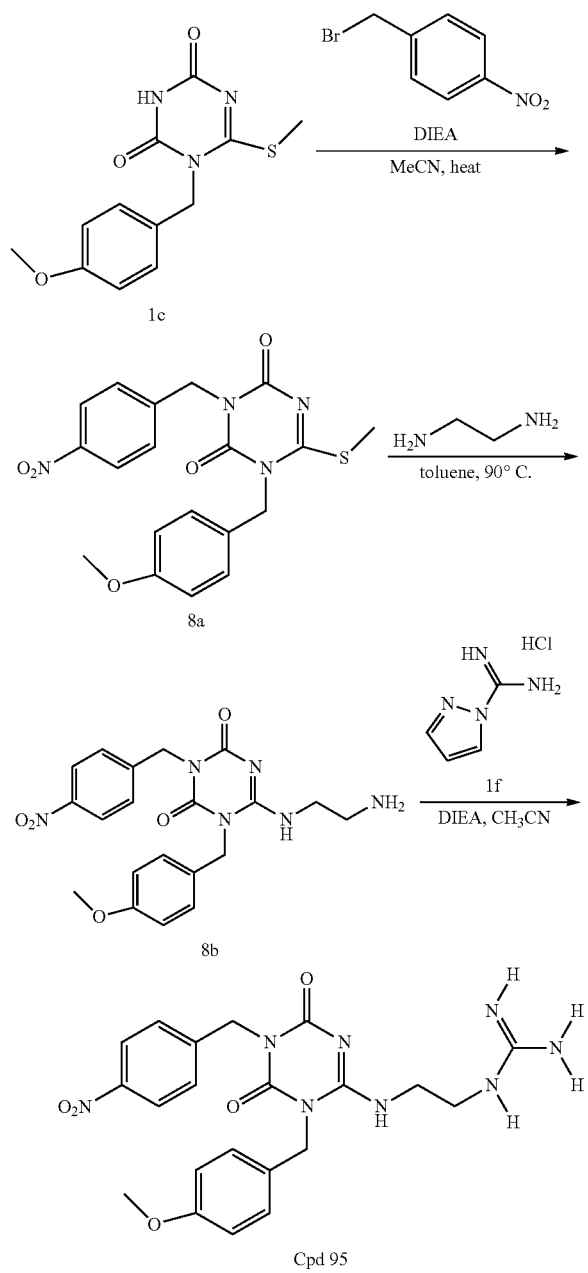

A. 1-(4-Methoxy-benzyl)-6-methylsulfanyl-3-(4-nitrobenzyl)-1H-[1,3,5]triazine-2,4-dione (Cpd 9a). Compound 1c (200 mg, 0.73 mmol) was dissolved in CH₃CN and was treated with 4-nitrobenzyl bromide (168 mg, 0.86 mmol) and 80 L (0.73 mmol) of diisopropylethylamine The resulting mixture was heated to 87° C. and allowed to stir overnight. The reaction mixture was cooled to room temperature, diluted with ethyl acetate, and washed with saturated sodium bicarbonate solution. The organic phase was dried over MgSO₄, filtered, and concentrated. The residue was purified by flash chromatography to give compound 8a (44 g, 0.36 mmol).

B. 6-(2-Amino-ethylamino)-1-(4-methoxy-benzyl)-3-(4-nitro-benzyl)-1H-[1,3,5]triazine-2,4-dione (Cpd. 9b). To compound 8a (80 mg, 0.19 mmol) in 10 mL of toluene was added an excess of ethylene diamine (64 L, 0.95 mmol). The resulting mixture was heated to 90° C. for 26 h. The mixture was taken up in ethyl acetate and washed with water. The organic layer was separated, dried over MgSO₄ and concentrated. The crude product 8b (79 mg, 0.18 mmol, 97% yield) was used in the next step without further purification.

C. N-{2-[1-(4-Methoxy-benzyl)-5-(4-nitro-benzyl)-4,6-dioxo-1,4,5,6-tetrahydro-[1,3,5]triazin-2-ylamino]-ethyl}-guanidine (Cpd 95). A mixture of compound 8b (51 mg, 0.12 mmol), 1H-pyrazole1-carboxamidine hydrochloride (18 mg, 0.12 mmol), and diisopropylethylamine (26 μL, 0.36 mmol) in 10 mL of acetonitrile was allowed to stir at room temperature for several days. The resulting mixture was concentrated and purified by liquid chromatography. The title compound 95 was obtained as a white powder (17 mg, 0.036 mmol) and was submitted as a TFA salt. ¹H NMR (DMSO-d₆) δ 3.65-3.71 (m, 4H), 3.85 (s, 3H), 5.30 (bm, 4H), 6.99-7.02 (m, 2H), 7.26-7.30 (m, 2H), 7.54-7.60 (m, 2H), 8.02-8.20 (bs, 1H), 8.25 (m, 2H).

Using the procedures of Example 8 and the appropriate reagents, starting materials and purification methods known to those skilled in the art, the following compounds of the present invention were prepared: compounds 42, 43, 47, 55, 56, 59, 94, 97, 98, 99, 100, 102, and 113.

Example 9

N-{2-[5-(4-Amino-benzyl)-1-(4-methoxy-benzyl)-4,6-dioxo-1,4,5,6-tetrahydro-[1,3,5]triazin-2-ylamino]-ethyl}-guanidine (Cpd 125)

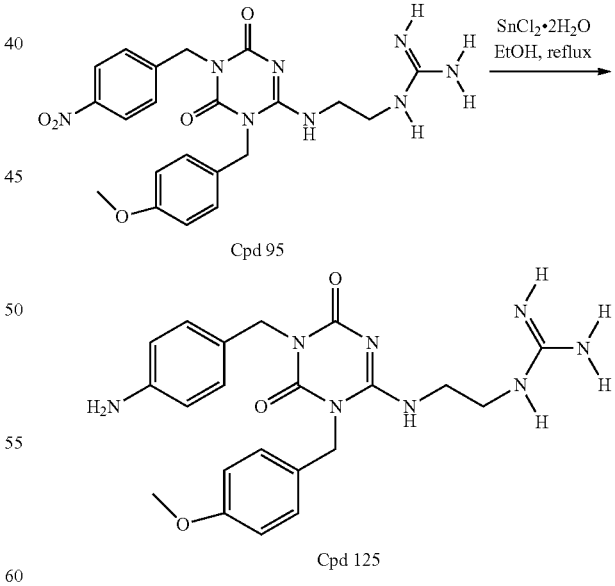

A mixture of the crude Compound 95 (39 mg, 0.083 mmol) and tin(II)chloride dihydrate (94 mg, 0.42 mmol) in 20 mL of EtOH was heated to reflux for 24 h. The solution was concentrated and the residue was purified by HPLC to give the title compound 125 as its TFA salt (6.5 mg, 0.015 mmol). ¹H NMR (DMSO-d₆) δ 3.30 (m, 4H), 3.73 (s, 3H), 4.80 (s, 2H), 4.98 (s, 2H), 6.56-6.78 (m, 2H), 6.88-6.91 (d, 2H, J=8.6 Hz), 7.13-7.20 (m, 4H), 7.43-7.47 (m, 1H), 7.92-7.99 (m, 1H).

Using the procedures of Example 9 and the appropriate reagents, starting materials and purification methods known to those skilled in the art, the following compounds of the present invention were prepared: compound 96.

Example 10

3-(3,4-Dichloro-benzyl)-6-[2-(2-imino-imidazolidin-1-yl)-ethylamino]-1-(4-methoxy-benzyl)-1H-[1,3,5]triazine-2,4-dione (Cpd 60)

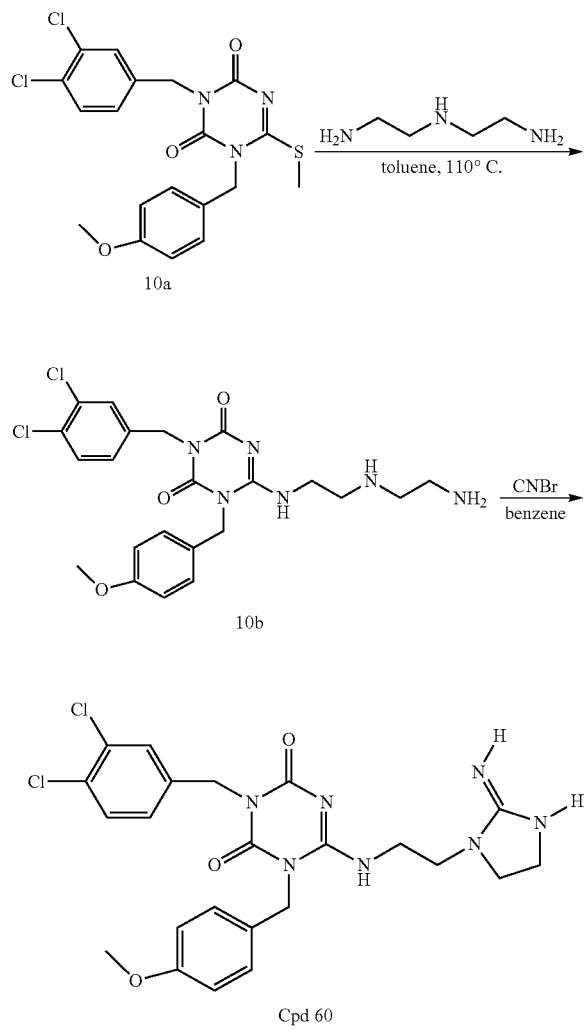

Cpd 60

A. Compound 10a was prepared according to the methods described in Example 1, Step C, and substituting (3,4-dichloro-phenyl)-methanol for 4-ethylbenzyl alcohol.

B. 6-[2-(2-Amino-ethylamino)-ethylamino]-3-(3,4-dichloro-benzyl)-1-(4-methoxy-benzyl)-1H-[1,3,5]triazine-2,4-dione (Cpd 10b). To compound 10a (0.400 g, 0.968 mmol) in toluene (6 mL) was added 2,2'-diaminodiethylamine (0.300 g, 2.9 mmol) and the reaction mixture was heated at 110° C. for 4 h. The reaction mixture was cooled to room temperature and then water was added. The mixture was extracted with ethyl acetate, dried over sodium sulfate, filtered, and concentrated to give compound 10b (0.46 g) which was used in the subsequent reaction without further purification.

C. 3-(3,4-Dichloro-benzyl)-6-[2-(2-imino-imidazolidin-1-yl)-ethylamino]-1-(4-methoxy-benzyl)-1H-[1,3,5]triazine-2,4-dione. (Cpd 60). To compound 10b (0.100 g, 0.203 mmol) in benzene (2 mL) was added cyanogen bromide (0.022 g, 0.203 mmol). The reaction mixture was stirred for 2.5 h at room temperature. The reaction mixture was concentrated and then dissolved in a mixture of acetonitrile and methanol. The mixture was purified by reverse-phase chromatography to yield the title compound 60 (0.017 g). $^1$H NMR (DMSO-$d_6$) δ 3.28-3.59 (8H, m), 3.66 (3H, s), 4.83 (2H, s), 4.92 (2H, s), 6.81-6.84 (2H, d, J=8.7 Hz), 7.09-7.12 (2H, d, 8.7 Hz), 7.19-7.22 (1H, d, J=8.3 Hz), 7.46 (1H,s), 7.51-7-54 (1H, d, J=8.3 Hz), 7.86-7.95 (3H, m).

Example 11

N-{2-[1-(4-Hydroxy-benzyl)-5-(4-methoxy-benzyl)-4,6-dioxo-1,4,5,6-tetrahydro-[1,3,5]triazin-2-ylamino]-ethyl}-guanidine (Cpd 143)

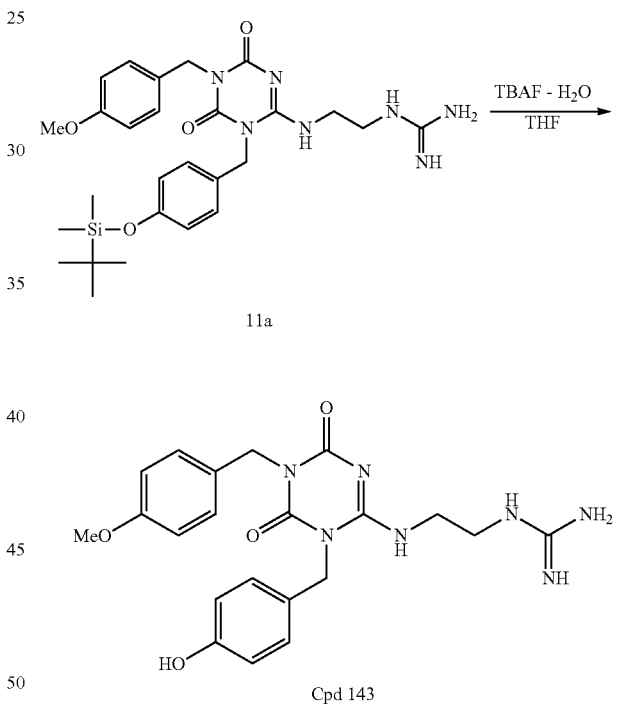

Cpd 143

A. Compound 11a (50 mg, 0.09 mmol) was prepared according to the methods described in Example 2, and substituting [4-(tert-butyl-dimethyl-silanyloxy)-phenyl]-methanol for 4-methoxybenzyl alcohol in Step D.

B. Compound 11a was suspended in THF (2 mL) and the reaction mixture was treated with tetrabutylammonium fluoride monohydrate (24 mg, 0.09 mmol). The solution was stirred at room temperature overnight. The mixture was then concentrated under nitrogen and the residue was purified by reverse phase preparative HPLC to give the title compound 143 (3.8 mg) as a white solid. M+(ES+)=440.1; $^1$H NMR (MeOD, $d_4$). 3.32 (m, 2H), 3.50 (t, 2H, J=7.08 Hz), 3.78 (s, 3H), 4.99 (s, 2H), 5.03 (s, 2H), 6.77 (d, 2H, J=8.58 Hz), 6.85 (d, 2H, J=8.71 Hz), 7.07 (d, 2H, J=8.62 Hz), 7.36 (d, 2H, J=8.67 Hz).

Example 12

N-{2-[1-(4-Amino-benzyl)-5-(4-chloro-benzyl)-4,6-dioxo-1,4,5,6-tetrahydro-[1,3,5]triazin-2-ylamino]-ethyl}-guanidine (Cpd 122)

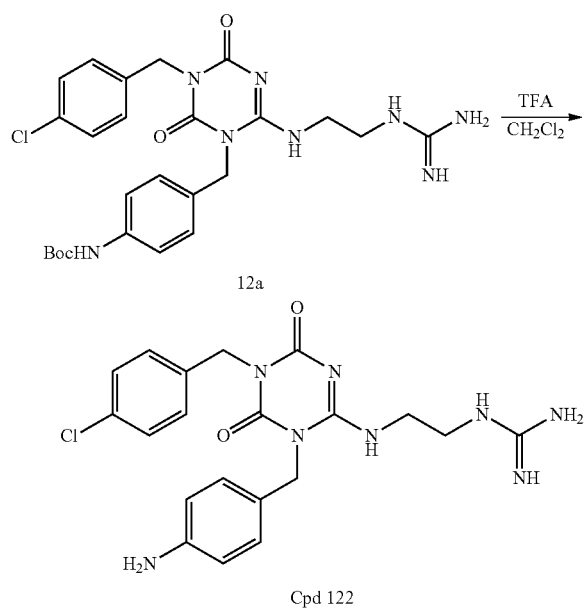

A. Compound 12a (50 mg, 0.09 mmol) was prepared according to the methods described in Example 2, and substituting (4-hydroxymethyl-phenyl)-carbamic acid tert-butyl ester for 4-methoxybenzyl alcohol in Step D.

B. Compound 12a (70 mg, 0.129 mmol) was suspended in dichloromethane (3 mL) and the solution was treated with trifluoroacetic acid (0.5 mL). The reaction was allowed to stir overnight at room temperature. The mixture was concentrated under nitrogen and the residue was purified by reverse phase preparative HPLC to give the title compound 122 (35.9 mg) as a white solid. M+(ES+)=443.1; $^1$H NMR (DMSO, d$_6$). δ 3.18-3.25 (m, 2H), 3.28-3.31 (m, 2H), 4.76 (s, 2H), 4.82 (s, 2H), 4.88 (s, 2H), 6.75 (d, 2H, J=8.25 Hz), 7.02 (d, 2H, J=8.38 Hz), 7.22-7.32 (m, 4H), 7.53 (d, 2H, J=4.02 Hz), 7.95 (m, 1H).

Example 13

N-{2-[5-(3,4-Dichloro-benzyl)-1-(4-methoxy-benzyl)-4,6-dioxo-1,4,5,6-tetrahydro-[1,3,5]triazin-2-ylamino]-ethyl}-N'-cyano-guanidine (Cpd 28)

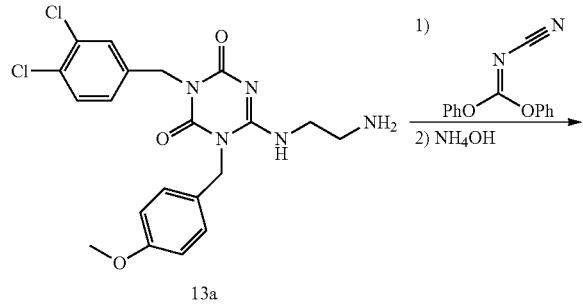

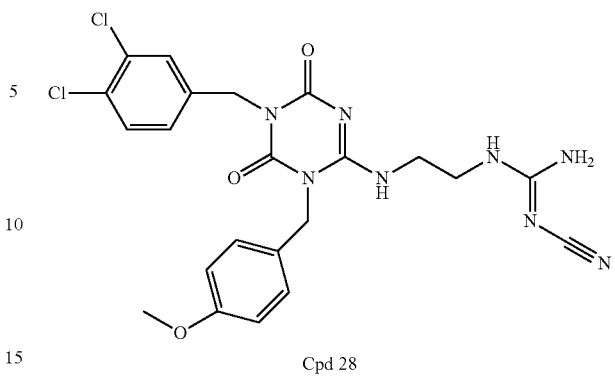

A. Compound 13a was prepared according to Example 1, substituting 3,4-dichlorophenyl methanol for 4-ethylbenzyl alcohol in Step D.

B. To a mixture of Cpd 13a (0.050 g, 0.11 mmol) in isopropyl alcohol (1 mL) was added triethylamine (0.017 mL, 0.12 mmol) and diphenyl N-cyanocarbonimidate (0.029 g, 0.12 mmol). The reaction mixture was stirred for 2 h at room temperature then concentrated under vacuum. The resulting residue was suspended in EtOH (0.75 mL) and NH$_4$OH (0.25 mL, 14.8 N (aq)) was added. The reaction mixture was stirred for 16 h at 50° C., concentrated under vacuum, and the resulting residue was purified by reverse-phase liquid chromatography using a gradient of 90:10 (water:acetonitrile, with 0.1% TFA) to 90:10 (acetonitrile:water, with 0.1% TFA) to give the title compound 28 (99% pure by HPLC, 0.0017 g); HRMS calcd. for $C_{22}H_{23}Cl_2N_8O_3$ m/z 517.1270 (M+H), found: 517.1281.

Using the procedures of Example 13 and the appropriate reagents, starting materials and purification methods known to those skilled in the art, the following compounds of the present invention were prepared: compound 143.

Example 14

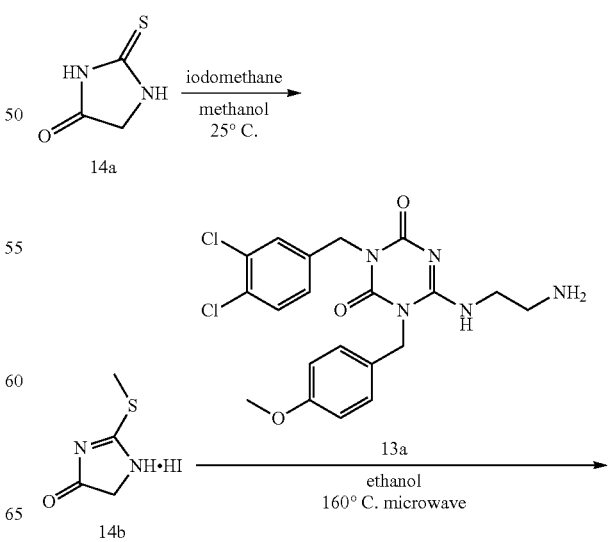

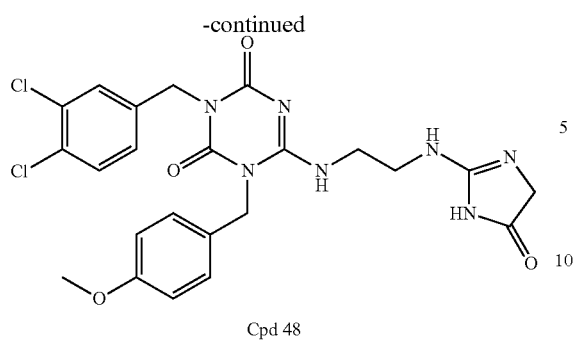

Cpd 48

A. 1,5-Dihydro-2-(methylthio)-4H-imidazol-4-one monohydriodide (Cpd 15b). To a solution of compound 14a (420 mg, 3 6 mmol) in EtOH (5 mL) was added iodomethane (0.268 mL, 4.3 mmol). The mixture was stirred at 25° C. for 16 h, then concentrated to a residue to provide compound 14b, which was used in the next reaction without further purification.

B. 3-(3,4-Dichloro-benzyl)-1-(4-methoxy-benzyl)-6-[2-(5-oxo-4,5-dihydro-1H-imidazol-2-ylamino)-ethylamino]-1H-[1,3,5]triazine-2,4-dione 4 (Cpd 52). To a solution of compound 14b (0.0373 mg, 0.14 mmol) in ethanol (0.75 mL) was added compound 13a (50 mg, 0.13 mmol). The mixture was irradiated (wave) at 160° C. for 15 min, concentrated, and the resulting residue was purified by reverse-phase liquid chromatography using a gradient of 90:10 (water: acetonitrile, with 0.1% TFA) to 90:10 (acetonitrile:water, with 0.1% TFA) to give the title compound 48 (89% pure by HPLC, 0.0025 g). HRMS calcd. for $C_{23}H_{24}Cl_2N_7O_4$ m/z 532.1267 (M+H), found: 532.1257.

Example 15

3-(3,4-Dichloro-benzyl)-6-[2-(4,5-dihydro-1H-imidazol-2-ylamino)-ethylamino]-1-(4-methoxy-benzyl)-1H-[1,3,5]triazine-2,4-dione (Cpd 49)

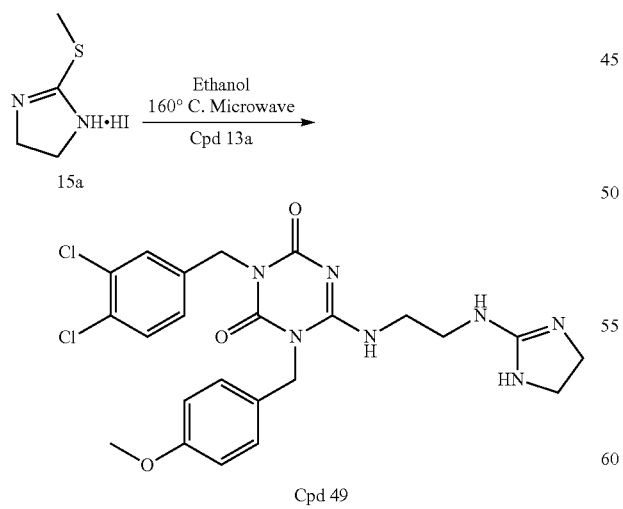

Cpd 49

To a solution of compound 15a (0.054 mg, 0.22 mmol) in ethanol (1 mL) was added compound 13a (50 mg, 0.11 mmol). The mixture was irradiated in a microwave reactor at 160° C. for 15 min, concentrated, and the resulting residue was purified by reverse-phase liquid chromatography using a gradient of 90:10 (water:acetonitrile, with 0.1% TFA) to 90:10 (acetonitrile: water, with 0.1% TFA) to give the title compound 49 (93% pure by HPLC, 0.0082 g). HRMS calcd. for $C_{23}H_{26}Cl_2N_7O_3$ m/z 518.1474 (M+H), found: 518.1479.

Example 16

N-{2-[5-(4-Fluoro-benzyl)-1-(4-methoxy-benzyl)-4,6-dioxo-1,4,5,6-tetrahydro-[1,3,5]triazin-2-ylamino]-ethyl}-N-amino-guanidine (Cpd 93)

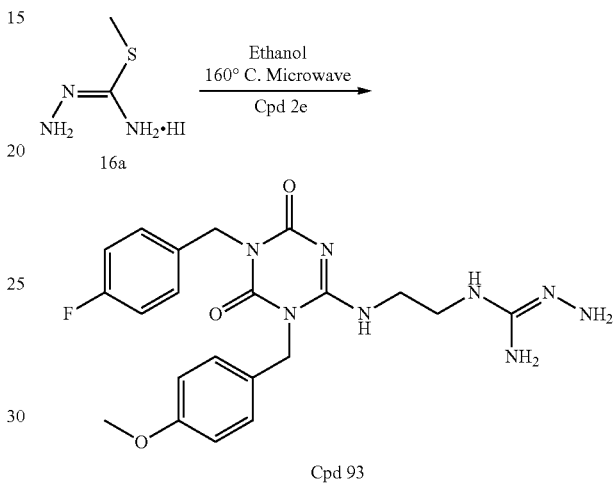

Cpd 93

To a solution of compound 16a (0.061 mg, 0.22 mmol) in ethanol (1 mL) was added compound 2e (50 mg, 0.13 mmol). The mixture was irradiated in a microwave reactor at 160° C. for 15 min, concentrated, and the resulting residue was purified by reverse-phase liquid chromatography using a gradient of 90:10 (water:acetonitrile, with 0.1% TFA) to 90:10 (acetonitrile:water, with 0.1% TFA) to give the title compound 93 (99% pure by HPLC, 0.018 g). $^1$H NMR (CDCl$_3$) 3.22-3.73 (2H, m), 3.38-3.55 (2H, m), 3.75 (2H, t, J=5.8 Hz), 3.77 (3H, s), 5.01 (2H, s), 5.07 (2H, s), 5.44-4.86 (2H, bs), 6.83 (2H, d, J=8.7Hz), 6.90-7.03 (2H, m), 7.16 (2H, d, J=8.7Hz), 7.48-7.36 (2H, m). HRMS calcd. for $C_{21}H_{26}FN_8O_3$ m/z 457.2112 (M+H), found: 457.2101.

Example 17

N-{2-[5-(4-fluoro-benzyl)-1-(4-methoxy-benzyl)-4,6-dioxo-1,4,5,6-tetrahydro-[1,3,5]triazin-2-ylamino]-ethyl}-N'-boc-guanidine (Cpd 132)

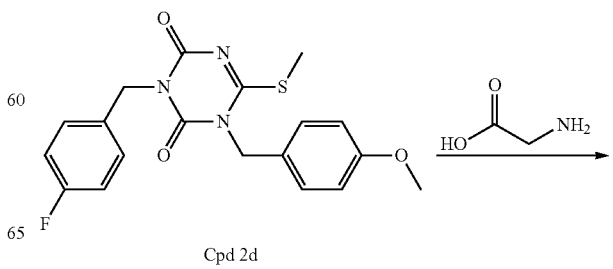

Cpd 2d

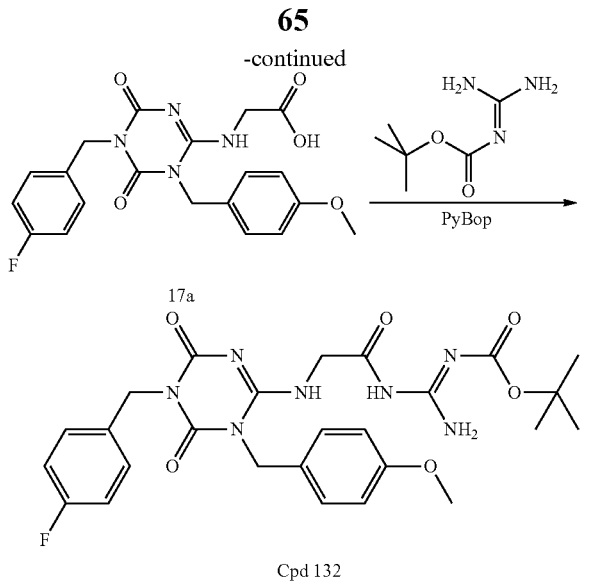

A. [5-(4-Fluoro-benzyl)-1-(4-methoxy-benzyl)-4,6-dioxo-1,4,5,6-tetrahydro-[1,3,5]triazin-2-ylamino]-acetic acid (Cpd 17a). To a solution of compound 2d (0.10 g, 0.26 mmol) in ethanol (1 mL) was added glycine (0.056 g, 0.75 mmol) and DIEA (0.143 mL, 0.82 mmol). The mixture was irradiated in a microwave reactor at 150° C. for 30 min then cooled to rt. Glycine (0.056 g, 0.75 mmol) and DIEA (0.143 mL, 0.82 mmol) were again added and the resulting mixture was irradiated (wave) at 150° C. for 30 min, cooled to rt, concentrated, and the resulting residue was purified by reverse-phase liquid chromatography using a gradient of 90:10 (water:acetonitrile, with 0.1% TFA) to 90:10 (acetonitrile:water, with 0.1% TFA) to give compound 17a (99% pure by HPLC, 0.058 g). MS calcd. for $C_{20}H_{20}FN_4O_5$ m/z 415.1 (M+H), found: 415.1.

B. N-{2-[5-(4-fluoro-benzyl)-1-(4-methoxy-benzyl)-4,6-dioxo-1,4,5,6-tetrahydro-[1,3,5]triazin-2-ylamino]-ethyl}-N'-boc-guanidine (Cpd 132). To a solution of compound 17a (0.025 g, 0.047 mmol), DIEA (0.032 mL, 0.18 mmol), and monobocguanidine (0.015 g, 0.091 mmol) in DMF (0.40 mL) was added PyBop (0.047 g, 0.091 mmol). The mixture was stirred for 16 h at rt, quenched with water (3 mL), and the resulting solution was extracted 4×1 mL EtOAc. The combined organic layers were dried over $Na_2SO_4$, concentrated, and the resulting residue was purified by normal-phase flash chromatography on silica gel using a gradient of 50:50 (EtOAc:Heptane, with 0.1% $Et_3N$) to EtOAc (with 0.1% $Et_3N$) to give the title compound 132 (85% pure by HPLC, 0.0263 g). $^1$H NMR (CDCl$_3$) 1.46 (9H, s), 3.79 (3H, s), 4.05 (2H, s), 5.07 (4H, s), 6.90 (2H, d, J=8.7 Hz), 6.98 (2H, at, J=6.7 Hz), 7.30 (2H, d, J=8.7 Hz), 7.50 (2H, dd, J=8.7 and 8.6 Hz), 8.61 (1H, bs); MS calcd. for $C_{26}H_{31}FN_7O_6$ m/z 556.2320 (M+H), found: 556.2341.

BIOLOGICAL EXAMPLES

Biological Example 1

Expression, Isolation, and Purification of Prokineticin-1

Recombinant N-terminal FLAG-tagged human PK1 (SEQ ID NO 1: MRGATRVSIMLLLVTVSDCDYKD-DDDKAVITGACERDVQCGAGTCCAISLWL RGLRM-CTPLGREGEECHPGSH-KVPFFRKRKHHTCPCLPNLLCSRFPDGRYRCS MDLKNINF) was expressed in stably transfected HEK 293 cells.

HEK 293 cells were grown to 100% confluence in DMEM selective high-glucose media (Invitrogen, Carlsbad, Calif.) containing 10% FBS, 20 mM HEPES, sodium pyruvate, penicillin and streptomycin (50 μmg/ml each), and G418 (400 mg/L). The DMEM media used to culture the HEK 293 cells was replenished every other day with fresh media over a two-week period of time. Culture media containing the PK1 peptide was collected, and filtered in 500 mL 0.2 μm pore size filters (Corning Incorporated, Corning, N.Y.). The filtrate was stored in a filtrate bottle at 4° C. The PK1 peptide containing media was purified by gravity flow passage of media over M2 agarose columns (Sigma Chemical, St. Louis, Mo.) at 4° C. Following media passage, the agarose columns were washed with sterile 1× PBS (pH 7.4) until protein could no longer be detected by OD 280 nm. Columns were then eluted with a 0.1 M glycine-HCl solution at pH 2.8. The eluted material was immediately neutralized, by collecting into tubes containing 1M Tris pH8. Peak fractions were identified by OD 280 and pooled. The pooled fractions were subjected to Enterokinase cleavage of Flag epitope 4 units/mL overnight at room temperature. Enterokinase was removed, and sample aliquot was stored at −80° sC.

Results of Mass Spectral Analysis of PK1 Ligand From Above Purification.

The samples were analyzed using Maldi TOF-MS and LC-Electrospray-Mass Spectral Analysis.
Desired Protein Sequence:

SEQ ID NO 2:
AVITGACERDVQCGAGTCCAISLWLRGLRMCTPLGREGEECHPGSHKVP

FFRKRKHHTCPCLPNLLCSRFPDGRYRCSMDLKNINF

Calculated Avg. Molecular Mass=9667.4.
MALDI-TOF Analysis
Sample Preparation

The protein sample solution (10 μL) was desalted using a C4 Zip Tip according to the User Guide for Reversed-Phase ZipTip, 2002 Millipore Corporation.
Mass Spectrometry A Micromass TOF Spec E mass spectrometer was used to determine molecular mass. MassLynx software 3.4 was used for the system control and data acquisition. MALDI positive ion mass spectra were acquired over a mass range of 0-80,000 Da. The raw MS data were baseline subtracted and smoothed using Masslynx software and compared to the masses obtained from a reference standard.

Masses of eluting components were calculated using the Agilent deconvolution software.

Results

The mass spectral data shows the presence of the desired protein (molecular mass=9667) and an additional related component with a measured molecular mass of 9172 in about the same abundance based on mass spectral response. This mass agrees, within measurement error, with a possible truncation product missing the last four C-terminal residues indicated below.
Proposed Additional Protein Component Sequence

SEQ ID NO 3:
AVITGACERDVQCGAGTCCAISLWLRGLRMCTPLGREGEECHPGSHKVP

FFRKRKHHTCPCLPNLLCSRFPDGRYRCSMDLK

Calculated Avg. Molecular Mass=9178.8.

No other related protenaceous components were detected. The mass accuracy for all measurements is approximately 0.1%.

Biological Example 2

Functional Assay

Screening Procedure for PK1 Antagonists on the Fluorometric Imaging Plate Reader (FLIPR)

At a time of 24 h prior to running the assay, in cell culture media (DMEM containing high Glucose and L-glutamine, 10% FBS, 1% Pen/Streptomycin, 1% Sodium Pyruvate, 20 mM HEPES, Zeocin 200 mg/L), 100 µL of 1.3*10$^6$/ml HEK 293 GPR73 (PK1 receptor) expressing cells were plated in a 96 well poly-d-lysine coated plate (Costar), and incubated at 37° C. and 5% $CO_2$. On the day in which the assay was run, the media was removed and 200 µL of 5× Calcium Plus Dye (Molecular Devices) which was previously resuspended with 200 mL of assay buffer [HBSS w/$Ca^{2+}$ and $Mg^{2+}$ w/o phenol red, 20 mM HEPES, 0.1% BSA, 10 mL probenecid (710 mg probenecid in 5 mL of 1N NaOH, to which was then added 5 mL HBSS containing 20 mM HEPES)] was added to each well of the 96-well plate. The plate was incubated at 37° C. and 5% $CO_2$ for 30 min in dark. The plate was removed and allowed to reach RT for 15 min in the dark. The assay was then run on the FLIPR. In Brief: base line read for 1 min, compound added (25 µL) and incubated for 4 min, 15 seconds, PK1 ligand preparation added (25 µL) for a final concentration of a previously determined $EC_{50}$ and fluorescence was counted for 1 min, 45 seconds. Baseline is described as the amount of relative fluorescence read when buffer alone is added to cells. Baseline was subtracted from all wells. Percent of control was calculated as follows:

(Baseline subtracted well value is divided by baseline subtracted max value)*100.

Percent inhibition is 100 minus the percent of control value.

The $IC_{50}$ is defined as the amount of a given compound required to inhibit 50% of the maximum signal that is generated by the concentration of PK1 preparation used in our assay. $IC_{50}$ values were calculated using GraphPad Prism.

Table 2 includes data generated from the PK1 functional assay described in Example 2.

Biological and Mass Spectral Data

TABLE 2

| Cpd | $Ca^{2+}$ Mobilization $IC_{50}$ (µM) | $Ca^{2+}$ Mobilization % Inh @10 µM | MS obs | MS calc |
|---|---|---|---|---|
| 1 | >10 | 30 | 411.9 | 412.19 |
| 2 | 0.125, 0.363, 0.927* | 92, 85, 74 | 424.3 | 424.21 |
| 3 | 4.96 | 52 | 452.0 | 452.20 |
| 4 | 2.5 | 71 | 438.0 | 438.23 |
| 5 | 2.18 | 67 | 390.1 | 390.23 |
| 6 | 2.59 | 59 | 414.0 | 414.19 |
| 7 | >10 | 52 | 462.0 | 462.19 |
| 8 | 3.85 | 64 | 450.1 | 450.26 |
| 9 | >10 | 35 | 438.9 | 439.18 |
| 10 | >10 | 33 | 440.2 | 440.20 |
| 11 | >10 | 32 | 395.2 | 395.19 |
| 12 | 0.034, 0.082, 0.247* | 97, 96, 90 | 438.3 | 438.23 |
| 13 | 0.104, 0.256 | 92, 91 | 460.2 | 460.19 |
| 14 | >10 | 41 | 465.9 | 466.26 |
| 15 | 6.11 | 55 | 461.9 | 462.19 |

TABLE 2-continued

| Cpd | $Ca^{2+}$ Mobilization $IC_{50}$ (µM) | $Ca^{2+}$ Mobilization % Inh @10 µM | MS obs | MS calc |
|---|---|---|---|---|
| 16 | 0.836 | 77 | 442.0 | 442.20 |
| 17 | 0.014, 0.033, 0.087* | 100, 99, 97 | 442.0 | 442.20 |
| 18 | 0.007, 0.028, 0.041* | 98, 101, 99 | 492.0 | 492.13 |
| 19 | 0.862 | 81 | 477.8 | 478.18 |
| 20 | 3.69 | 61 | 454.0 | 454.22 |
| 21 | >10 | 43 | 454.0 | 454.22 |
| 22 | 0.947 | 80 | 436.9 | 437.21 |
| 23 | 1.25 | 74 | 450.9 | 451.22 |
| 24 | 0.041 | 99 | 456.0 | 456.22 |
| 25 | 0.137 | 94 | 437.9 | 438.23 |
| 26 | 0.354 | 88 | 437.9 | 438.23 |
| 27 | 1.97 | 55 | 508.2 | 508.13 |
| 28 | 0.71 | 101 | 517.1 | 517.13 |
| 29 | 0.042, 0.047 | 101, 102 | 505.8 | 506.15 |
| 30 | 0.009, 0.019 | 101, 103 | 457.8 | 458.17 |
| 31 | 0.009, 0.021 | 101, 102 | 453.9 | 454.22 |
| 32 | 0.601, 0.781 | 88, 86 | 519.7 | 520.16 |
| 33 | 2.86 | 66 | 455.9 | 456.22 |
| 34 | 0.515 | 89 | 519.7 | 520.16 |
| 35 | 0.061, 0.097, 0.113* | 100, 101, 101 | 519.7 | 520.16 |
| 36 | 1.32 | 77 | 545.8 | 546.18 |
| 37 | 0.038, 0.201, 0.326* | 98, 100, 98 | 507.7 | 508.11 |
| 38 | 0.055, 0.178, 0.194* | 98, 94, 98 | 489.7 | 490.15 |
| 39 | 0.909 | 81 | 457.8 | 458.17 |
| 40 | 0.248 | 98 | 545.7 | 546.10 |
| 41 | 0.027, 0.064 | 101, 99 | 527.7 | 528.11 |
| 42 | 0.281 | 92 | 545.8 | 546.18 |
| 43 | >10 | 31 | 547.8 | 546.18 |
| 44 | 0.011 | 100 | 506.1 | 506.15 |
| 45 | 0.018 | 103 | 469.8 | 470.20 |
| 46 | 0.058 | 101 | 452.0 | 452.24 |
| 47 | 0.057 | 101 | 547.7 | 546.18 |
| 48 | 0.798 | 94 | 532.1 | 532.13 |
| 49 | 2 | 75 | 518.1 | 518.15 |
| 50 | 0.248 | 96 | 518.7 | 519.14 |
| 51 | 0.047 | 100 | 504.8 | 505.13 |
| 52 | 6.52 | 58 | 505.8 | 506.15 |
| 53 | 0.014 | 99 | 520.1 | 520.16 |
| 54 | 0.014 | 98 | 534.1 | 534.18 |
| 55 | 6.73 | 58 | 517.7 | 518.15 |
| 56 | 0.061 | 98 | 511.8 | 512.22 |
| 57 | 8.21 | 51 | 527.7 | 528.11 |
| 58 | 0.007, 0.016 | 102, 99 | 534.2 | 534.18 |
| 59 | 0.05 | 99 | 519.7 | 520.16 |
| 60 | 0.054 | 100 | 517.7 | 518.15 |
| 61 | 0.045 | 102 | 548.2 | 548.19 |
| 62 | 0.059 | 98 | 574.2 | 574.21 |
| 63 | 0.12 | 101 | 582.1 | 582.18 |
| 64 | 0.072 | 100 | 576.1 | 576.19 |
| 65 | 0.485 | 88 | 596.1 | 596.19 |
| 66 | 0.023 | 99 | 572.1 | 572.16 |
| 67 | 0.018 | 99 | 550.1 | 550.17 |
| 68 | 1.21 | 84 | 505.8 | 506.15 |
| 69 | 6.51 | 60 | 455.9 | 456.17 |
| 70 | 0.009 | 101 | 532.2 | 532.16 |
| 71 | 0.012 | 100 | 568.2 | 568.16 |
| 72 | 0.064 | 100 | 598.1 | 598.17 |
| 73 | 0.039 | 100 | 602.1 | 602.12 |
| 74 | 0.138 | 100 | 636.1 | 636.15 |
| 75 | 0.036 | 101 | 569.2 | 569.16 |
| 76 | 0.23 | 93 | 610.1 | 610.17 |
| 77 | 0.789 | 81 | 413.9 | 414.19 |
| 78 | 0.3 | 89 | 429.8 | 430.17 |
| 79 | 0.071 | 101 | 467.9 | 468.24 |
| 80 | 0.071 | 100 | 489.7 | 490.20 |
| 81 | 0.452 | 84 | 422.9 | 423.21 |
| 82 | 0.498 | 84 | 493.8 | 494.25 |
| 83 | 0.988 | 80 | 497.7 | 498.20 |
| 84 | 0.042 | 99 | 452.9 | 453.23 |
| 85 | 0.051 | 96 | 455.2 | 455.22 |
| 86 | 3.26 | 61 | 459.9 | 460.27 |
| 87 | >10 | 38 | 456.9 | 457.17 |
| 88 | 4.74 | 59 | 555.2 | 555.28 |
| 89 | 9.07 | 46 | 569.3 | 569.30 |
| 90 | 0.031, 0.043 | 100, 100 | 543.2 | 543.23 |
| 91 | 0.054 | 101 | 563.2 | 563.22 |
| 92 | 0.04 | 97 | 562.2 | 562.22 |

TABLE 2-continued

| Cpd | Ca$^{2+}$ Mobilization IC$_{50}$ (µM) | Ca$^{2+}$ Mobilization % Inh @10 µM | MS obs | MS calc |
|---|---|---|---|---|
| 93 | 0.227 | 92 | 457.2 | 457.21 |
| 94 | 4.8 | 60 | 468.7 | 469.19 |
| 95 | 0.084 | 96 | 468.7 | 469.19 |
| 96 | >10 | 43 | 438.9 | 439.22 |
| 97 | 0.318 | 86 | 448.8 | 449.21 |
| 98 | >10 | 34 | 448.8 | 449.21 |
| 99 | 0.794 | 73 | 481.8 | 482.22 |
| 100 | 8.82 | 48 | 481.8 | 482.22 |
| 101 | >10 | 33 | 468.9 | 468.20 |
| 102 | 3.49 | 68 | 519.7 | 520.16 |
| 103 | 0.023 | 99 | 596.1 | 596.14 |
| 104 | 0.011, 0.011 | 99, 102 | 519.2 | 519.23 |
| 105 | 0.089 | 100 | 547.2 | 547.26 |
| 106 | 0.508 | 89 | 590.3 | 590.25 |
| 107 | 0.012 | 101 | 554.2 | 554.21 |
| 108 | 0.369 | 89 | 582.3 | 582.36 |
| 109 | 0.129 | 99 | 495.9 | 496.27 |
| 110 | 1.16 | 81 | 440.9 | 440.20 |
| 111 | 0.154 | 100 | 464.7 | 465.12 |
| 112 | 0.026 | 101 | 463.8 | 464.20 |
| 113 | 0.024, 0.046, 0.076 | 101, 100, 102 | 505.8 | 506.15 |
| 114 | 0.041 | 99 | 524.2 | 524.20 |
| 115 | 0.047 | 99 | 514.2 | 514.26 |
| 116 | 0.057 | 99 | 510.2 | 510.26 |
| 117 | 0.084 | 79 | 532.2 | 532.25 |
| 118 | 0.006, 0.006 | 98, 102 | 536.2 | 536.22 |
| 119 | 0.006, 0.012 | 102, 99 | 536.2 | 536.22 |
| 120 | 0.009, 0.015 | 100, 102 | 532.2 | 532.25 |
| 121 | 0.020, 0.033 | 101, 98 | 498.2 | 498.26 |
| 122 | 1.08 | 78 | 443.1 | 443.17 |
| 123 | >10 | 34 | 404.0 | 404.24 |
| 124 | 1.56 | 74 | 416.0 | 416.24 |
| 125 | 0.487 | 83 | 438.9 | 439.22 |
| 126 | 0.115 | 95 | 576.3 | 576.31 |
| 127 | 0.058 | 100 | 602.1 | 602.21 |
| 128 | 0.04 | 100 | 534.2 | 534.23 |
| 129 | 4.78 | 64 | 427.8 | 428.16 |
| 130 | 1.87 | 71 | 417.9 | 418.14 |
| 131 | >10 | 32 | 496.3 | 495.9 |
| 132 | 8.5 | 54 | 556.2 | 556.2 |
| 133 | 0.2 | 93 | 564.2 | 564.22 |
| 134 | 0.019, 0.028 | 97, 97 | 546.2 | 546.23 |
| 135 | 0.013, 0.024 | 100, 94 | 520.2 | 520.22 |
| 136 | >10 | 50 | 470.2 | 470.23 |
| 137 | 0.031 | 98 | 470.2 | 470.23 |
| 138 | 1.34 | 70 | 642.2 | 642.26 |
| 139 | 0.018 | 95 | 533.2 | 533.24 |
| 140 | 0.455 | 89 | 512.2 | 512.24 |
| 141 | 1.84. | 73 | 417.9 | 417.85 |
| 142 | 0.323 | 90 | 500.1 | 500.22 |
| 143 | 0.027 | 101 | 440.1 | 440.20 |
| 144 | 1.33 | 77 | 514.2 | 514.23 |
| 145 | 0.461 | 86 | 467.9 | 468.24 |
| 146 | 0.67 | 87 | 482.0 | 482.25 |
| 147 | 808 | 82 | 520.3 | 520.1 |

*Values are representative of a range of values determined upon multiple testing.

Biological Examples 3A-3E

Effect of PK1 on Secretion and Gut Mucosal Ion Transport in Mammals

Biological Example 3A

Effect of PK1 on Secretion and Gut Mucosal Ion Transport in Mammals

Methodology. Full thickness segments of ileum starting at a point 2 cm proximal to the ileocecal junction and extending 10 cm proximally were freshly excised, placed into Krebs-Ringer bicarbonate (KRB) solution, and emptied of their contents as a plastic rod was gently inserted into the intact segment. Ileal segments were scored with the back-edge of a scalpel blade along the entire mesenteric border, and the intact muscular layers including the myenteric plexus were carefully removed with flat-head forceps. Three rectangular tissue sheets approximately 1.5 cm in length were prepared from the remaining muscle-stripped, mucosa-submucosa tissues and cut with care taken to avoid Peyer's patches. Each tissue sheet containing intact submucosal ganglia was pinned over a rectangular portal (total cross-sectional area of exposed mucosa=0.50 cm$^2$) between halves of an acrylic mounting cassette that was inserted between the tissue-bathing reservoirs of a modified Using-type flux chamber (Physiologic Instruments, Inc., San Diego, Calif.). For a discussion on transepithelial measurements using a Using chamber, see Martin J. Hug, Transepithelial Measurements Using the Using Chamber, The European Working Group on CFTR Expression (2002).

The apical (i.e., mucosal) and basolateral (i.e., serosal) surface of each tissue was bathed with 6 ml of an oxygenated KRB solution maintained at 36° C. Once mounted, tissues were allowed to equilibrate for 0.5-1 h before electrical field stimulation and addition of secretagogues or drugs. The KRB solution contained (in mM) 120 NaCl, 6 KCl, 1.2 MgCl$_2$, 1.2 NaH$_2$PO$_4$, 14.4 NaHCO$_3$, 2.5 CaCl$_2$, and 11.5 glucose or 11.5 mannitol. The KRB solution was continuously aerated with 95% O$_2$: 5% CO$_2$ and maintained at pH 7.3. Each chamber was equipped with a pair of saturated KCl-agar bridges for measurement of transmural electrical potential difference (PD) across the tissue, and a pair of Ag—AgCl agar electrodes connected to an automated voltage-clamp device (model VCC MC6, or model VCC MC8, Physiologic Instruments, Inc., San Diego, Calif.) that compensated for solution resistance between the PD-sensing bridges and for deviations detected from a transmural potential difference (PD) across the tissues that were clamped at 0 mV. Tissue conductance (G) was calculated (in mS) by determining the current necessary to change PD by 1 mV using bipolar pulses from a pulse generator. Short-circuit current (Isc in mA), an index of net active ion transport, was measured continuously. Tissue conductance (Gt in mS), an index of the barrier function to passive flow of ions, was calculated from changes in Isc and the transepithelial potential difference for each tissue.

Baseline recordings of short-circuit current (Isc) and G for each tissue were acquired and recorded for an additional 15 min period prior to the start of an experimental protocol. Stimulated changes in Isc were measured and recorded continuously with a computerized data acquisition system (PowerLab 8SP, ADInstruments, Inc., Colorado Springs, Colo.). Neurally-evoked changes in Isc were obtained by application of electrical field stimulation (80V, 0.5 ms, 10 Hz, 5 s) from the outputs of an electronic stimulator (S-48, Grass-Telefactor, Astro-Med, Inc., West Warwick, R.I.) attached via aluminum foil electrodes placed in direct contact with the mucosal surface at opposite poles of each tissue. Pharmacological agents and secretagogues were routinely added to the basolateral-side reservoir. Agonist or secretagogue effects on Isc were continuously recorded following basolateral addition. Concentration-response curves were constructed from the cumulative, step-wise addition of pre-determined increasing amounts of agonist or secretagogue that were added at or near the peak Isc response to the preceding lower concentration. Effects of antagonists or inhibitors of secretion were evaluated after a 10-20 minute exposure period that was followed by challenge with a specific agonist or secretagogue.

Statistical Analysis. All values are reported as means +/− SE. Electrophysiological data obtained with Using flux-type chambers were normalized to tissue surface area and expressed per cm². Stimulated changes in ion transport were determined as the absolute difference between a baseline value prior to stimulation and the maximal response (ΔIsc) evoked by a given stimulus or secretagogue. An estimated $EC_{50}$ for the stimulatory action of PK1 on epithelial secretion was determined from a 7-point cumulative concentration-response test using a computer calculated curve-fitting function in PRISM (GraphPad Software, Inc). An unpaired, two-tailed Student's t-test was used to determine statistical significance between any two groups, e.g., control and experimental tissues. An ANOVA in conjunction with a post hoc Neuman-Keuls multiple comparisons test was used to determine significant differences among multiple groups. $P<0.05$ was considered statistically significant.

Figure 1:
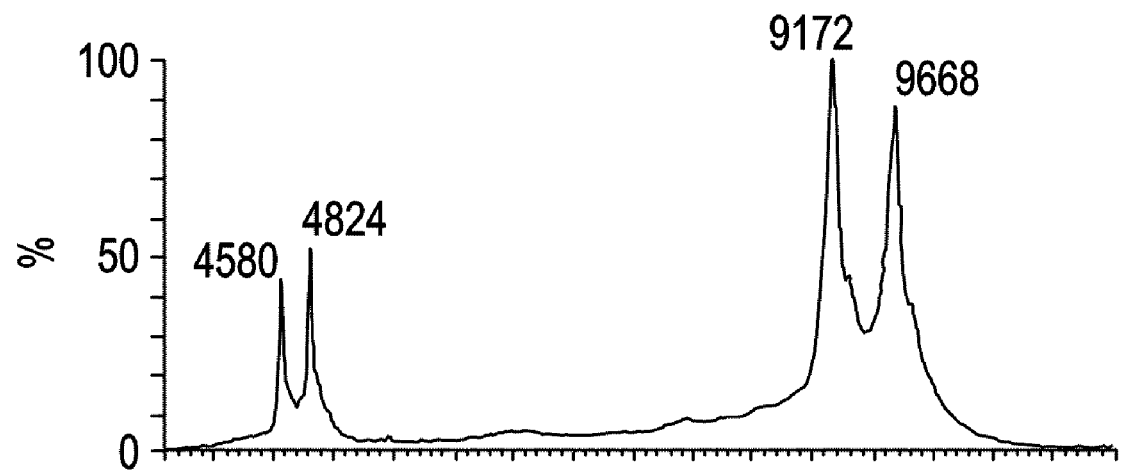
FIG. 1 shows a MALDI-TOF ANALYSIS of a PK1 ligand preparation mixture. The mixture includes a four C-terminal residue truncated product (MW=9172), and a full-length PK1 ligand (MW=9668).
Figure 2A:
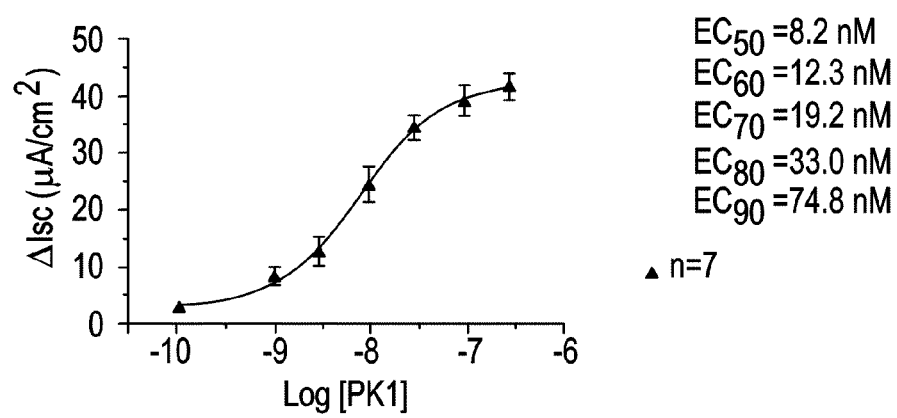
FIG. 2A shows a cumulative concentration-response curve evoked in the short-circuit current (Isc) response to PK1 peptide in PK1 exposed rat ileal tissues mounted in Using-type ion flux chambers.
Figure 2B:
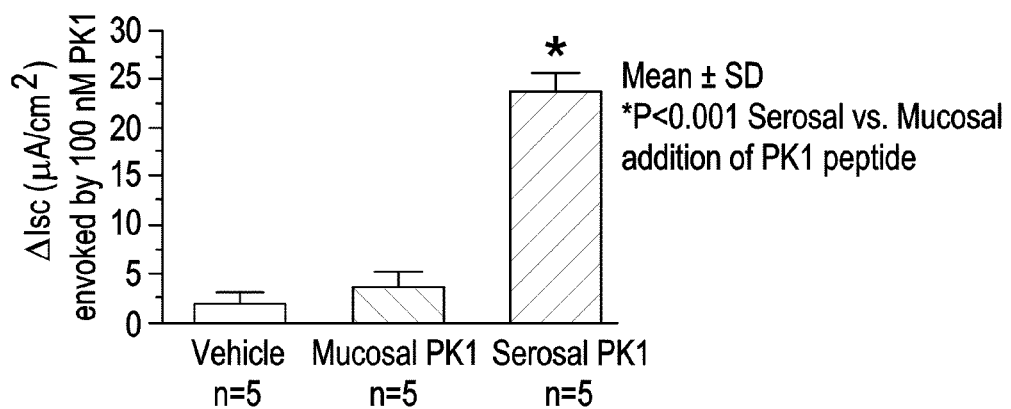
FIG. 2B is a graphical representation that shows that the Isc response (a correlate of secretion) evoked by PK1 in rat ileum mucosa is only obtained when the peptide is added to the serosal side of isolated epithelial tissues mounted in Using-type ion flux chambers. Addition of PK1 peptide to the mucosal tissue surface failed to evoke a change in Isc. (Data reported as means and standard deviations; one-way ANOVA and Neumann-Kuels Multiple Comparisons Test).
Figure 3:
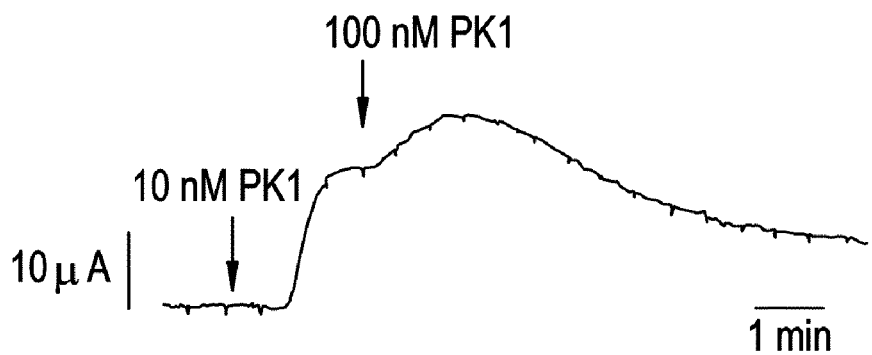
FIG. 3 shows a representative short-circuit current tracing obtained under voltage-clamp conditions from an isolated piece of rat ileum mucosa devoid of its muscular layers and mounted in an Using-type ion flux chamber to which final concentrations of 10 nM (~$EC_{50}$) and 100 nM (~maximal effect) PK1 peptide had been added in a cumulative fashion. This protocol was used throughout the investigation of the pro-secretory effects of PK1 peptide and for characterizing small molecule antagonist efficacy.
Figure 4:
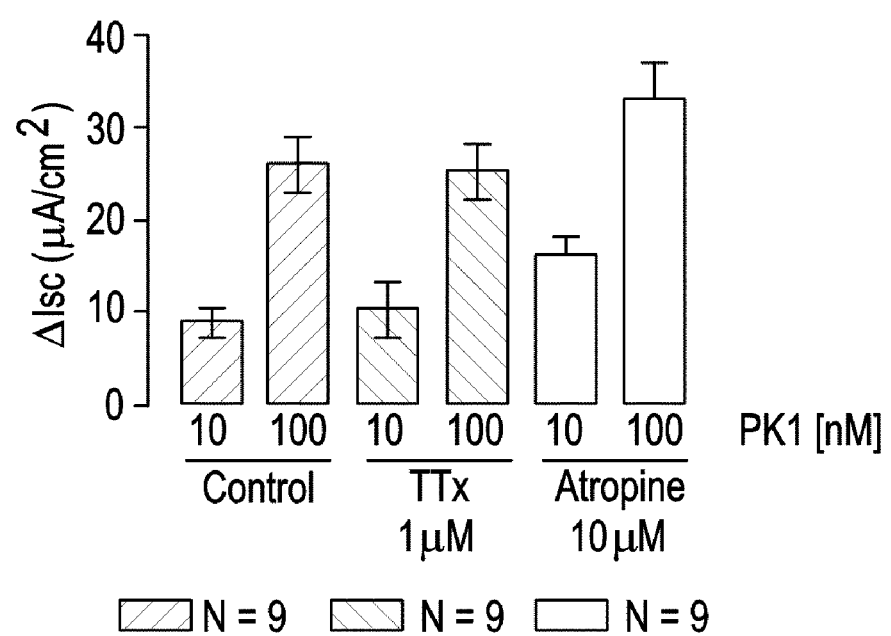
FIG. 4 is a graphical representation that shows that the Isc response evoked by PK1 in rat ileum mucosa is not dependent on either intrinsic neural activity or activation of cholinergic muscarinic receptors by release of the intrinsic neurotransmitter acetylcholine.

Summary of results. The change in Isc is reported as the difference between the peak Isc response to PK1 at a given concentration compared to the initial baseline (unstimulated) Isc value and expressed as Δ Isc measured in microAmps (μA) corrected for the surface area (in cm²) of the tissue mounted in the Using-type chamber. An $EC_{50}$ value for the response curve was calculated as described in Biological Example 3A. The basal Isc was 35.2+/−2.4 μA/cm² and tissue conductance (G) was 33.7+/−0.9 mS/cm² (n=79 tissues from 34 rats). Following a single-dose addition of PK1 to the Krebs solution bathing the basolateral tissue surface, Isc gradually increased to a peak value within 2-4 min and then declined back toward baseline within 10-15 min. The PK1-evoked increases in Isc were concentration dependent with an $EC_{50}$ of approximately 8.2 nM determined from cumulative concentration-response studies. The maximal response for the PK1-evoked response occurred at 100 nM; 100 nM PK1 evoked an increase in Isc of 28.7+/−2.9 μA/cm₂ from baseline (n=42 tissues from 29 rats) and 10 nM PK1 evoked an increase of 13.5+/−2. nA/cm²(n=33 tissues from 22 rats). The concentrations of 10 nM and 100 nM were used in all subsequent studies. PK1 had no significant effect on G in any of of the studies. FIG. 4 shows that the pro-secretory effect of PK1 was not blocked in the presence of the nerve conduction toxin, Tetrodotoxin (TTX), or blockade of muscarinic receptors present on mucosal enterocytes by the anti-cholinergic drug, Atropine. This indicates that its action is not dependent on intrinsic neural activity in the tissues.

Figure 5:
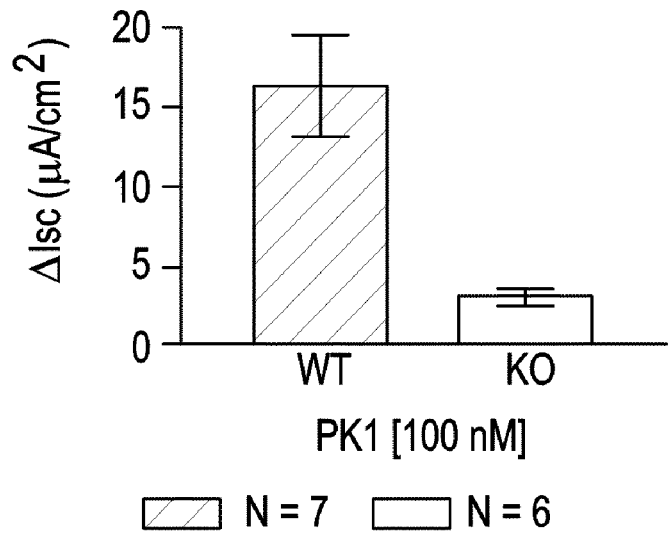
FIG. 5 is a graphical representation showing that exogenous PK1 peptide failed to evoke a significant change in Isc in epithelial tissues from PK1 receptor knock-out [KO] mice compared to wild-type [WT] littermates.

The PK1 evoked increase in Isc requires the presence of endogenous PK1 receptors since exogenous PK1 peptide added to ileum mucosal tissues from PK1 receptor knock-out mice did not elicit a significant change in Isc compared to wild-type littermates. (See FIG. 5).

Biological Example 3B

Mechanism of Action of PK1 Evoked Increase in Gut Secretion in Rat Ileum

Methodology. The basic methodology for Using-type ion flux chambers used in these studies was the same as that described in detail above with the following modifications to the experimental protocol. To determine the mechanism of action of the pro-secretory action of PK1 on the epithelium, three separate approaches were utilized to abolish electrogenic chloride ion or bicarbonate ion transport across the epithelium. The first approach involved the addition of Bumetanide (500 nM), an inhibitor of the basolateral $Na^+$—$K^+$-$2Cl^-$ co-transporter, to disrupt the net electrogenic flux of $Cl^-$ ions in a basolateral-to-apical direction that helps to drive fluid and electrolyte secretion in the gut. The second approach involved replacement of all chloride ions in the physiological buffer solution used to maintain living tissues in the Using chambers, thus substituting a chloride-free KRB solution by an equimolar substitution of isethionate and acetate salts for the chloride salts listed in the standard KRB recipe above. The third approach involved replacement of all bicarbonate ions in the physiological buffer solution, thus substituting a bicarbonate-free KRB solution by an equimolar substitution of Piperazine-N,N'-bis(2-ethanesulfonic acid) (PIPES) for the bicarbonate salt, and addition of 1 mM acetazolamide, a blocker of intracellular carbonic anhydrase, to prevent bicarbonate production by the enterocyte.

Figure 6:
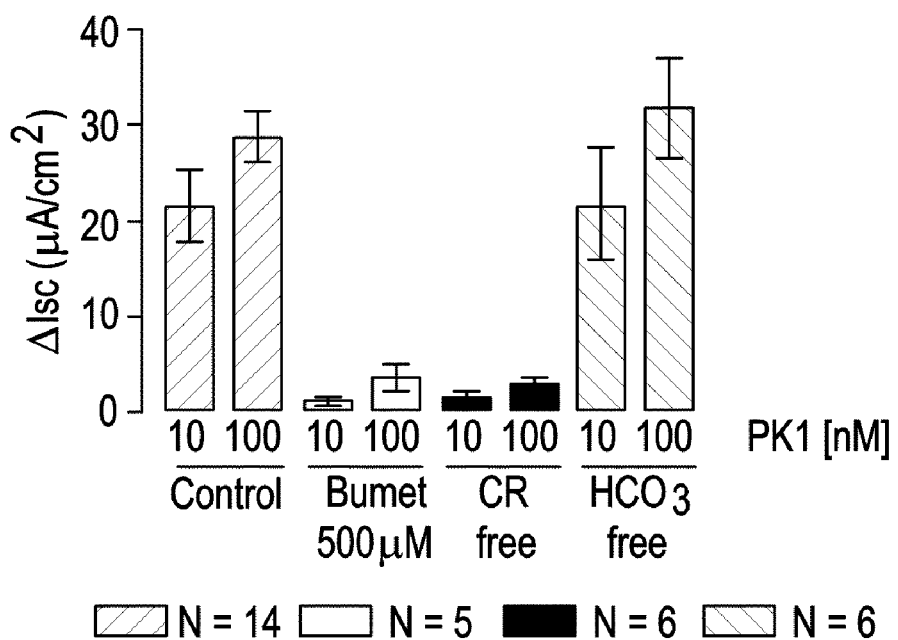
FIG. 6 is a graphical representation showing that the pro-secretory effect of PK1 in rat ileum mucosa is dependent exclusively upon stimulation of an electrogenic chloride ion transport mechanism in a net basolateral-to-apical direction across the epithelium.

Summary of results. The ionic basis for PK1-evoked increases in Isc was determined in experiments using bumetanide and Cl⁻-free Krebs solution to block the basolateral $Na^+$-$K^+$-$2Cl^-$ co-transporter. (See FIG. 6). The concentration of bumetanide (500 μM) was chosen based on its reported successful use in similar ion transport studies elsewhere. Following addition of bumetanide to the serosal bathing solution, baseline Isc appeared to decrease (−7.1+/−8.6 μA/cm², n=5); however, this was not significantly different compared to tissues receiving the DMSO vehicle alone (6.6+/−4.0 μA/cm², n=4). Additionally, bumetanide did not significantly change baseline G; however, bumetanide significantly attenuated the PK1-evoked increase in Isc by >90%. In Cl⁻-free Krebs solution, the response to serosal addition of PK1 was also diminished by >90%; however, bicarbonate-free KRB containing acetazolamide had no effect on the Isc response to PK1 suggesting that it does not effect bicarbonate transport.

Biological Example 3C

Figure 7:
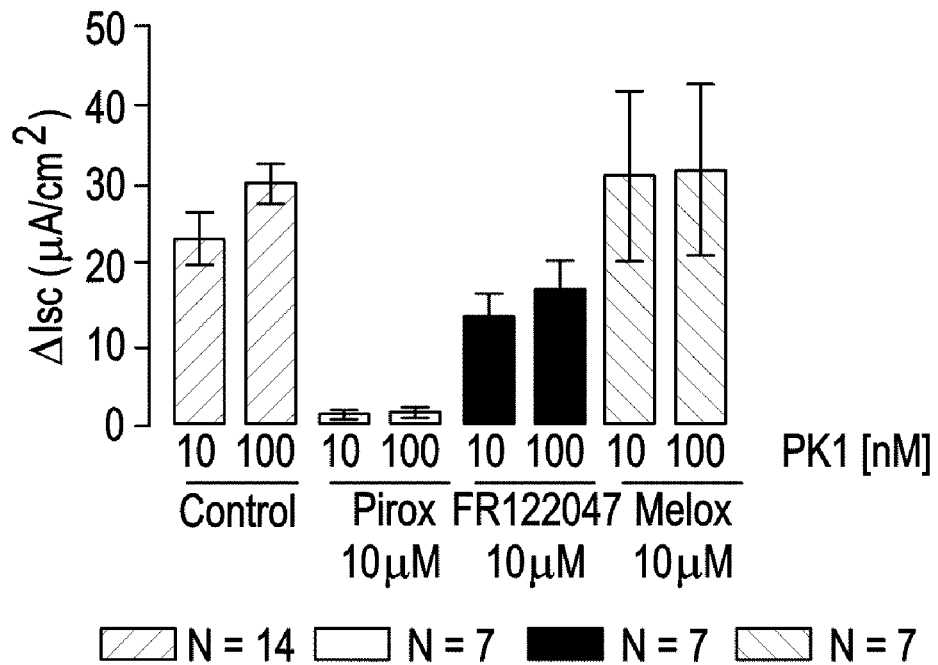
FIG. 7 is a graphical representation showing that the PK1 evoked increase in Isc in rat ileum mucosa is dependent, in part, on the production of endogenous prostaglandin by cyclo-oxygenase.
Figure 8:
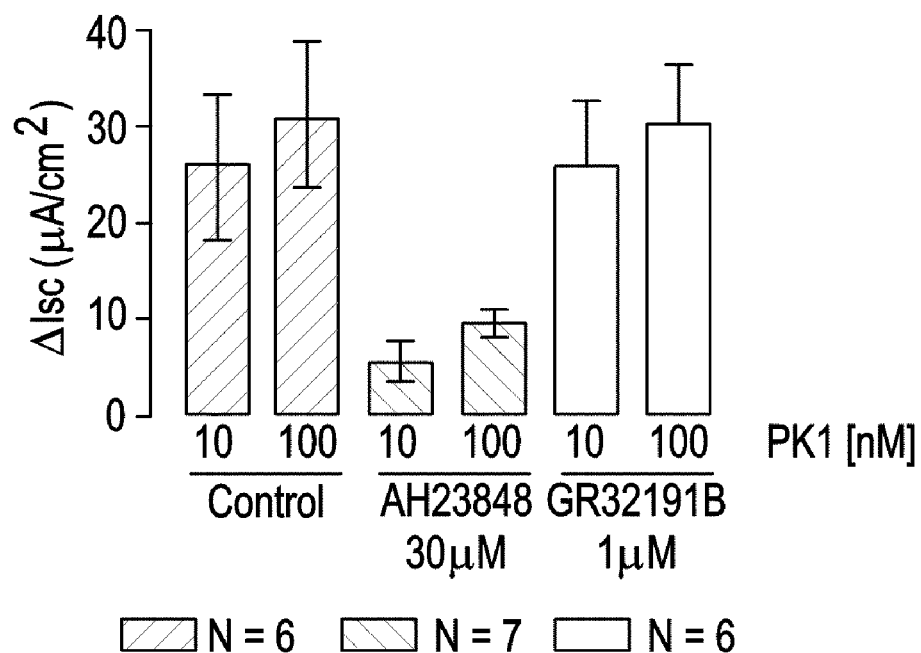
FIG. 8 is a graphical representation showing that the PK1 evoked increase in Isc in rat ileum mucosa is dependent, in part, on the production of endogenous prostaglandin that acts at prostaglandin EP4 receptors located in the epithelium.

PK1 Stimulated Gut Secretion in Rat Ileum is Partially Dependent on the Synthesis of Endogenous Prostanoids Acting at the Epithelial EP4 Receptor Methodology. The basic methodology for Using-type ion flux chambers used in these studies was the same as that described in detail above with the following modifications to the experimental protocol. Many different peptides and neuropeptides contained in the gut have been shown to exert their pro-secretory effect, in part, via stimulation of endogenous prostaglandin production. To elucidate the potential role for endogenous prostaglandin synthesis in the PK1 stimulated Isc response in rat ileum, experiments were carried out in which rat ileum mucosa was pre-treated with serosally added Piroxicam (10 μM) a non-selective cyclo-oxygenase (COX) inhibitor, FR122047 (10 mM) a selective COX-1 isoform inhibitor, and Meloxicam (10 μM) a selective COX-2 isoform inhibitor. (See FIG. 7). In a follow-on experiment to determine if endogenously produced prostaglandin acted at a specific receptor sub-type, tissues were pre-treated by serosal addition of selective antagonists for the prostaglandin receptor, EP4 (AH23848 at 30 μM), and the thromboxane receptor, TP (GR32191B at 1 μM), in order to determine the putative signaling mechanism involved in the PK1 driven prostaglandin-stimulated Isc response.

Summary of results. The results suggest that PK1 mediated secretion in the rat ileum is dependent, in part, on endogenous prostaglandin synthesis by COX. Based on experiments in which selective COX isoform inhibitors were used, the results indicate that the inducible COX-2 isoform is not involved in the PK1 stimulated production of prostaglandin. Results from the follow-on experiment suggest that the endogenous prostaglandins stimulated by PK1 exposure signal via activation of the prostaglandin EP4 receptor sub-type that has been shown to have a preferential localization to the rat gut epithelium.

Biological Example 3D

Figure 9A:
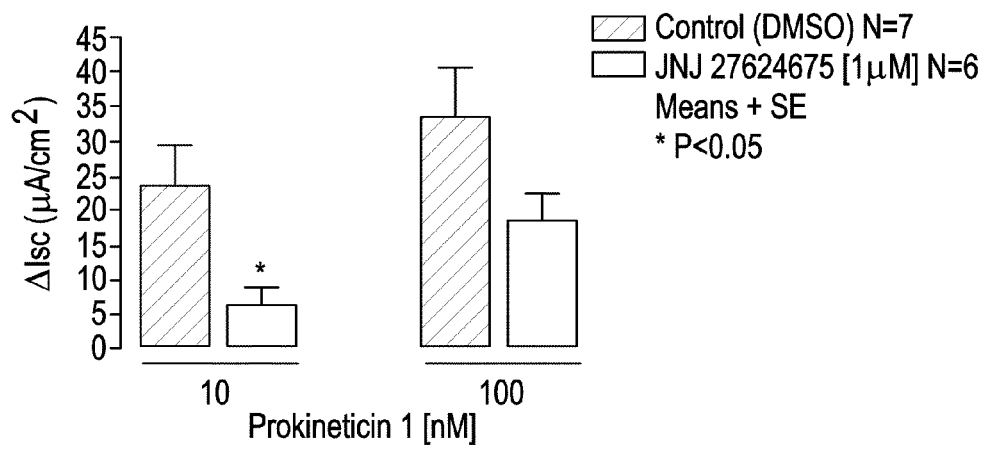
FIGS. 9A and 9B are graphical representations that demonstrate that the PK1 evoked increase in Isc was suppressed in the presence of the substituted aminoguanidines, JNJ 27624675 (see below) (FIG. 9A) and JNJ 28480894 (see below) (FIG. 9B), small molecule antagonists at the PK1 receptor.
Figure 9B:
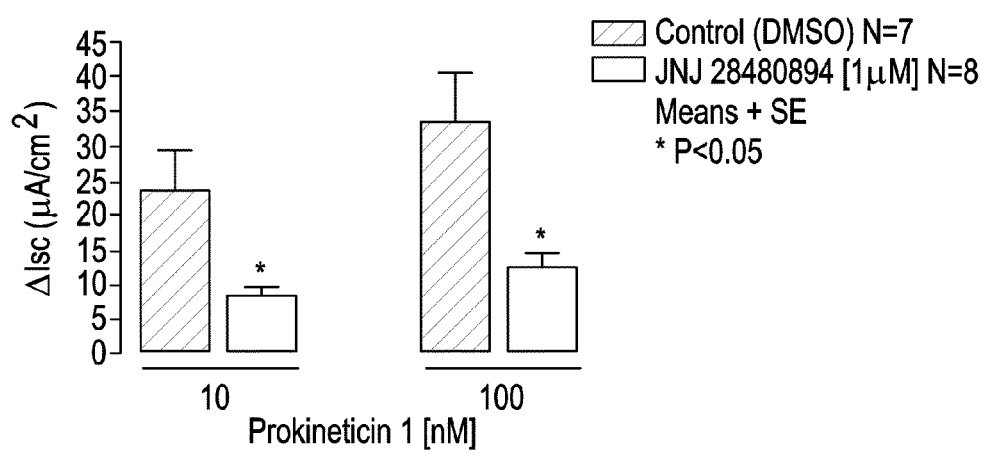

Small Molecule PK1 Receptor Antagonists Are Effective at Suppressing Both PK1 and Cholera Toxin Stimulated Gut Secretion in Rat Ileum Methodology. The basic methodology for Using-type ion flux chambers used in these studies was the same as that described in detail above with the following modifications to the experimental protocol. Following a 30-45 minute equilibration period, baseline-stable tissues were subjected to a train of electrical field stimulation (EFS; 80 V, 0.5 ms, 10 Hz, 5 s) applied from contacts connecting the foil electrodes on opposite poles of the tissue to the polarized, isolated outputs from an electronic square-pulse stimulator. The responses to two sequential EFS were used to guage tissue viability and comparability of the responses of individual tissues from each rat and between rats. Tissue conductance was measured at periodic intervals as changes in the amplitudes of brief short-circuit current responses evoked by application of 1 mV amplitude bi-polar pulses from a pulse generator using Ohm's Law. Three to four tissues from each rat were studied. The tissues from a given animal were grouped and assigned accordingly: one control tissue which received only vehicle followed by two consecutive doses of PK1 ligand added in a cumulative fashion to the basolateral surface of the tissue; the remaining two to three tissues from the same animal were assigned to be exposed to a given PK1 receptor antagonist (e.g., 3-4 tissues from 1 rat: Control, Antagonist$_1$, Antagonist$_2$, Antagonist$_3$). Test compound was added to the basolateral tissue side reservoir at a final concentration of 1 µM and allowed a 15 minute incubation period prior to challenge with the PK1 peptide. At the end of this 15 minute exposure period, PK1 ligand at 10 and 100 nM was added in a cumulative fashion to each tissue to characterize the inhibitory effect of the test compound. At the conclusion of the experiment, EFS was re-applied to guage tissue viability and stability of responsiveness. The results are shown in FIGS. 9-11.

Summary of results. Pre-treatment of tissues with PK1 antagonists alone had no measurable effect on baseline Isc and tissue conductance (G). The results shown in FIGS. 9-11 indicate that suppression of the PK1 evoked increase in Isc in isolated rat ileum mucosa was successfully achieved in the presence of two different series of small molecular scaffolds (i e , aminoguanidine and aminobenzimidazole (FIGS. 9A and 9B and FIG. 11, respectively) that have been identified in cellular assay as putative antagonists at the PK1 receptor. In trials with compounds from each of the two series, the observed suppression of the Isc response evoked by two ascending cumulative concentrations of PK1 showed characteristics of a significant surmountable antagonism. The aminoguanidine, JNJ 28611921, failed to suppress the Isc response to PK1; however, this compound has been shown to lack significant activity at the PK1 receptor. These data suggest that good efficacy can be achieved in the selective functional blockade of the PK1 receptor by small molecule inhibitors to modulate the pro-secretory effect of PK1 on the intestinal epithelium.

Biological Example 3E

PK1 Stimulates Enteropooling and Accumulation of Fluid in Rat Small Intestine In Vivo Methodology. Experiments were carried out to gravimetrically measure the in vivo pro-secretory effect of PK1 peptide in the rat small bowel. The effect of PK1 peptide on stimulation of enteropooling and accumulation of fluid in the gut of intact rats was evaluated using two different routes of administration. Non-fasted rats were randomly assigned to two experimental groups (n=10 per group) in two separate experiments. In the first experiment, each rat was given an oral bolus (1.5 ml) of 6% carmine dye in 0.5% methylcellulose wt/vol containing a dose of PK1 peptide at 100 µg/kg or buffer vehicle. (See FIG. 12). In the second experiment, rats were injected intraperitoneally (i.p). with either PK1 peptide (100 ng/kg) or buffer vehicle followed immediately by intragastric administration of a 6% carmine dye in 0.5% methylcellulose test meal (1.5 ml). (See FIG. 13). Thirty minutes later, rats were rapidly euthanized by cervical dislocation after inhalation anesthesia with 100% carbon dioxide and the entire small intestine was excised from the pylorus to the ileocecal junction. The total small bowel length was measured and then divided equally into thirds using 4-0 silk suture loops to ligate, isolate, and separate each segment to prevent leakage of intraluminal contents. Each segment (proximal, mid, and distal) was weighed intact to the nearest milligram, carefully cut open longitudinally, gently blotted with an absorbant paper sheet, emptied of its fluid contents and then re-weighed. Care was taken not to re-distribute or remove any solid or semi-solid intraluminal contents. Net fluid content weight was calculated as the difference between intact and empty intestinal segment weights to the nearest milligram and normalized to segment wet tissue weight in grams.

Summary of results. The results demonstrate that PK1 peptide stimulates enteropooling and accumulation of fluid in the rat small intestine in vivo. In general, this effect appears to involve all three regions of the small bowel; however, the effect is most significant in the more distal (i.e., mid and distal segments) regions. These data are consistent with the evidence indicative of a pro-secretory action of PK1 peptide obtained with isolated preparations of rat ileum mucosa mounted in Using-type ion flux chambers and studied ex vivo.

Biological Examples 4A-4C

Actions of PK1 on Gastrointestinal Smooth Muscle

Biological Example 4A

PK1 Stimulates Transit of an Oral Test Meal in the Rat Small Intestine In vivo

Methodology. Small intestinal transit. Rats received a bolus of 1.5 ml total volume that contained a 6% solution of carmine dye in 0.5% methyl cellulose (wt/vol) together with a dose of either PK1 (100 µg/kg) or vehicle by oral feeding tube. After 30 min, the rats were rapidly euthanized by cervical dislocation after inhalation anesthesia with 100% carbon dioxide. The entire small intestine of each rat was carefully resected starting at the ileal-cecal junction first and working back toward the pylorus of the stomach until the entire small intestine had been removed intact. The excised small bowel was arranged lengthwise along a metric straight-edge, and the length of the entire small intestine was measured in centimeters. The leading edge of the carmine dye front was visualized and the distance traveled by the carmine was also measured and calculated as a percentage of the total excised length of the small intestine. Transit was expressed as the percentage of the total intestinal length traveled by the carmine dye in 30 minutes. The results are shown in FIG. 14.

Summary of results. The results indicate that rats orally treated with PK1 had significantly accelerated small intestinal transit of a carmine test meal compared to vehicle treated counterparts. Thus, PK1 appears to have a stimulatory effect on propulsive motility in the upper gastrointestinal tract of treated rats.

Biological Example 4B

PK1 Stimulates Contractility of Isolated Rat Small Intestine Ex Vivo

The effects of PK1 on isolated segments of rodent gastrointestinal (GI) tissues have been studied ex vivo, using a "myobath" apparatus. This organ bath apparatus is used to measure the changes in contractile activity of GI smooth muscle following application of PK1, in the presence or absence of compounds that block PK1 receptor (PK1R)-mediated increases in intracellular free $Ca^{2+}$ in PK1R-transfected cells in vitro.

Methods. Rodents (mice, rats, and guinea pigs) were euthanized by CO asphyxiation, and exsanguinated. Segments of GI tissues, including stomach, duodenum, jejunum, ileum, proximal colon and distal colon were resected from the animals and mounted, either as intact segments (i.e., 15 mm long cylinders of intestine) or flat strips (~2.5 mm×15 mm) oriented along the longitudinal muscle axis. In some experiments flat strips were oriented along the circular muscle axis. Two types of longitudinally oriented flat strip preparations have been used: a) those that are comprised of the entire gut wall, and b) those that have been dissected to remove the mucosal and submucosal layers and are comprised only of muscularis externa (including myenteric plexus and serosa).

Each tissue preparation was mounted on a holder, equipped with a solid state strain gauge force transducers —to which one end of the preparation was connected- and immersed in Krebs-Ringers buffer (KRB, an isotonic, bicarbonate buffered, salt solution, pH 7.4) maintained at 35° C., and aerated with a mixture of 95% $O_2$/5% $CO_2$. The tissues were lengthened to impart a resting load of between 0.5-1.0 μm (depending on the preparation), and equilibrated under these conditions for 1 hr, changing the bathing solution to fresh KRB every 15 min. At the beginning of each experiment acetylcholine (ACh, 1 μM) was added to each bath in order to obtain a contractile response; following washout of ACh, PK1 was added to the bath either alone, or following the addition of a PK1R antagonist. The response to PK1 under these conditions is compared to the response of the same tissue preparation to ACh and the contraction (or relaxation) calculated as a percent of the response to ACh.

The actions of PK1 on guinea pig GI smooth muscle have previously been reported (Schweitz, Pacaud et al. 1999; Lai, Liu et al. 2003). Because PK1, and receptors that can be activated by it (PK1R and PK2R) are differentially expressed throughout the rat GI tract, the effects of the peptide on isolated segments of rat intestine and colon were characterized. PK1 (100 nM) evoked longitudinal contractions from intestinal tissues (mid-duodenum, jejunum, and distal ileum), whereas the same concentration of PK1 evoked longitudinal relaxations in proximal and distal colon. (See FIG. 6).

The results suggested that maximal contractile responses to PK1 are obtained from ileal tissues; therefore further experiments were carried out using ileal segments. The first studies utilized intact segments, and a later series of experiments were based on preparations consisting of the isolated ileal muscularis externa.

PK-1 Evokes Biphasic Contractions in Intact Ileal Preparations

Application of PK1 to isolated rat ileum evokes a biphasic response consisting of an early transient contraction and a late tonic contraction. (See FIG. 15). Application of the protein occurred at the arrow and remained in contact with the preparation for the duration of the recording.

The time to peak contraction of the early and late phases was determined to be 6.4 min and 53.8 min, respectively. Both the early and the late phases of the contractile response were determined to be concentration-dependent. (See FIGS. 17A and 17B). The $EC_{50}$ for the early and late contractile responses were determined to be 87.8 and 72.4 nM, respectively.

To determine whether the pronounced contractions in ileal smooth muscle are mediated directly by receptors on intestinal smooth muscle, tetrodotoxin (TTX, 0.1 μM) and atropine (1 μM) were added to the organ bath. The efficacy of TTX to block contractions mediated by the enteric nervous system (ENS) was verified by the complete inhibition of electrical field stimulus (EFS)—evoked contractions after its addition. The efficacy of atropine to block contractions mediated by muscarinic receptors located directly on ileal smooth muscle was tested by application of acetylcholine after addition of both TTX and atropine.

TTX and atropine attenuate the early, but not the late component of the PK1-evoked contractile response. These results suggest that the slowly developing, sustained contractile effects of PK1 on the ileal longitudinal muscle are neither neurally mediated, nor cholinergic. Other in vivo results (see above) have demonstrated a robust secretory effect of PK1 on rat ileum, therefore the idea that stimulation of mucosal receptors releases one or more substances that act to contract intestinal smooth muscle was tested by determining the actions of PK1 applied to mucosa-free ileal preparations. Removal of the ileal mucosa inhibits the slowly developing, "late" contractile response evoked by PK1. (See FIG. 18).

The Stimulatory Effect of PK1 is Attenuated by Small Molecule Antagonists

The ability of small molecule antagonists of the PK1R to inhibit the PK1-mediated contraction of GI smooth muscle was tested in this system. An example of the result is illustrated in FIG. 19, where JNJ-28845557 was observed to have a concentration-dependent inhibitory effect on the PK1-induced contraction of rat ileal longitudinal smooth muscle. Both the early and the late components of the responses were antagonized; however, the compound was more potent and more effective at inhibition of the early response compared to its effect on the late response.

Biological Example 4C

Immunocytochemical Localization of PK1 and PK1 Receptor in Tissues of Rodent Gastrointestinal Tract Administration of PK1 to rats has been demonstrated to stimulate secretion of fluid into the intestinal lumen and to increase the rate of transit of a marker down the gastrointestinal (GI) tract; furthermore, application of PK1 to isolated segments of rodent (rat, mouse and guinea pig) intestine has been shown to stimulate secretion of $Cl^-$ ions from GI epithelium, and to cause regionally specific contraction or relaxation of GI smooth muscle. These actions of exogenous PK1 are inhibited by small molecular weight antagonists of the PK1 receptor (PK1R). A series of immunocytochemical experiments were carried out in order to determine the distribution of the PK1 peptide in the GI tract and the site(s) of its actions at PK1R.

Methods. Antibodies to the human PK1 peptide amino acid sequence, SEQ ID NO 4: CSMDLKNINF, and to an amino acid sequence of the rat PKR1, SEQ ID NO 5: DFFSARDGS-GAETSP, were raised in rabbits. Rodents were euthanized by asphyxiation with $CO_2$ and the following tissues harvested: proximal stomach, distal stomach, duodenum, jejunum, ileum, proximal colon and distal colon. Tissues were rinsed in phosphate buffered saline (PBS) and fixed by immersion in 4% paraformaldehyde (w/v) in 0.1M phosphate buffer (pH 7.4 at RT) for 1-4 hrs. Two types of experiments were performed: in the first series of experiments, intact segments of gut were cryoprotected following fixation by overnight immersion in 30% sucrose (w/v) in PBS at 4° C., then embedded in OCT (Tissue Tek) and stored at −20° C. Sections (10-12 nm) of OCT-embedded tissues were cut on a cryostat microtome and thaw mounted onto microscope slides (VWR "Plus"-coated). OCT was removed from the sections by rinsing the slides in PBS and non-specific binding blocked by incubating the sections in 4% non-immune goat serum (v/v) in PBS containing 1% bovine serum albumen (fraction IV, w/v) and 0.4% Triton X-100 (v/v). Primary antibodies were applied overnight (RT), removed by rinsing in PBS, and then secondary antibodies, to which a fluorescent molecule (AlexaFluor 488, Molecular Probes, Eugene Oreg.) was conjugated, were applied for 4 hrs (RT). In the second series of experiments, segments of intestine and colon were opened longitudinally along the mesenteric border, and the gut pinned as a flat sheet, with the mucosa facing up, to the bottom of a dish lined with a silastic elastomer (Sylgard, Dow Corning, Midland Mich.), then fixed (as above). Following fixation, the flat segments of gut were dissected to yield laminar, whole mount preparations consisting of longitudinal muscle with adherent myenteric plexus (LMMP) or submucosa, containing the submucosal plexus (SMP). The whole mount preparations were immunostained (as above) before mounting them onto glass microscope slides. Coverslips were mounted onto the sections and whole mount preparations using a glycerol-based, anti-fading mounting medium (VectaShield, Vector Laboratories, Burlingame, Calif.) and the tissues examined using an epifluorescence microscope. The results are shown in FIGS. 20 and 21.

Results. PK1—immunoreactivity (IR) was detected in the mucosa of GI tissues. The PK1-IR was especially prominent in the gastric mucosa (FIG. 20). PKR1-IR was observed in neurons of both submucosal (FIG. 21A) and myenteric (FIG. 21B) ganglia. The immunoreactivity seems to be specific since omission of the primary antibody results in near total loss of fluorescence. (See FIGS. 21B and 21C). These data suggest that the gut is a source of PK1 and that receptors for the peptide are localized to enteric neurons. Thus, the pro-secretory and pro-motility effects of PK1 may be mediated in part via enteric neuronal pathways.

Expression of PK1 and PK1 Receptor in Murine DSS-induced Colitis

The mRNA for the PK1 receptor is not increased in the distal colon at day 7 of DSS-induced colitis in the mouse. (See FIG. 22).

Murine Mustard Oil-induced Colitis

The mRNA for PK1R has a small, but statistically significant increase in the distal colon at 2 hours after a single intracolonic administration of mustard oil. (See FIG. 23). Levels return to that of control by 6 hours. This suggests that there may be a role for PK1R in the rapid response of the colon to mustard oil.

There is a large, statistically significant increase in the mRNA for PK1 in the distal colon of mice at 6 hour following intracolonic administration of mustard oil. Levels return to that of control by 24 hours, suggesting that PK1 may play a role in the rapid response of the colon to mustard oil. (See FIG. 24).

Normal Rat GI Tissue

The highest levels of PK1R mRNA are in the ileum (both muscle and mucosa), lowest levels in the duodenum and stomach, with intermediate levels in the distal colon (lane labeled saline), jejunum, and liver. (See FIG. 25). PK1R mRNA levels do not change in the distal colon (lane labeled TNBS) at 3 days after TNBS induction in the distal colon. Similarly, PK1R mRNA levels do not change in the distal colon when mounted in an Using chamber and treated with vehicle (lane labeled UC control) or cholera toxin (UC cholera toxin). Highest levels of PK1 mRNA are observed in the stomach, lowest levels are observed in the duodenum, jejunum, and liver, and intermediate levels are observed in the ileum (both muscle and mucosa) and colon. These data indicate that the GI tract produces both PK1R and PK1, with regional differences steady state levels of mRNA. The high levels of PK1 in the stomach suggest that the stomach may produce the bulk of PK1 which would then be available to the rest of the GI tract. The presence mRNA's for both the ligand and receptor in the ileum suggest the possibility that local paracrine interactions may occur.

PK1R Knockout Mouse

The PK1R knockout mouse (−/−) does not express PK1R mRNA in the ileum, whereas the wild type mouse (+/+) does express PK1R mRNA. (See FIG. 26). There is a small, but statistically significant decrease in PK1 mRNA in the ileum of KO mice. (See FIG. 27). These data confirm the fidelity of the genetic KO of PK1R and suggest that loss of PK1R may slightly decrease the steady state levels of PK1 in the ileum.
RNA ISOLATION (Qiagen Rneasy 96 Plate)

RNA was aquired from vendors and tissues aquired from in house animal models. Tissue samples were stored at −80° C. or 4° C. in RNA Later (Qiagen, Valencia Calif.) until they could be processed. The RNA Later was removed and replaced with qiazol (Qiagen), as well as a stainless steel tissue grinding beads (4.0 mm con ballbearings —Montreal Biotech, Montreal Que). The samples were run through a Retsch MM 300 homogenizer (Qiagen). Following chloroform addition and centrifugation the aqueous phase was collected and mixed with 70% ethanol and poured into filtered columns of the Qiagen Rneasy 96 Plate. Following manufacturer's instructions the sample was finally eluted in RNase free water. The RNA preparation was then treated for DNase following the manufacturer's instructions of the Dnase Free Dnase Treatment Kit (Ambion, Austin Tex.). RNA quantity was assessed by ultraviolet spectrophotometry. RNA integrity was assessed by the 2100 Bioanalyzer Instrument (Agilent Technologies, Palo Alto Calif.) running the samples through the Total Nano RNA Eukaryotes procedure.
LiCl Precipitation For DSS-treated samples, the following procedure was used. This procedure was modified from Cathala et al. (1983). The RNA preparation was mixed with a stock solution of RNase free lithium chloride (LiCl, Ambion) dissolved in RNase free water, in order to obtain a final concentration of 2.5 M LiCl. This mixture was incubated at —20° C. for 30 min, afterwards it was brought out to room temperature. When the sample had just thawed it was centrifuged at 4° C. for 15 min at 18 000 rcf. The fluid was aspirated away and the pellet was washed with 1 ml ice-cold 70% ethanol. The sample was once again spun for 15 min at 4° C. at 18 000 rcf. The sample was washed and spun once more and then allowed to air dry for approximately 15 minutes. The pellet was resuspended in RNase free water. Optical density readings were then taken to calculate RNA quantity, each sample was read in triplicate.

TaqMan Real Time RT-PCR

A 1:1 (v/v) addition of the High Capacity cDNA Archive Kit (Applied Biosystems, Foster City Calif.) was added to each RNA sample first diluted to 250 ng/ul. This mixture was incubated at 37° C. for 2 hours. The sample was then diluted by a factor of 15.625×, so that 8 ng/ul of cDNA was available to load 5 μl per well into 384 well optical read plates. The primer/probe was made up with 2× RT-PCR Master Mix (Applied Biosystems) and 7 ul of this solution was added to each well, the plate was then run in a 7900 Fast Real Time PCR System (Applied Biosystems). Taqman primer/probes were purchased from the commercially available stock developed by Applied Biosystems. Samples were run in triplicate for each probe tested.

While the foregoing specification teaches the principles of the present invention, with examples provided for the purpose of illustration, it will be understood that the practice of the invention encompasses all of the usual variations, adaptations and/or modifications as would be understood by one of ordinary skill in the art.

The invention claimed is:

1. A method of treating inflammation in the intestine of a mammal in need thereof, comprising administering to the mammal a PK1 antagonist selected from

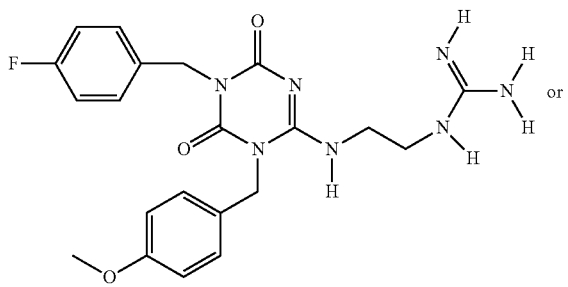

or

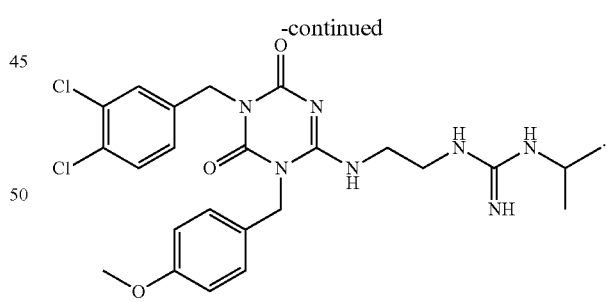

2. The method according to claim 1, wherein the inflammation is chronic.

3. The method according to claim 1, wherein the inflammation is sporadic.

4. The method according to claim 1, wherein the inflammation is a symptom of irritable bowel syndrome.

5. The method according to claim 1, wherein the inflammation is a symptom of inflammatory bowel disease.

6. The method according to claim 5, wherein the inflammatory bowel disease is ulcerative colitis or Crohn's disease.

* * * * *

SEQUENCE LISTING

```
<160> NUMBER OF SEQ ID NOS: 5

<210> SEQ ID NO 1
<211> LENGTH: 113
<212> TYPE: PRT
<213> ORGANISM: Homo sapiens

<400> SEQUENCE: 1

Met Arg Gly Ala Thr Arg Val Ser Ile Met Leu Leu Leu Val Thr Val
1               5                   10                  15

Ser Asp Cys Asp Tyr Lys Asp Asp Asp Lys Ala Val Ile Thr Gly
                20                  25                  30

Ala Cys Glu Arg Asp Val Gln Cys Gly Ala Gly Thr Cys Cys Ala Ile
            35                  40                  45

Ser Leu Trp Leu Arg Gly Leu Arg Met Cys Thr Pro Leu Gly Arg Glu
    50                  55                  60

Gly Glu Glu Cys His Pro Gly Ser His Lys Val Pro Phe Phe Arg Lys
65                  70                  75                  80

Arg Lys His His Thr Cys Pro Cys Leu Pro Asn Leu Leu Cys Ser Arg
                85                  90                  95

Phe Pro Asp Gly Arg Tyr Arg Cys Ser Met Asp Leu Lys Asn Ile Asn
                100                 105                 110

Phe

<210> SEQ ID NO 2
<211> LENGTH: 86
<212> TYPE: PRT
<213> ORGANISM: Homo sapiens

<400> SEQUENCE: 2

Ala Val Ile Thr Gly Ala Cys Glu Arg Asp Val Gln Cys Gly Ala Gly
1               5                   10                  15

Thr Cys Cys Ala Ile Ser Leu Trp Leu Arg Gly Leu Arg Met Cys Thr
                20                  25                  30

Pro Leu Gly Arg Glu Gly Glu Glu Cys His Pro Gly Ser His Lys Val
            35                  40                  45

Pro Phe Phe Arg Lys Arg Lys His His Thr Cys Pro Cys Leu Pro Asn
    50                  55                  60

Leu Leu Cys Ser Arg Phe Pro Asp Gly Arg Tyr Arg Cys Ser Met Asp
65                  70                  75                  80

Leu Lys Asn Ile Asn Phe
```

```
<210> SEQ ID NO 3
<211> LENGTH: 82
<212> TYPE: PRT
<213> ORGANISM: Homo sapiens

<400> SEQUENCE: 3

Ala Val Ile Thr Gly Ala Cys Glu Arg Asp Val Gln Cys Gly Ala Gly
1               5                   10                  15

Thr Cys Cys Ala Ile Ser Leu Trp Leu Arg Gly Leu Arg Met Cys Thr
                20                  25                  30

Pro Leu Gly Arg Glu Gly Glu Glu Cys His Pro Gly Ser His Lys Val
            35                  40                  45

Pro Phe Phe Arg Lys Arg Lys His His Thr Cys Pro Cys Leu Pro Asn
    50                  55                  60

Leu Leu Cys Ser Arg Phe Pro Asp Gly Arg Tyr Arg Cys Ser Met Asp
65                  70                  75                  80

Leu Lys

<210> SEQ ID NO 4
<211> LENGTH: 10
<212> TYPE: PRT
<213> ORGANISM: Homo sapiens

<400> SEQUENCE: 4

Cys Ser Met Asp Leu Lys Asn Ile Asn Phe
1               5                   10

<210> SEQ ID NO 5
<211> LENGTH: 15
<212> TYPE: PRT
<213> ORGANISM: Rattus norvegicus

<400> SEQUENCE: 5

Asp Phe Phe Ser Ala Arg Asp Gly Ser Gly Ala Glu Thr Ser Pro
1               5                   10                  15
```